United States Patent
Schmidt et al.

(10) Patent No.: US 6,182,898 B1
(45) Date of Patent: Feb. 6, 2001

(54) BAR CODE SCANNER WITH INTUITIVE HEAD AIMING AND COLLIMATED SCAN VOLUME

(75) Inventors: Mark C. Schmidt, Blackwood; Carl H. Knowles, Moorestown; David M. Wilz, Sr., Sewell; George B. Rockstein, Audobon, all of NJ (US)

(73) Assignee: Metrologic Instruments, Inc., Blackwood, NJ (US)

( * ) Notice: Under 35 U.S.C. 154(b), the term of this patent shall be extended for 0 days.

(21) Appl. No.: 09/444,587

(22) Filed: Nov. 22, 1999

Related U.S. Application Data

(63) Continuation of application No. 09/204,176, filed on Dec. 3, 1998, which is a continuation-in-part of application No. 08/645,335, filed on May 13, 1996, now Pat. No. 5,942,743, which is a continuation-in-part of application No. 08/615,054, filed on Mar. 12, 1996, which is a continuation-in-part of application No. 08/584,135, filed on Jan. 11, 1996, now Pat. No. 5,616,908, which is a continuation-in-part of application No. 08/573,949, filed on Dec. 18, 1995, now abandoned, which is a continuation-in-part of application No. 08/561,469, filed on Nov. 17, 1995, now abandoned, which is a continuation-in-part of application No. 08/489,305, filed on Jun. 9, 1995, now abandoned, which is a continuation-in-part of application No. 08/476,069, filed on Jun. 7, 1995, now Pat. No. 5,591,953, which is a continuation-in-part of application No. 08/365,193, filed on Dec. 28, 1994, now Pat. No. 5,557,093, which is a continuation-in-part of application No. 08/293,493, filed on Aug. 19, 1994, now Pat. No. 5,525,789, which is a continuation-in-part of application No. 08/292,237, filed on Aug. 17, 1994, now Pat. No. 5,808,285, which is a continuation-in-part of application No. 08/278,109, filed on Nov. 24, 1993, now Pat. No. 5,484,992.

(51) Int. Cl.$^7$ .................................................. G06K 7/10

(52) U.S. Cl. .......................... 235/462.45; 235/462.25; 235/462.32; 235/462.38; 235/472.01

(58) Field of Search .................... 235/462.45, 462.14, 235/462.17, 462.18, 462.2, 462.25, 462.32, 462.48, 472.01, 454

(56) References Cited

U.S. PATENT DOCUMENTS 5,047,617 * 9/1991 Shepard et al. .............. 235/472.01 X
5,343,027 * 8/1994 Knowles et al. ................. 235/449 X

* cited by examiner

*Primary Examiner*—Michael G Lee
(74) *Attorney, Agent, or Firm*—Hopgood, Calimafde, Kalil & Judlowe

(57) ABSTRACT

A fully automatic bar code symbol reading system comprising an automatic (i.e., triggerless) portable bar code symbol reading device with an omnidirectional projection laser scanning engine mounted within the head portion of its hand-supportable housing, and an associated base unit positioned within the data transmission range thereof without a physical wiring connection thereto. The hand-supportable bar code symbol reading device produces a narrowly confined scanning volume for omnidirectional scanning of code symbols presented therein, while preventing unintentional scanning of code symbols on nearby objects located outside thereof.

24 Claims, 40 Drawing Sheets

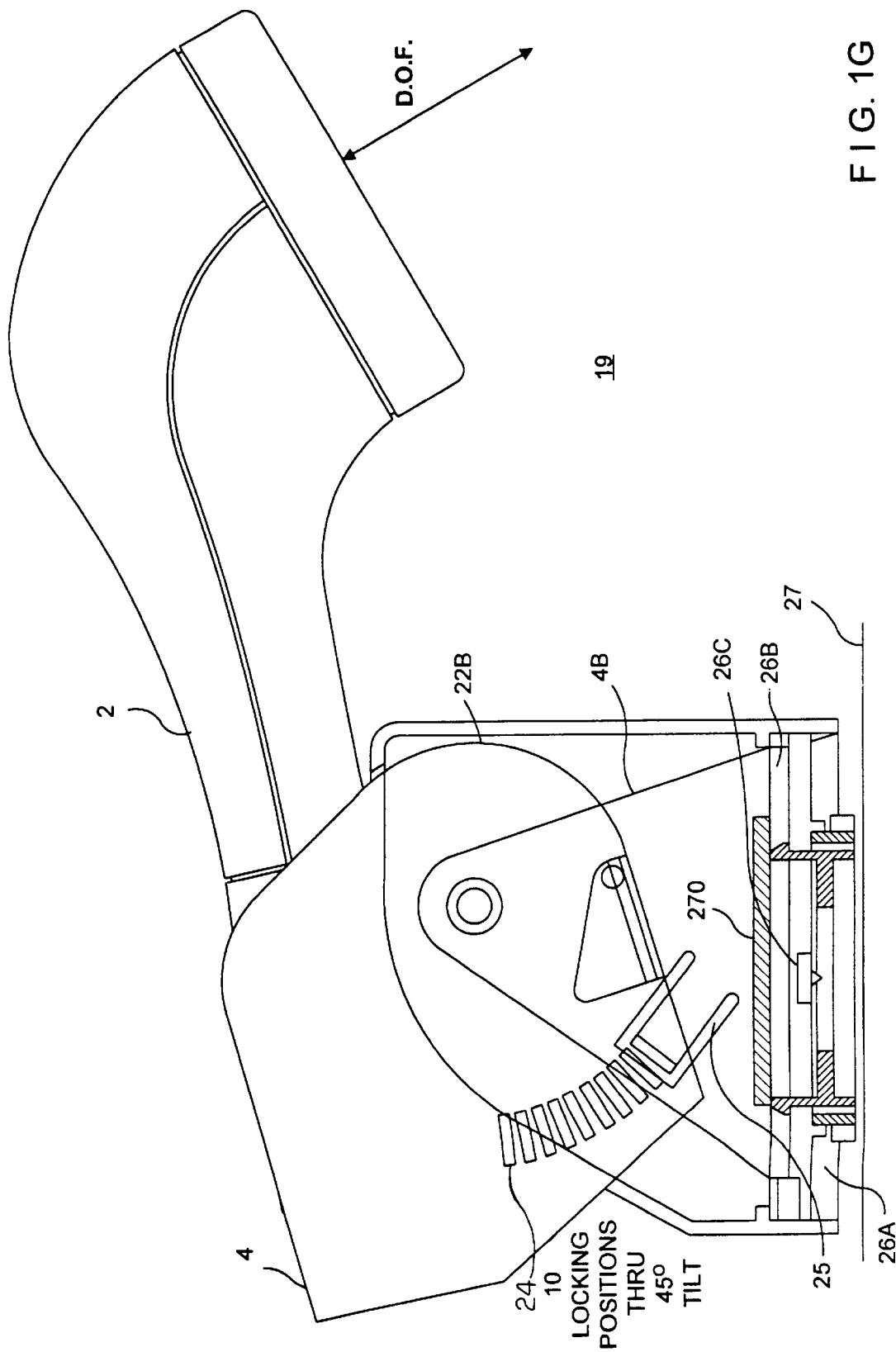

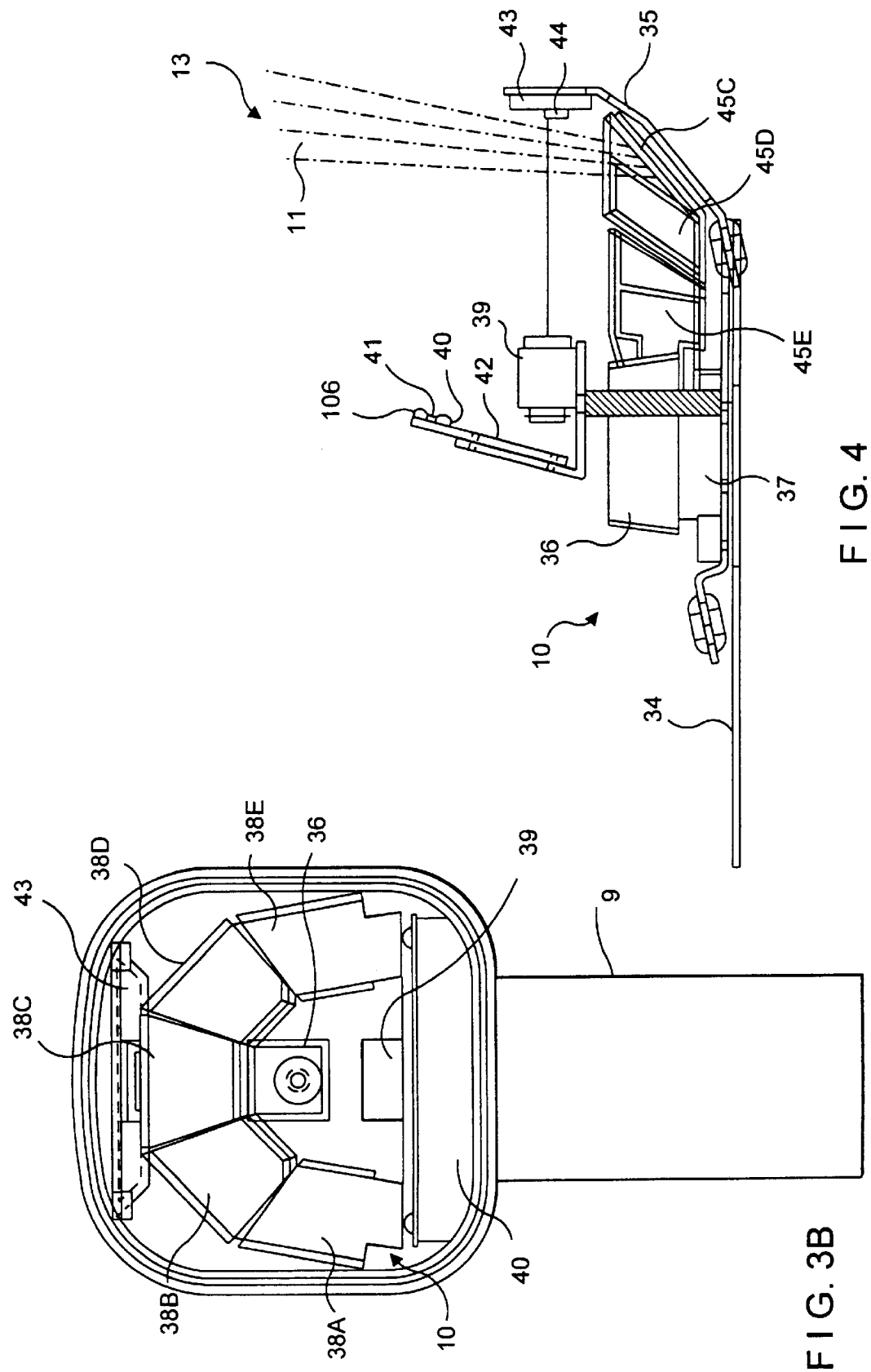

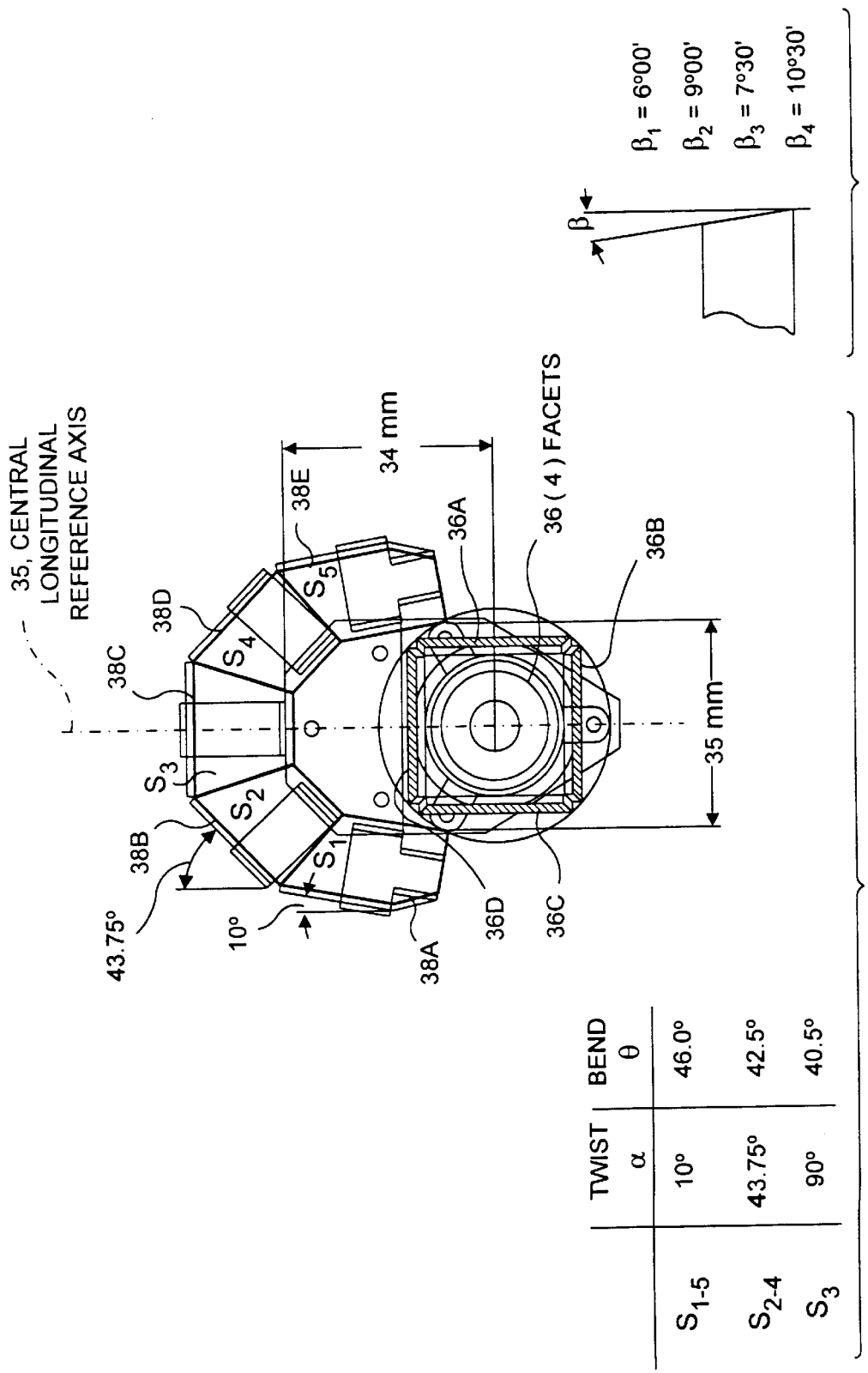

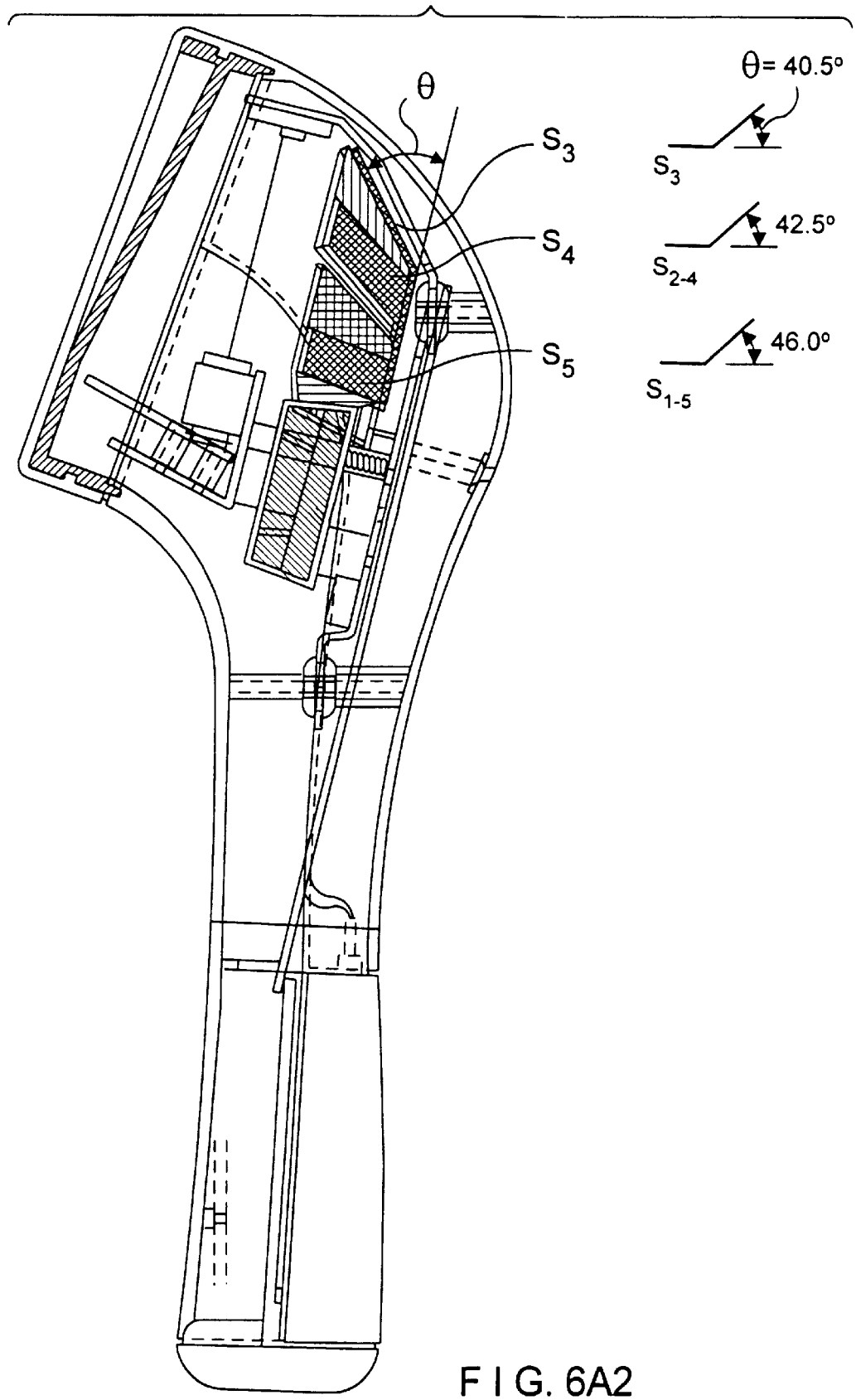
FIG. 6A2

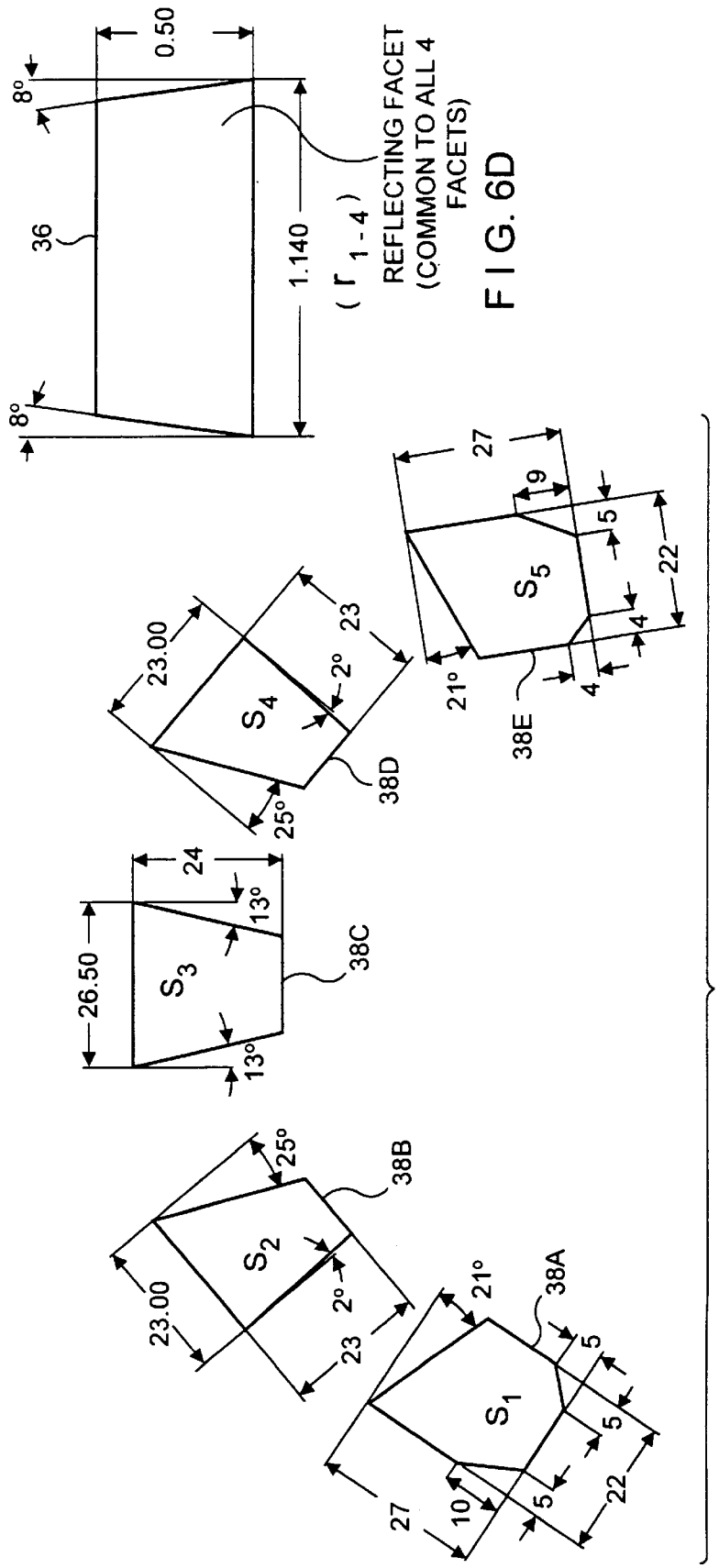

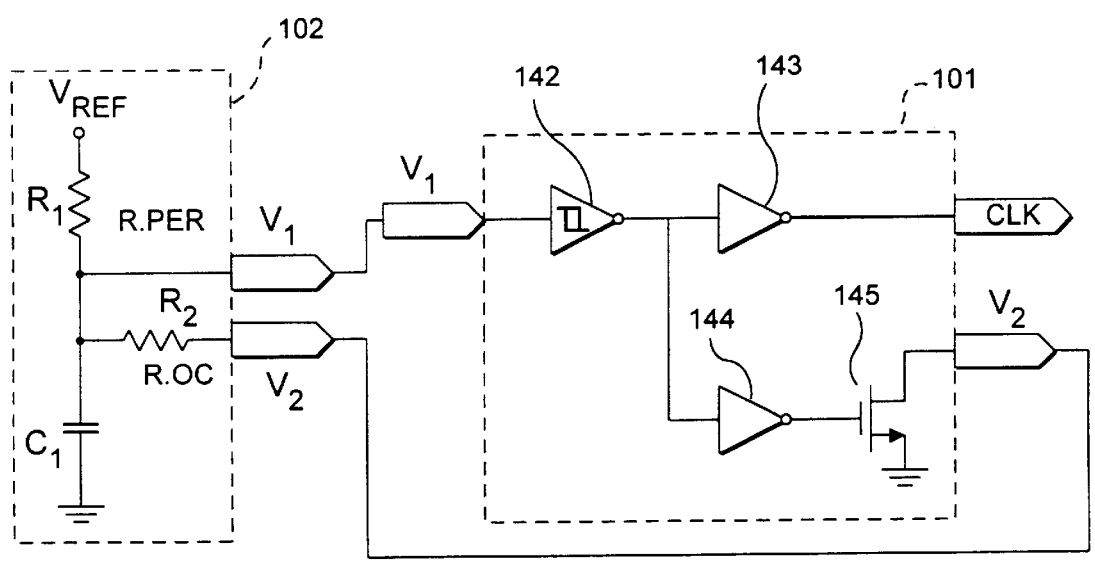
F I G. 8B $$E_0 = \overline{(B + A_0)(C_3/C_2 - 1)}$$
$$E_1 = (C_3/C_2 - 2) + B$$
$$E_2 = (C_2/C_1)(T_1)$$

| R | $C_3/C_2-1$ | $C_3/C_2-2$ | $E_3$ | $C_2/C_1$ |
|---|---|---|---|---|
| 0 | X | X | $A_{2L}$ | 0 |
| 1 | 0 | 0 | $A_{2L}$ | 0 |
| 1 | 0 | 1 | $A_{2S}$ | 0 |
| X | 1 | 1 | X | 1 |
| | | X = DON'T CARE | | |

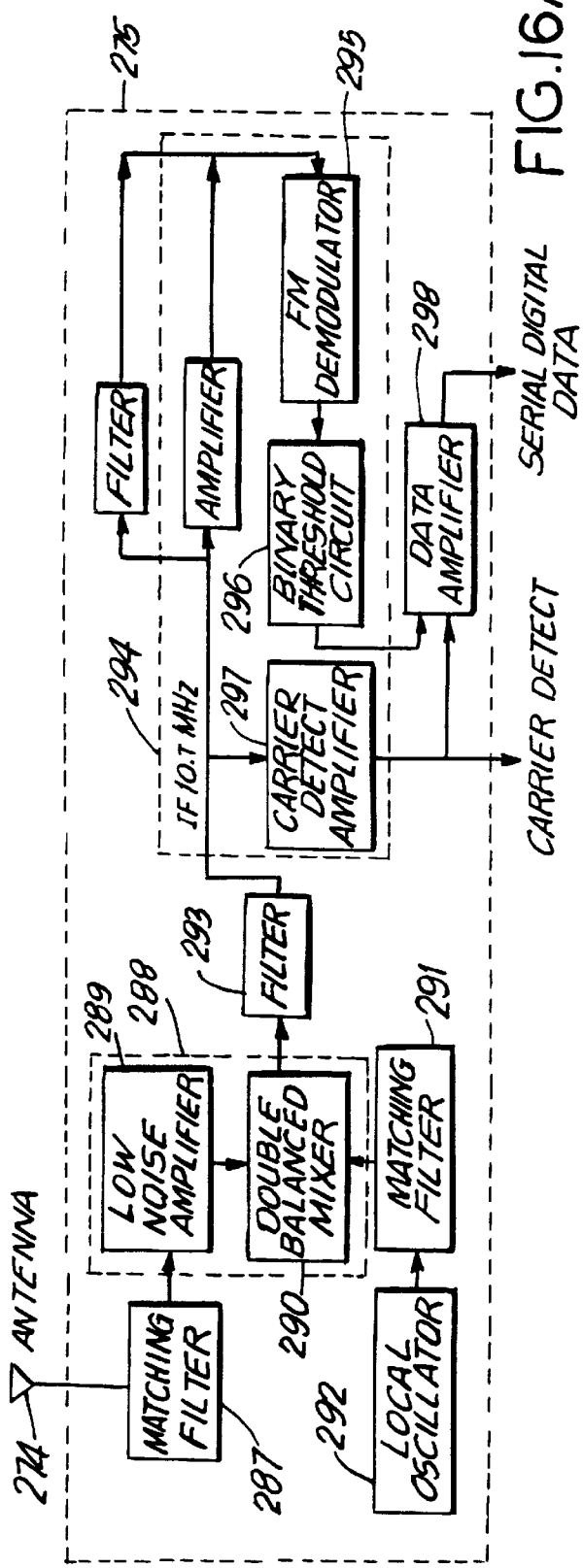
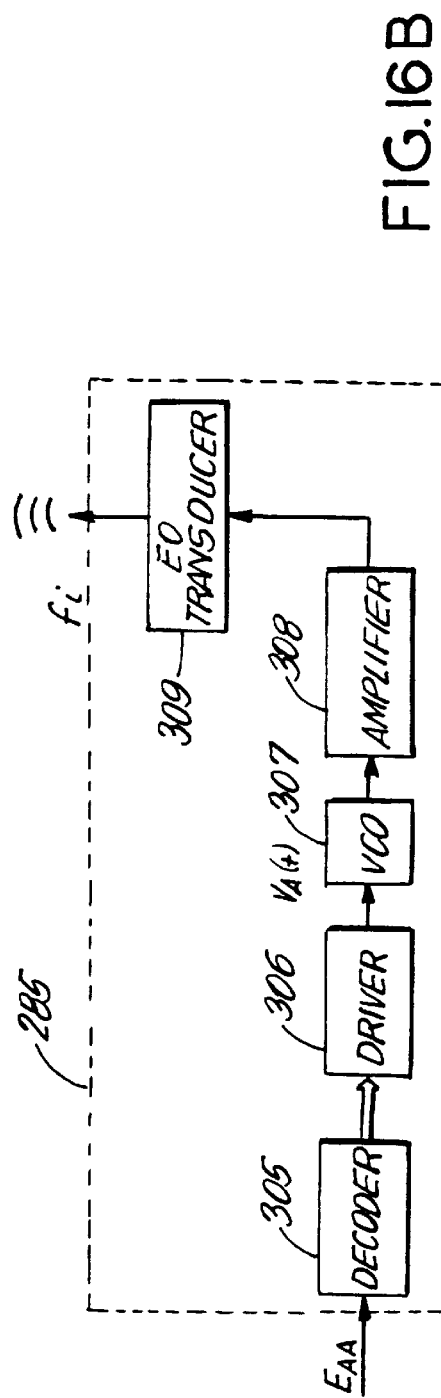
FIG.16A
FIG.16B

BAR CODE SCANNER WITH INTUITIVE HEAD AIMING AND COLLIMATED SCAN VOLUME

This is a continuation of patent application Ser. No. 09/204,176, filed on Dec. 3, 1998, now pending, which is a Continuation-In-Part of patent application Ser. No. 08/645,335, filed May 13, 1996, now issued as U.S. Pat. No. 5,942,743 on Aug. 24, 1999, which is a Continuation-In-Part of patent application Ser. No. 08/615,054, filed on Mar. 12, 1996, now pending, which is a Continuation-In-Part of Ser. No. 08/573,949, filed on Dec. 18, 1995, and now abandoned, which is a Continuation-In-Part of Ser. No. 08/292,237, filed on Aug. 17, 1994, now issued as U.S. Pat. No. 5,808,285 on Sep. 15, 1998, which is a Continuation-In-Part of Ser. No. 08/365,193, filed on Dec. 28, 1994, now issued as U.S. Pat. No. 5,557,093 on Sep. 17, 1996, which is a Continuation-In-Part of Ser. No. 08/293,493, filed on Aug. 19, 1994, now issued as U.S. Pat. No. 5,525,789 on Jun. 11, 1996, which is a Continuation-In-Part of Ser. No. 08/561,469, filed on Nov. 17, 1995, now abandoned, which is a Continuation-In-Part of Ser. No. 08/278,109, filed on Nov. 24, 1993, now issued as U.S. Pat. No. 5,484,992 on Jan. 16, 1996, which is a Continuation-In-Part of Ser. No. 08/489,305, filed on Jun. 9, 1995, now abandoned, which is a Continuation-In-Part of Ser. No. 08/476,069 filed on Jun. 7, 1995, now issued as U.S. Pat. No. 5,591,953 on Jan. 7, 1997, which is a Continuation-In-Part of Ser. No. 08/584,135, filed on Jan. 11, 1996, now issued as U.S. Pat. No. 5,616,908 on Apr. 1, 1997. Each of the above issued patents and patent applications are assigned to and commonly owned by Metrologic Instruments, Inc. of Blackwood, N.J., and are incorporated herein by reference in their entirety.

BACKGROUND OF THE INVENTION

1. Field of the Invention

The present invention relates generally to laser scanning systems, and more particularly to an automatic bar code symbol reading system in which an automatic hand-supportable laser scanner can be interchangeably utilized as either a portable hand-held laser scanner in an automatic "hands-on" mode of operation, or as a stationary laser projection scanner in an automatic "hands-free" mode of operation.

2. Brief Description of the Prior Art

Bar code symbols have become widely used in many commercial environments such as, for example, point-of-sale (POS) stations in retail stores and supermarkets, inventory and document tracking, and diverse data control applications. To meet the growing demands of this recent technological innovation, bar code symbol readers of various types have been developed for scanning and decoding bar code symbol patterns and producing symbol character data for use as input in automated data processing systems.

In general, prior art hand-held bar code symbol readers using laser scanning mechanisms can be classified into two major categories.

The first category of hand-held laser-based bar code symbol readers includes manually-actuated trigger-operated systems having lightweight, hand-held laser scanners which can be supported in the hand of the user. The user positions the hand-held laser scanner at a specified distance from the object bearing the bar code symbol, manually activates the scanner to initiate reading and then moves the scanner over other objects bearing bar code symbols to be read. Prior art bar code symbol readers illustrative of this first category are disclosed in U.S. Pat. Nos. 4,387,297 to Swartz; U.S. Pat. No. 4,575,625 to Knowles; U.S. Pat. No. 4,845,349 to Cherry; U.S. Pat. No. 4,825,057 to Swartz, et al.; U.S. Pat. No. 4,903,848 to Knowles; U.S. Pat. No. 5,107,100 to Shepard, et al.; U.S. Pat. No. 5,080,456 to Katz, et al.; and U.S. Pat. No. 5,047,617 to Shepard, et al.

The second category of hand-held laser-based bar code symbol readers includes automatically actuated systems having lightweight triggerless hand-held laser scanners which can be supported in the hand of the user. The user positions the hand-held laser scanner, at a specified distance from the object bearing the bar code the presence of the object is automatically detected, the presence of the bar code symbol on the object is detected, and thereafter the detected bar code symbol automatically read. Prior art illustrative of this second category of laser-based bar code symbol reading systems are disclosed in U.S. Pat. No. 4,639,606 to Boles, et al., and U.S. Pat. No. 4,933,538 to Heiman, et al.

While prior art hand-held and stationary laser scanners have played an important role in the development of the bar code symbol industry, these devices have, however, suffered from a number of shortcomings and drawbacks. For example, hand-held laser scanners, although portable and lightweight, are not always convenient to use in assembly-line applications where the user processes bar coded objects over an extended period of time, or where the user requires the use of both hands in order to manipulate the objects. In some applications, hand-held laser scanners are difficult to manipulate while simultaneously moving objects or performing other tasks at a point-of-sale terminal. Stationary laser scanners, on the other hand, provide a desired degree of flexibility in many applications by allowing the user to manipulate bar coded objects with both hands. However, by their nature, stationary laser scanners render scanning large, heavy objects a difficult task as such objects must be manually moved into or through the laser scan field.

Attempting to eliminate the problems associated with the use of hand-held and stationary laser scanners, U.S. Pat. No. 4,766,297 to McMillan discloses a bar code symbol scanning system which combines the advantages of hand-held and stationary fixed laser scanners into a single scanning system which can be used in either a hands-on or hands-free mode of operation.

The bar code symbol scanning system in U.S. Pat. No. 4,766,297 includes a portable hand-held laser scanning device for generating, electrical signals descriptive of a scanned bar code symbol. In the hands-on mode of operation, a trigger on the hand-held laserl scanning device is manually actuated each time a bar code symbol on an object is to be read. The system further includes a fixturel having a head portion for receiving and supporting the hand-held laser scanning device, and a base portion above which the head portion is supported at a predetermined distance. In the hands-free mode of operation, the hand-held laser scanning device is supported by the fixture head portion above the fixture base portion in order to allow objects bearing bar code symbols to pass between the head and base portions of the fixture. In order to detect the presence of an object between the head and base portions of the fixture, the fixture also includes an object sensor operably connected to the hand-held laser scanning device. When the object sensor senses an object between the head portion and the base portion, the object sensor automatically initiates the hand-held laser scanning device supported in the fixture to read the bar code symbol on the detected object.

While the bar code symbol scanning system of U.S. Pat. No. 4,776,297 permits reading of printed bar code information using either a portable "hands-on" or stationary "hands-free" mode of operation, this system suffers from several significant shortcomings and drawbacks as well.

In particular, in the hands-on mode of operation, scanning bar code symbols requires manually actuating a trigger each time a bar code symbol is to be read. In the hands-free mode of operation, scanning bar code symbols requires passing the object bearing the bar code between the head and base portions of the fixture. However, in many instances where both hands are required to manipulate a bar coded object, the object is too large to be passed between the head and base portions of the fixture and thus scanning of the bar code symbol is not possible.

In an attempt to address such problems, several hand-held projection laser scanners have been developed for omnidirectional code symbol scanning. Examples of such systems include the NCR 7890 presentation scanner from the NCR Corporation and the LS9100 omnidirectional laser scanner from Symbol Technologies, inc. While each of these systems produces an omnidirectional laser scan pattern from a hand-supportable housing and have hands-free and hands-on modes of operation, each of these scanning devices suffer from a number of shortcomings and drawbacks. In particular, the spatial extent of the laser scan pattern produced from each of these scanners frequently results in the inadvertent scanning of code symbols on products placed near the scanner during its hands-free mode of operation. In the hands-on mode of operation, it is virtually impossible to use the scanners to read bar code symbol menus provided in diverse application environments. Moreover, in each of these scanner designs, the scanner is tethered to its base unit by a power/signal cord, and the user is required to handle the scanner housing in an awkward manner in the hands-on mode of operation, resulting in strain and fatigue and thus a decrease in productivity. In addition, the control structure provided in each of these hand-held projection scanners operates the scanner components in a manner which involves inefficient consumption of electrical power, and prevents diverse modes of automatic code symbol reading which would be desired in portable scanning environments.

Thus, there is a great need in the bar code symbol reading art for a bar code symbol reading system which overcomes the above described shortcomings and drawbacks of prior art devices and techniques, while providing greater versatility in its use.

OBJECTS AND SUMMARY OF THE INVENTION

Accordingly, it is a primary object of the present invention to provide a fully automatic bar code symbol reading system having an automatic hand-supportable laser scanning device which can be used at a point-of-sale (POS) station as either a portable hand-supported laser scanner when operated in its automatic hands-on mode of operation, or as a stationary laser projection scanner when operated in its automatic hands-free mode of operation.

It is another object of the present invention to provide such an automatic bar code symbol reading system, wherein a highly collimated laser scanning pattern is projected from the hand-supportable device about a projection axis, and comprises laser scanning planes which intersect within a narrowly confined scanning volume extending about the projection axis so that bar code symbols disposed within the scanning volume can be read omnidirectionally, while inadvertent scanning of bar code symbols outside of the scanning volume is prevented.

It is another object of the present invention to provide such an automatic bar code symbol reading system, wherein the projection axis about which the narrowly confined scanning volume extends is substantially coplanar with the longitudinal axis of the head and if handle portions of the hand-supportable housing.

It is another object of the present invention to provide an automatic hand-supportable laser projection scanner having a center-of-mass which provides easy handling, consistent with ergonometric design principles, for fatigue-free omnidirectional scanning of bar code symbols.

Another object of the present invention to provide automatic hand-supportable omnidirectional laser prolection scanner with a hand-supportable housing that allows to user to easily control the direction of its projection axis by way of the handle portion of the housing, and thus align the narrowly confined scanning volume; of the scanner with the bar code symbol on the object to be scanned and identified.

Another object of the present invention to provide a portable automatic hand-supportable omnidirectional laser projection scanner with a power-conserving control system that provides battery power to the system components of the scanner in an intelligent manner.

Another object of the present invention to provide an. automatic hand-supportable omnidirectional laser projection scanner having a hand-supportable housing with a scan-head that visually, indicates the direction of the projection axis, for intuitive hand-supported omnidirectional scanning of bar code symbols within the narrowly confined scanning volume extending thereabout.

It is another object of the present invention to provide such an automatic bar code symbol reading system, in which one or more bar code symbols on an object can be automatically read in a consecutive manner.

A further object is to provide such an automatic bar code symbol reading device, in which the automatic hand-supportable bar code (symbol) reading device has an infrared light object detection field which spatially encompasses at least a portion of its volumetric scanning field along the operative scanning range of the device, thereby improving the laser beam pointing efficiency of the device during the automatic bar code reading process of the present invention.

Another object of the present invention is to provide such an automatic bar code reading system with a scanner support stand that supports the hand-supportable housing of the device in a selected mounting position, and permits complete gripping of the handle portion of the hand-supportable housing prior to removing it therefrom.

Another object of the present invention is to provide an automatic bar code symbol reading system, in which battery power from a supply within the hand-supportable housing of its portable bar code symbol reading device is automatically metered out and provided to the power distribution circuitry thereof for a predetermined time period which is reset upon the occurrence of either the manual actuation of an externally mounted power reset button, the reading (i.e. scanning and decoding) of a valid bar code symbol, or the placement of the hand-supportable bar code symbol reading device within its scanner support stand.

A further object of the present invention is to provide such an automatic bar code symbol reading device, with a novel automatic power control circuit that effectively conserves the consumption of battery power therein, without compromising the operation, or performance of the device during its diverse modes of automatic operation.

It is another object of the present invention is to provide an automatic hand-supportable bar code reading device having both long and short-range modes of bar code symbol reading, automatically selectable in a variety of different ways, (e.g. by, placing the hand-supportable device within its support stand, removing it therefrom).

Another object of the present invention is to provide such a multi-mode automatic bar code symbol reading device, so that it can: be used in various bar code symbol reading applications, such as, for example, charge coupled device (CCD) scanner emulation, counter-top projection scanning in the hands-free long-range mode of operation, or the like.

Another object of the present invention is to provide an automatic hand-supportable bar code reading device with a programmably selectable mode of operation that prevents multiple reading of the same bar code symbol due to dwelling of the laser scanning beam upon a bar code symbol for an extended period of time, yet allows a plurality of bar code symbols (e.g. representing the same UPC) to be read in a consecutive manner even though they are printed on the same, or apparently the same, object or surface, as often is the case in inventory scanning applications.

A further object of the present invention is to provide a point-of-sale station (POS) incorporating the automatic bar code symbol reading system of the present invention.

It is a further object of the present invention is to provide an automatic hand-supportable bar code reading device having a control system which has a finite number of states through which the device may pass during its automatic operation, in response to diverse conditions automatically detected within the object detection and scanning fields of the device.

Another object of the present invention is to provide a portable, automatic bar code symbol reading device, wherein the laser beam scanning motor is operated at a lower angular velocity during its object detection state to conserve battery power consumption and facilitate rapid steady-state response when the device is induced into its bar code symbol detection and bar code symbol reading states of operation.

Another object of the present invention is to provide a portable automatic bar code symbol reading device, wherein the laser beam scanning motor is denergized during its object detection state to conserve battery power consumption therewhile, and is momentarily overdriven to facilitate rapid steady-state response when the device undergoes a transition from the object detection state to the bar code symbol detection state of operation.

Another object of the present invention is to provide a novel mechanism for mounting a projection laser scanning platform within the head portion of an automatic hand-supportable omnidirectional projection laser scanner.

Another object of the present invention is to provide a novel omnidirectional laser scanning platform for use within an automatic portable projection laser scanner.

Another object of the present invention is to provide a bar code symbol reading system having at least one hand-supportable bar code symbol reading device which, after each successful reading of a code symbol, automatically synthesizes and then transmits a data packet to a base unit positioned within the data transmission range of the bar code symbol reading device, and upon the successful receipt of the transmitted data packet and recovery of symbol character data therefrom, the base unit transmits an acoustical acknowledgement signal that is perceptible to the user of the bar code symbol reading device residing within the data transmission range thereof.

A further object of the present invention is to provide such a system with one or more automatic (i.e., triggerless) hand-supportable laser-based bar code symbol reading devices, each of which is capable of automatically transmitting data packets to its base unit after each successful reading of a bar code symbol.

A further object of the present invention is to provide such a bar code symbol reading system in which the hand-supportable bar code symbol reading device can be used as either a portable hand-supported laser scanner in an automatic hands-on mode of operation, or as a stationary laser projection scanner in an automatic hands-free mode of operation.

A further object of the present invention is to provide such a bar code symbol system in which the base unit contains a battery recharging device that automatically recharges batteries contained in the hand-supportable device when the hand-supportable device is supported within the base unit.

It is another object of the present invention to provide such an automatic bar code symbol reading system with a mode of operation that permits the user to automatically read one or more bar code symbols on an object in a consecutive manner.

A further object of the present invention is to provide such an automatic bar code symbol reading system, in which a plurality of automatic hand-supportable bar code symbol reading devices are used in conjunction with a plurality of base units, each of which is assigned to a particular bar code symbol reading device.

A further object of the present invention is to provide such an automatic bar code symbol reading system, in which radio frequency (RF) carrier signals of the same frequency are used by each hand-supportable bar code symbol reading device to transmit data packets to respective base units.

A further object of the present invention is to provide such an automatic bar code symbol reading system, in which a novel data packet transmission and reception scheme is used to minimize the occurrence of data packet interference at each base unit during data packet reception.

A further object of the present invention is to provide such an automatic bar code symbol reading system, in which the novel data packet transmission and reception scheme enables each base unit to distinguish data packets associated with consecutively different bar code symbols read by a particular bar code symbol reading device, without the transmission of electromagnetic-based data packet acknowledgment signals after receiving each data packet at the base unit.

It is a further object of the present invention to provide an automatic hand-supportable bar code reading device having a control system which has a finite number of states through which the device may pass during its automatic operation, in response to diverse conditions automatically detected within the object detection and scan fields of the device.

It is yet a further object of the present invention to provide a portable, fully automatic bar code symbol reading system which is compact, simple to use and versatile.

Yet a further object of the present invention is to provider a novel method of reading bar code symbols using an automatic hand-supportable omnidirectional laser scanning device.

These and further objects of the present invention will become apparent hereinafter and in the Claims to Invention.

BRIEF DESCRIPTION OF THE DRAWINGS

For a fuller understanding of the Objects of the Invention, the Detailed Description of the Illustrated Embodiments of the Present Invention should be read in conjunction with the accompanying drawings, wherein:

FIGS. 1F and 1G provide an elevated side view of the illustrative embodiment of the automatic bar code symbol reading device hereof, shown supported within the scanner support stand portion of its matching base unit, arranged for automatic hands-free operation in a second scanning position;

FIG. 3B is an elevated, end view of the automatic bar code symbol reading device of the present invention, taken along line 3B—3B of FIG. 1D, showing the various components contained therein;

FIG. 4 is an elevated side view of the laser scanning platform of the present invention realized on its shock-mounted optical bench, removed from the housing of the hand-supportable bar code symbol reading device of the present invention;

FIGS. 6A1, 6A2 and 6B provide a geometrical optics model of the stationary mirror array of the laser scanning platform of the illustrative embodiment, graphically defining the various angles used to configure the stationary mirrors relative to the central reference plane thereof;

FIG. 6C is a geometrical optics model of the stationary mirror array of the laser scanning platform of the illustrative embodiment, graphically defining the various physical dimensions stationary mirrors relative to the central reference plane thereof;

FIG. 6D is a geometrical optics model of the stationary mirror array of the laser scanning platform of the illustrative embodiment, graphically defining the various physical dimensions stationary mirrors relative to the central reference plane thereof;

FIG. 8B is a functional logic diagram of the oscillator circuit in the Application Specific Integrated Circuit (ASIC) chip in the automatic bar code symbol reading device of the present invention;

FIG. 16A is a functional block diagram of the radio receiver subcircuit of the data packet receiving circuit of FIG. 16;

FIG. 16B is a functional block diagram of the digitally controlled acoustical acknowledgment signal generating circuit of the present invention;

DETAILED DESCRIPTION OF THE ILLUSTRATIVE EMBODIMENT OF THE PRESENT INVENTION

Figure 1A:
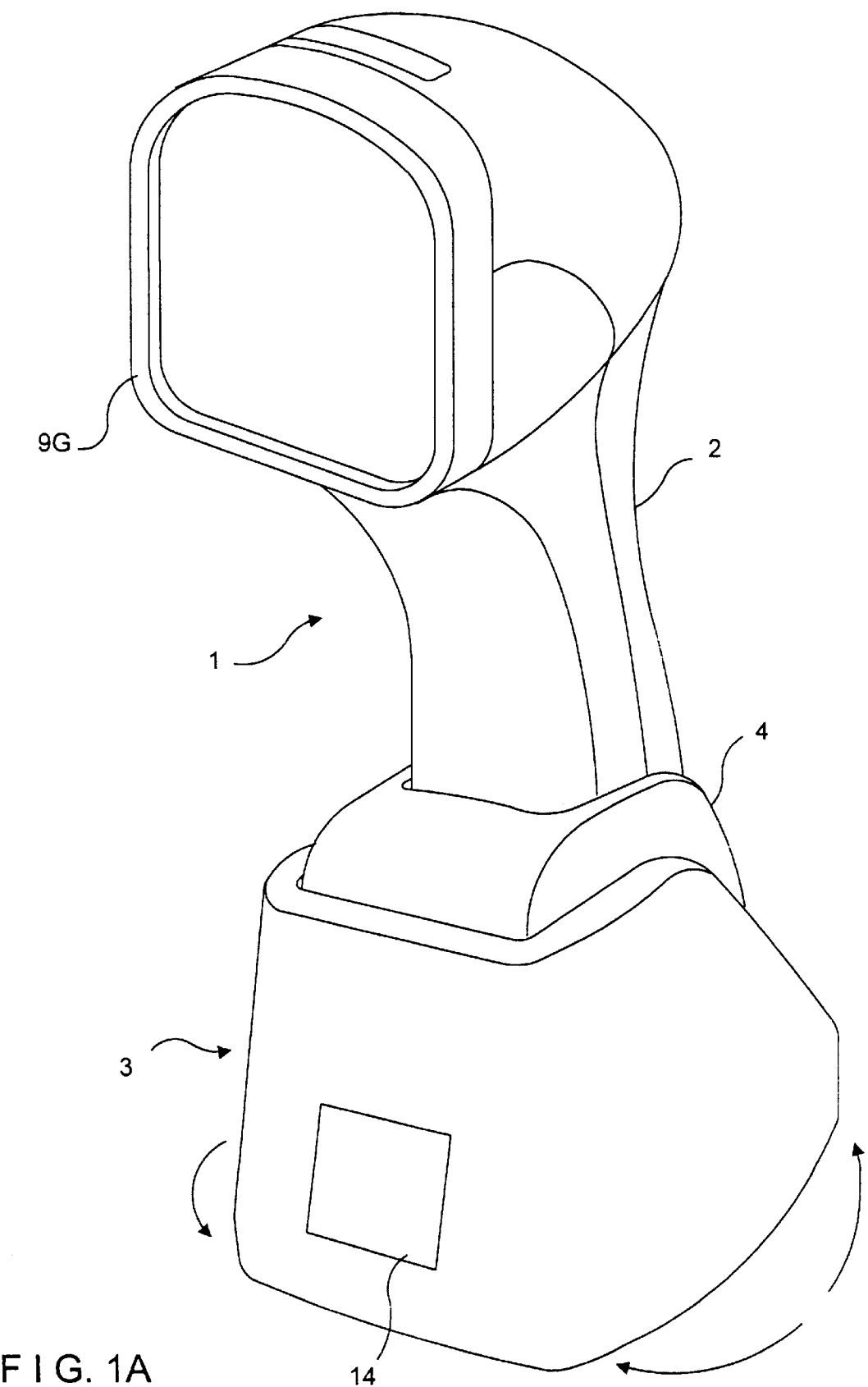
FIG. 1A is an elevated perspective view of the illustrative embodiment of the automatic bar code symbol reading system hereof, with its hand-supportable bar code symbol reading device shown supported within the scanner support stand portion of its matching base unit, and arranged for automatic hands-free operation.

As shown in FIGS. 1 to 3B, automatic bar code symbol reading system 1 of the illustrative embodiment of the present invention comprises an automatic (i.e., triggerless) portable bar code (symbol) reading device 2 operably associated with a base unit 3 having a scanner support stand 4 pivotally connected thereto, for releasably supporting the automatic bar code symbol reading device 2 at any one of a number of positions above of a counter surface at a Point of Sale (POS) station. In the preferred embodiment, the bar code symbol reading device 2 is operably connected with its the base unit 3 by way of a one way electromagnetic link 5 that is momentarily created between bar code symbol reading device 2 and its mated base unit 3 after the successful reading of each bar code symbol by the bar code symbol reading device. Operable interconnection between the base unit and a host system (e.g., electronic cash register system, data collection device, etc.) 6 is achieved by a flexible multiwire communications cable. 7 extending from the base unit and plugged directly into the data-input communications port of the host computer system 6. In the illustrative embodiment, electrical power from a low voltage direct current (DC) power supply (not shown) is provided to the base unit by way of a flexible power cable 8. Notably, this DC power supply can be realized in host computer system 6 or as a separate DC power supply adapter pluggable into a conventional 3-prong electrical socket. In other embodiments of the present invention, cables 7 and 8 can be integrated to provide a single flexible, multi-wire cable for transmission of power to the base unit and data to the host system. As will be described in greater detail hereinafter, a rechargeable battery power supply unit 20 is contained primarily within the handle portion of the bar code symbol reading device 2 in order to energize the electrical and electro-optical components within the device.

Figure 1B:
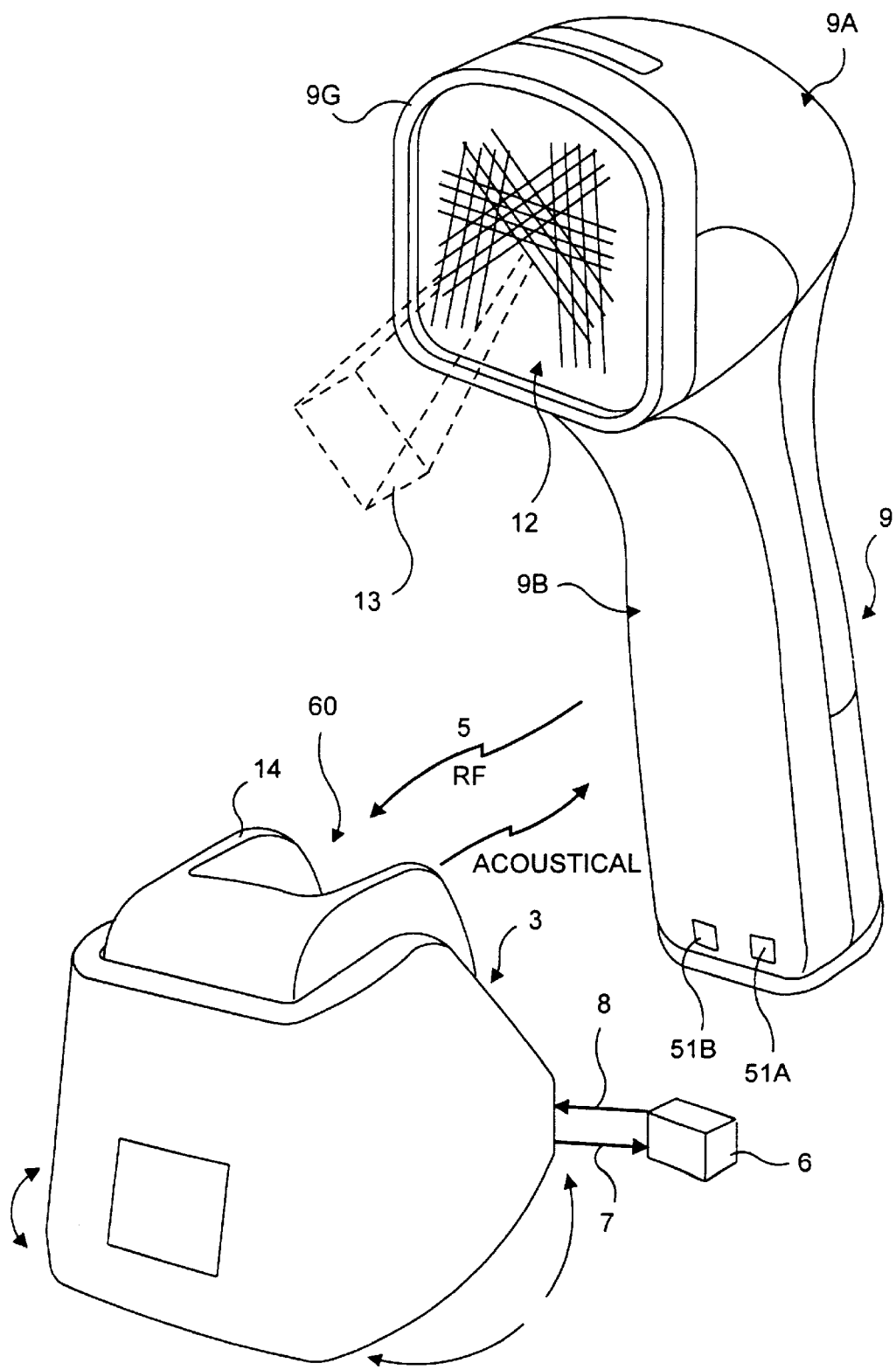
FIG. 1B is an elevated perspective view of the illustrative embodiment of the automatic bar code symbol reading device hereof, shown being used in its automatic hands-on mode of operation.

As illustrated in FIGS. 1A through 1B, scanner support stand 4 is particularly adapted for receiving and supporting portable bar code symbol reading device 2 without user support, thus providing a stationary, automatic hands-free mode of operation. In general, portable bar code symbol reading device 2 includes an ultra-light weight hand-supportable housing 9 having a head portion 9A and a contoured handle portion 9B. As will be described in greater detail hereinafter, head portion 9A encloses electro-optical components which are arranged in a novel scanning platform 10 of ultra compact construction which renders possible the production of a highly collimated scanning pattern 11 through light transmission window 12 for the purpose of scanning bar code symbols on objects within a narrowly confined scanning (i.e., 3-D scan field) volume 13, while preventing unintentional scanning of, bar code symbols on objects located outside thereof at point of sale (POS) stations. Thus, by minimizing the amount of counter-space that must be clear (i.e. free) of bar coded items at point of sale POS stations, the laser scanner of the present invention provides retailers with greater counter-space availability for displaying merchandise and the like, yet without sacrificing the; increase in check-out performance and worker productivity associated with the use of bar code symbol scanners at POS stations.

Figures 1C, 1D:
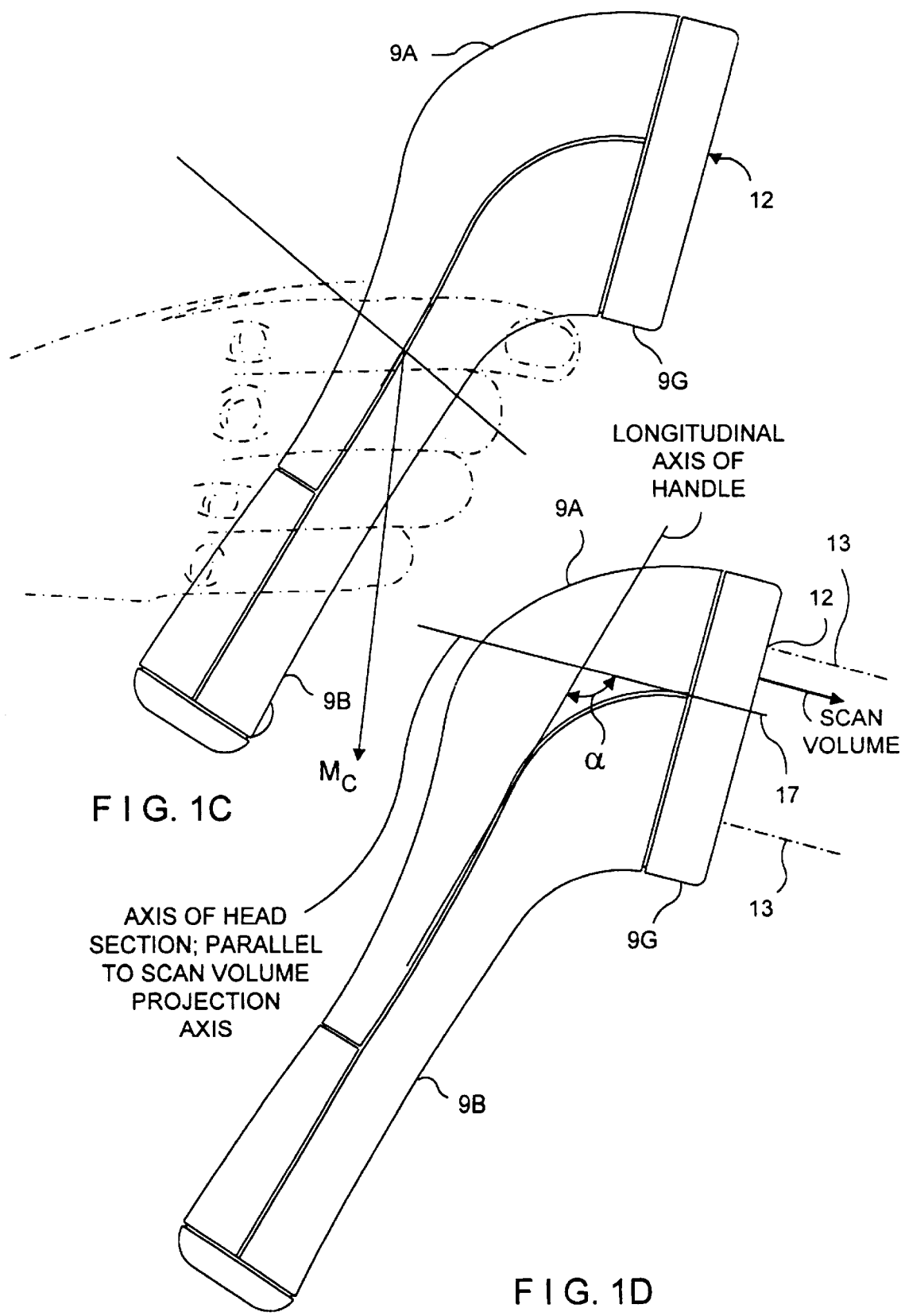
FIG. 1C is an elevated side view of the illustrative embodiment of the automatic bar code symbol reading device hereof, illustrating that the mass balance of the hand-supportable bar code symbol reading device has been designed to minimize torques about the point of pivot of the housing which occurs about the user's index finger in order to maximize its ergonomic handling efficiency eliminate fatigue during automatic hands-on, omnidirectional laser scanning operations.
FIG. 1D is an elevated side view of the illustrative embodiment of the automatic bar code symbol reading device hereof, illustrating the spatial alignment of the longitudinal axis of the head portion of the scanner and the projection axis of the laser scanning platform contained therein.

As illustrated in FIGS. 1 through 1C, the base unit 3 includes a base portion 14 which can be realized in a variety of different ways. For example, the base portion 14 can be realized, as a compact stand for support upon a countertop surface as shown in FIG. 18, or it can be realized as a support mount for vertical wall-mounting. In either embodiment, the function of the scanner stand 4 is to support the device in any one of a plurality of positions above a workspace 19 which may be a counter surface in POS applications. With this arrangement, the highly collimated scanning pattern 11 can be projected about the projection axis 17 above the counter surface in any one of a plurality of orientations corresponding to the plurality of positions.

Figures 15A, 15B:
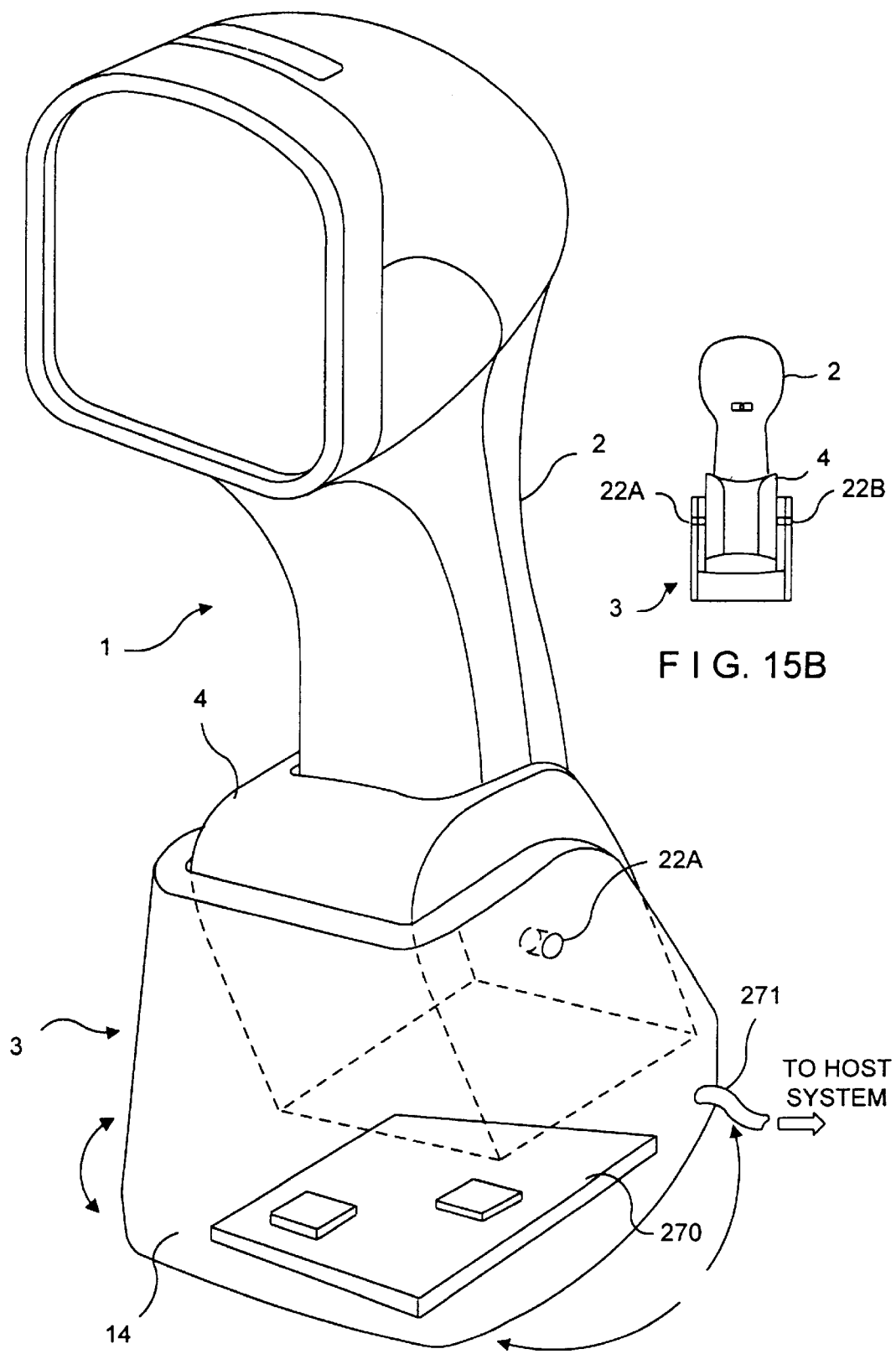
FIG. 15A is a perspective view of the scanner support stand portion of the countertop base unit of the present invention.
FIG. 15B is a perspective view of the base plate portion of the countertop base unit of the present invention.

As shown in FIGS. 1A and 15A, base portion 14 contains electronic circuitry realized on a PC board 16 for carrying out various types of functions, namely: reception of electrical power from the host system and coupling electrical power to the rechargeable battery contained within the hand-supportable housing; reception of data packets transmitted from the automatic bar code symbol reading device, and processing the same for data recovery; generation of acoustical and/or optical acknowledgement signals; and transmission of symbol character data to the host system. Each of these functions will be described in greater detail hereinafter with reference to FIGS. 15A and 15B.

As illustrated in FIGS. 1B and 1C in particular, the head portion 9A continuously extends into contoured handle portion 9B at an obtuse angle α which, in the illustrative embodiment, is about 115 degrees. It is understood, however, that in other embodiments obtuse angle a may be in the range of about 100 to about 150 degrees. As illustrated in FIG. 1C, the mass balance of the device is particularly designed so that when the device is held within the user's hand, the index finger of the user is disposed beneath the head portion of the housing, and provides a pivot point about which there is substantially zero torque acting upon the device, preventing it from rotating in either direction about the index finger. Instead, the resultant force distribution acting upon the user's hand is aligned in the direction of gravitational forces, as indicted in FIG. 1C. The effect of this mass-balanced scanner design is to minimize the torque imposed on the user's wrists and forearms while using the bar code symbol reading device in the hands-on mode of operation. This, in turn, minimizes the amount of energy which the user must expend during hands-on scanning operations, thereby reducing wrist and arm fatigue and increasing worker productivity. In addition to the above, advantages, the hand-supportable housing hereof is sculptured (i.e., form-fitted) to the human hand so that automatic hands-on; scanning is rendered easy and effortless. Also, the ergonomic housing design eliminates the risks of musculoskeletal disorders, such as carpal tunnel syndrome, which can result from repeated biomechanical stress commonly associated with pointing prior art gun-shaped scanners at bar code symbols, and squeezing a trigger to activate the laser scanning beam, and then releasing the trigger.

As best shown in FIGS. 1G, 15A and 15B, stand portion 4 of the base unit 3 is pivotally supported with respect to the base portion by way of pivot pins 22A and 22B. In order to releasably hold the stand portion of the base unit relative to the base portion thereof in any one of a number of provided scanning positions, a releasable stand-locking mechanism 23 is provided. As shown in FIG. 1G, the locking mechanism is realized as a set of projections 24 formed on the inside surface of the support arms 4A of the stand portion of the base unit, and a projection-catch 25 formed on the adjacent surface of the base portion. These structure features of the base unit are shown in FIG. 1G. rhe function of the projection catch 25 is to releasably engage one of the projections 24 associated with the selected scanning position. Gentle rotation of the head portion of the scanner while supported in its stand causes the projection caught in the projection-catch 25 to release therefrom, allowing the scanner to be repositioned as desired. At the resulting scanning position, the corresponding projection 24 automatically engages with the projection-catch 25 and locks the stand portion of the base unit relative to the base portion thereof.

In addition, to allow the base unit to easily rotate relative to its support surface, the bottom of the base portion is realized as a turntable structure that allows its bottom section 26A to be stationary relative to the support surface (i.e. countertop) 27, while the upper section 26B is fixed relative to the balance of the base portion of the base unit. A pivot 26C is used to pivotally connect the upper and lower sections together for easy rotation of the base unit relative to the support surface.

Figure 1E:
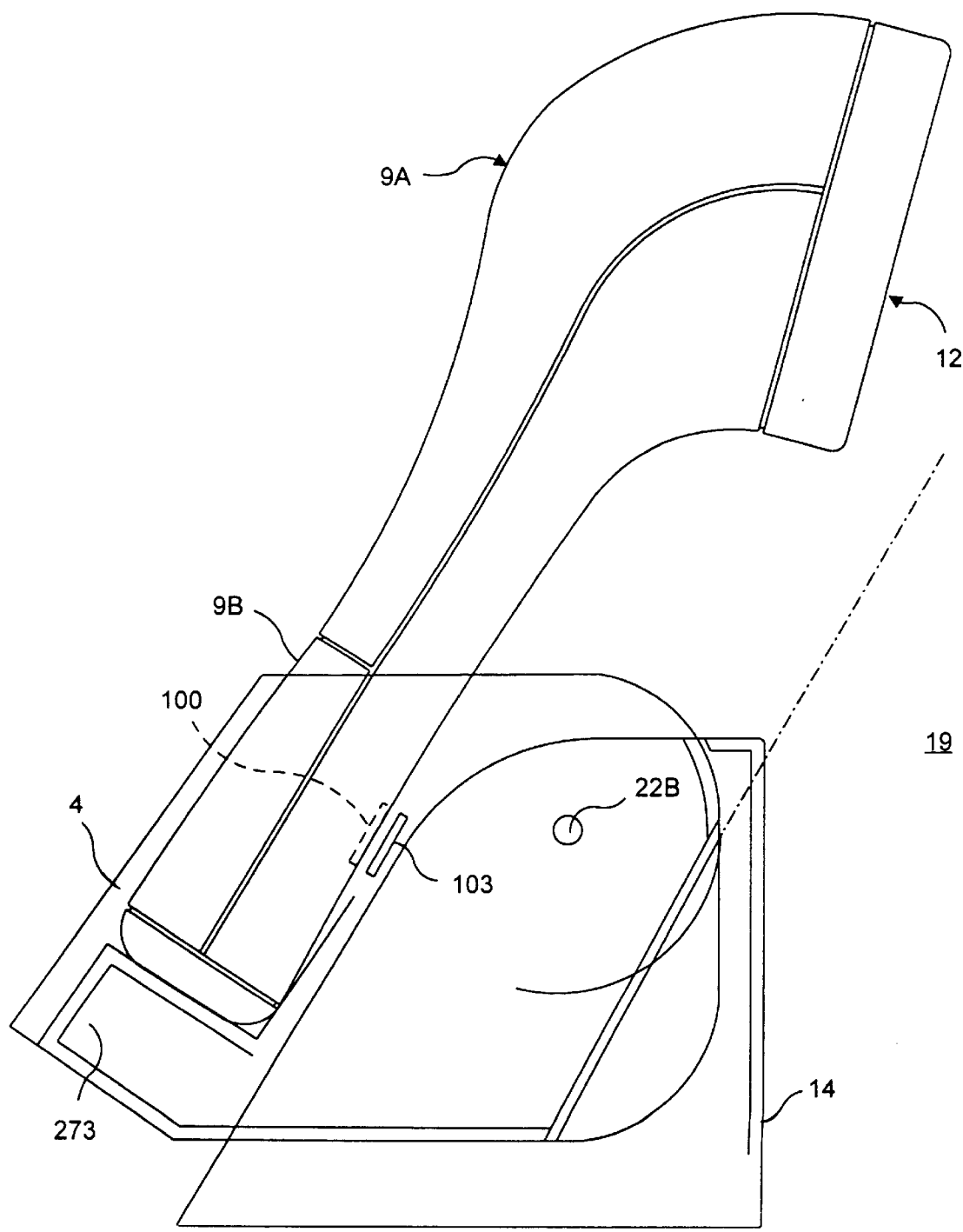
FIG. 1E is an elevated side view of the illustrative embodiment of the automatic bar code symbol reading device hereof, shown supported within the scanner support stand portion of its matching base unit, arranged for automatic hands-free operation in a first scanning position.
Figure 1F:
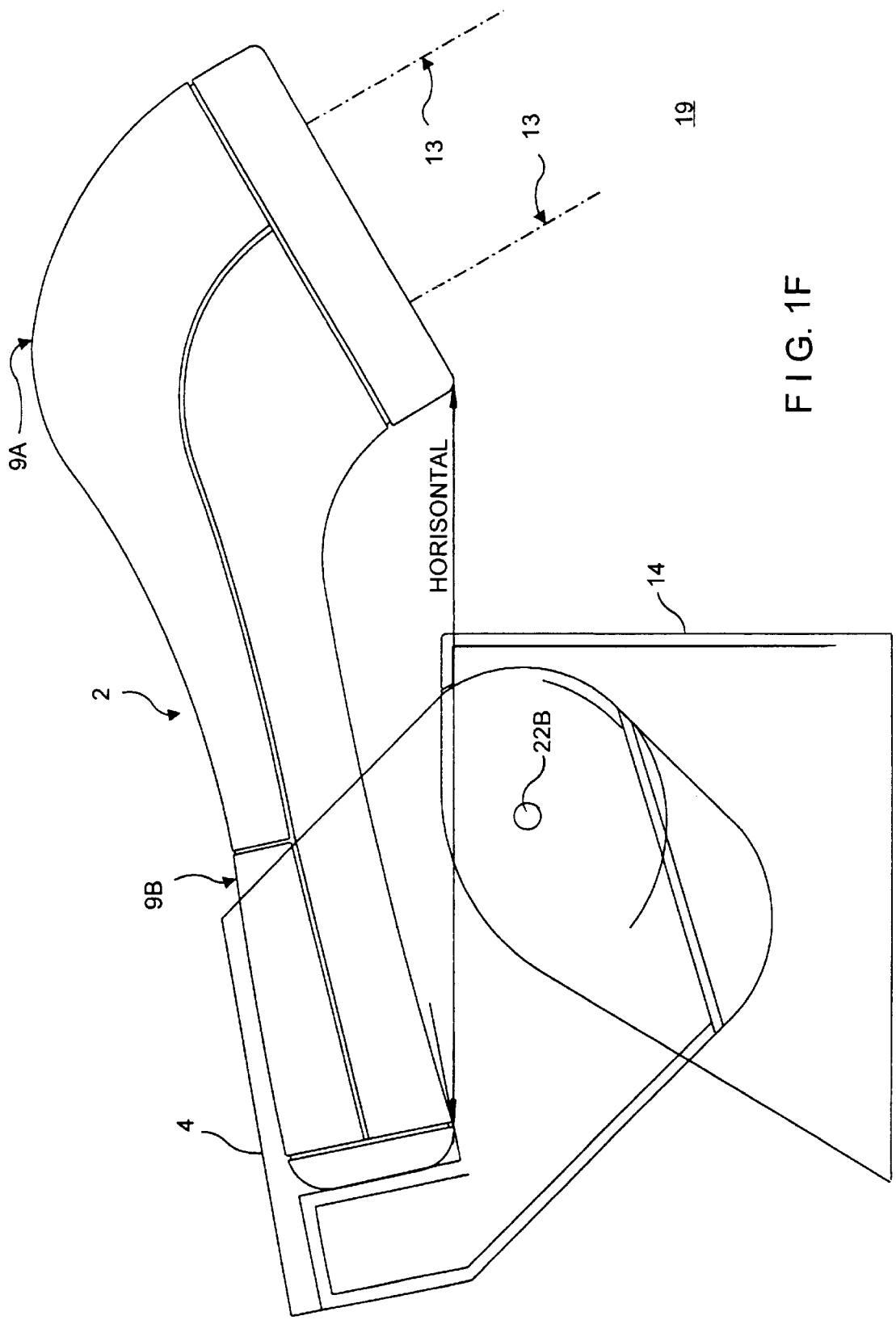

In FIGS. 1E and 1F, the automatic bar code symbol reading system of the present invention is arranged in two extreme scanning configurations during the automatic hands-free mode of system operation. In these different scanning configurations, the stand portion of the base unit is arranged differently with respect to the base portion of the base unit. In FIG. 1E, the stand portion of the base unit is shown supporting the hand-supportable projection scanning device hereof so that its narrowly-confined 3-D scanning volume 13 is projected in a direction slightly off-parallel to the counter surface upon which the base unit is a supported. In this hands-free scanning configuration, code symbols on large objects can be easily scanned by simply presenting the code symbol to the narrowly-confined scanning volume 13 projected, along the "pointing direction" (i.e. longitudinal axis) of the head portion of the scanner housing. In FIG. 1F, the stand portion of the base unit is shown supporting the hand-supportable projection scanning device hereof so that its scanning volume is projected downwardly, in a direction passing through the counter surface upon which the base unit is supported. In this hands-free scanning configuration, code symbols on small objects can be easily scanned by simply presenting to the code symbol to the narrowly-confined scanning volume 13 projected beneath the head portion of the scanner housing.

As illustrated in FIGS. 2A through 3B, the head portion 9A of the hand-supportable housing has a light transmission aperture 12A formed in the front portion thereof. As shown, the light transmission window 12 is mounted over the entire light transmission aperture. In the preferred embodiment, the spectral transmission characteristics of the light transmission window are such that all wavelengths greater (i.e. longer) than slightly less than 670 nm (e.g. longer than 665 nm) are permitted to exit and enter the interior volume of the housing with minimum attenuation. As a result of such characteristics, the visible laser line at 670 nanometers and the infra-red (IR) spectral line at 870 nm (produced from the object sensing circuitry hereof) are allowed to propagated through the transmission window, out of the head portion of the housing, reflect from an object/bar code surface, and return through the transmission window. Notably, all other surfaces of the handsupportable housing are opaque to electromagnetic radiation in the visible band.

Figures 2A, 2B:
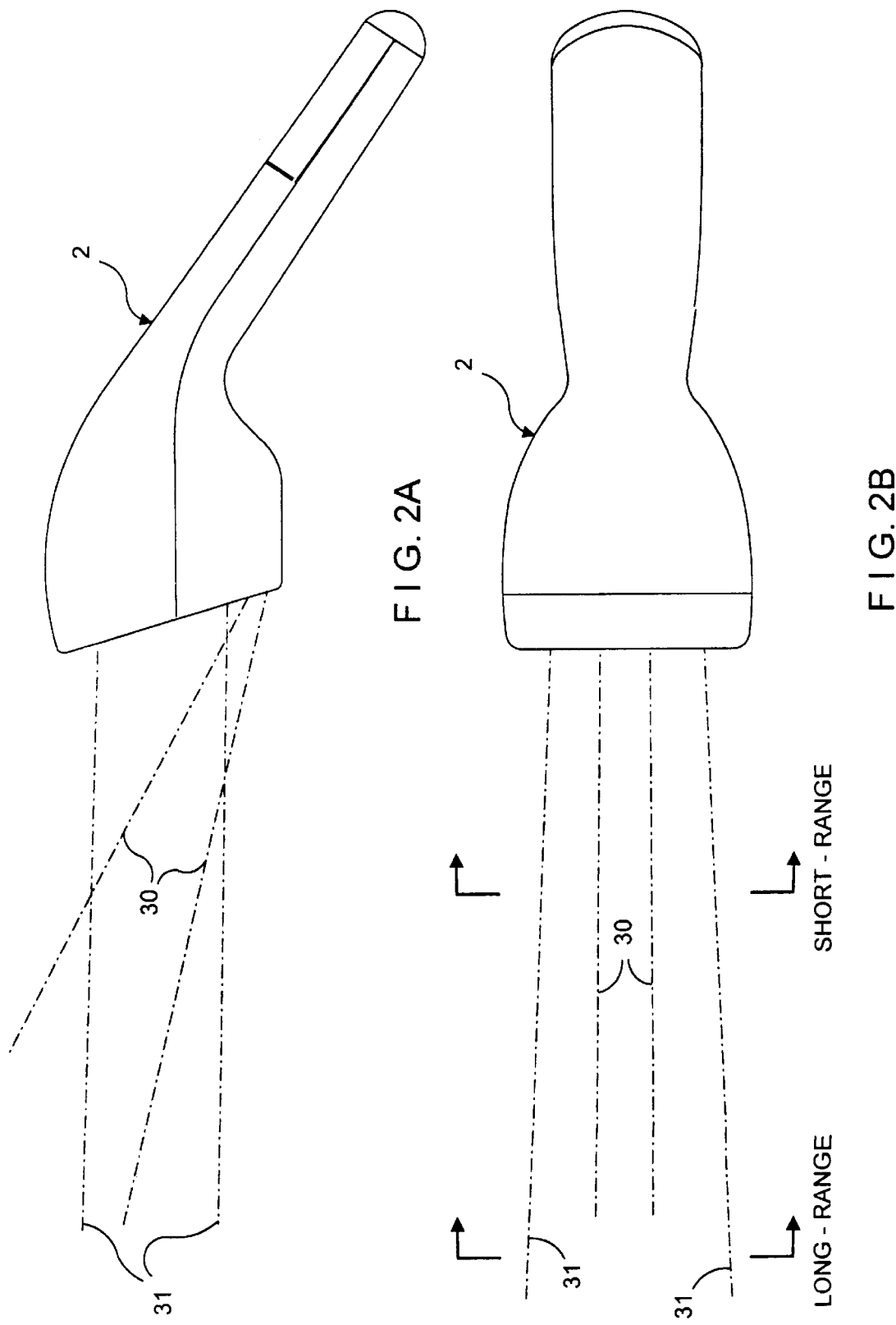
FIG. 2A is an elevated side view of the illustrative embodiment of the automatic bar code symbol reading device of the present invention, illustrating the spatial relationship between the object detection and scan fields of the device, and the long and short-ranges of programmed object detection, bar code presence detection, and bar code symbol reading.
FIG. 2B is a plan view of the automatic bar code symbol reading device taken along line 2A—2A of FIG. 2.

As illustrated in FIGS. 2, and 2A, in particular, the bar code symbol reading device 2 generates from its laser scanning platform 10, two different types of fields external to its hand-supportable housing. As explained below, these fields function to carry out a novel bar code symbol reading process according to the principles of the present invention. The first field, referred to as the "object detection field", indicated by broken and dotted lines 30, is provided external to the housing for detecting energy reflected off an object (bearing a bar code symbol) located in the object detection field. As shown in FIGS. 2A and 2B, the second field 31, referred to as the "scan field" or "3-D scan field" (i.e. narrowly-confined scanning volume 13), has a multiplicity of laser beam scanning planes contained therewithin projected external to the head portion of the housing. The function of the scanning volume (i.e. 3-D scan field) is to scan a bar code symbol on an object automatically detected in the object detection field. In the preferred embodiment, bar code symbol scanning is achieved using a scanned visible laser beam which, after reflecting off the bar code symbol in the scanning volume 13, produces laser scan data that is collected for the purpose of automatically detecting the bar code symbol and subsequently reading (i.e., scanning and decoding) the same.

In general, detected energy reflected from an object during object detection can be optical radiation or acoustical energy, either sensible or non-sensible by the user, and may be either generated from the automatic bar code reading device or an external ambient source. However, as will be described in greater detail hereinafter, the provision of such energy is preferably achieved by transmitting a wide beam of pulsed infrared (IR) light away from transmission aperture 11, in a direction substantially parallel to longitudinal axis 16 of the hand-supportable housing. In the preferred embodiment, the object detection field, from which such reflected energy is collected, is designed to have a narrowly diverging pencil-like geometry of three-dimensional volumetric expanse, which is spatially coincident with at least a portion of the transmitted infrared light beam. This feature of the present invention ensures that an object residing within the object detection field will be illuminated by the infrared light beam, and that infrared light reflected therefrom will be directed generally towards the transmission aperture of the housing where it can be automatically detected to indicate the presence of the object within the object detection field. In response to object presence detection, a visible laser beam is automatically generated within the interior of the bar code symbol reading device, projected through the light transmission aperture of the housing and repeatedly scanned across the scanning volume, within which at least a portion of the detected object lies. At least a portion of the scanned laser light beam will be scattered and reflected if the object and directed back towards and through light transmissive window 11 for collection and detection within the interior of the bar code symbol reading device, and subsequently processed in a manner which will be described in detail hereinafter.

To ensure that the user can quickly align the visible laser beam with the bar code symbol on the detected object, the object detection field of the preferred embodiment is designed to spatially encompass a significant portion of the 3-D scanning volume along the operative scanning range of the device, as illustrated in FIGS. 2A and 2B, for the first illustrative embodiment of the present invention. This structural feature of the present invention improves the laser beam pointing efficiency of the device during the automatic bar code symbol reading process.

Figure 3A:
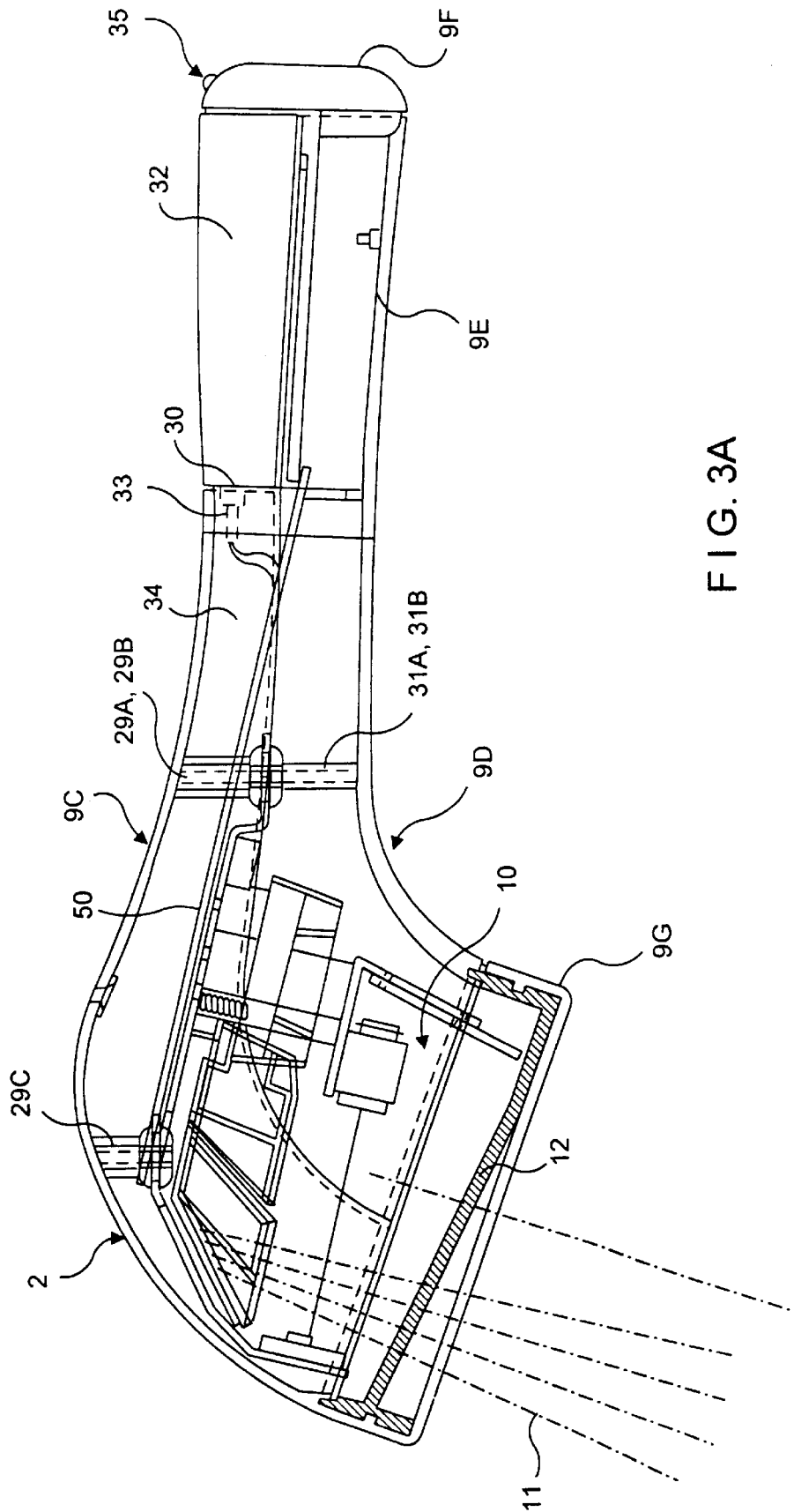
FIG. 3A is an elevated, cross-sectional side view of the automatic bar code symbol reading device of the present invention, taken along its longitudinal axis, showing the various components contained therein.

As best shown in FIGS. 3A and 3B, the laser scanning platform (i.e., laser scanning engine) 10 of the present invention is mounted within the head portion of the hand-supportable housing by way of a three-point shock-absorbing mounting mechanism, which will be described in greater detail hereinbelow. In the illustrative embodiment, the hand-supportable housing is realized as a five-piece split-housing construction comprising: a first housing portion 9C carrying three spaced-apart mounting posts 29A, 29B and 29C, and providing a battery storage bay 30 for storage of a (rechargeable) battery supply unit 32; a second housing half 9D providing posts 31A and 31B which engage with support posts 29A and 29B when the first and second housing halves are brought together; a battery cover 9E for placement over the battery storage bay 30; a housing end cap 9F for placement over the ends of the first and second housing halves; and a housing bumper 9G for supporting the light transmission window 12 and holding securely together the front ends of the first and second housing halves when the subcomponents of the housing are assembled together. Provided within the battery storage bay, is an electrical socket 33 designed to receive rechargeable battery 32 when it is installed within the bay when the bay cover 9E is removed. An electrical wire harness 34 is used to connect the battery socket 33 to a printed circuit (PC) board 50 supported upon the laser scanning platform 10, carrying digital scan data processing and control circuitry. Apertures 35A and 35B are formed in the end portion of the housing handle to allow electrodes 51A and 51B on the battery 32 to establish electrical contact with charging electrodes 52A and 52B provided within the support bay 60 of the stand portion of the base unit when the scanning device is operated in its hands-free mode of operation. Preferably, the above-described housing subcomponents are made from a rugged, lightweight plastic material using injection-molding techniques well known in the art.

As will be described in greater detail hereinafter, the data packet transmission circuit of copending application Ser. No. 08/292,237, now U.S. Pat. No. 5,808,285 is realized on PC board 50, along with the microprocessor used to implement symbol decoding, data formatting and system control functions. Electrical power supplied from rechargeable battery 32 is provided to the digital signals processing/control board 50 by way of flexible wire harness 34. As shown, a transmitting antenna 53 is operably connected to the data packet transmission circuit on the digital signal processing board and is mounted within hand-supportable housing 9 for transmission of a data packet modulated RF carrier signal. The structure and the functionalities of the automatic bar code symbol reading system hereof will be described in greater detail hereinafter with reference to FIGS. 8 to 14.

In FIG. 4, the laser scanning platform 10 is shown removed from its housing. As shown, the laser scanning platform comprises an assembly of subcomponents assembled upon an optical bench 34 with respect to a central longitudinal reference plane 35 referenced in Fogs. SA through 5B, in particular. This subcomponent assembly comprises: a scanning polygon 36 having four light reflective surfaces 36A, 36B, 36C and 36D, each disposed at an tilt angle a with respect to the rotational axis of the polygon; an electrical motor 37 mounted on the optical bench, and having a rotable shaft on which polygon 36 is mounted for rotationable movement therewith; an array of stationary mirrors 38A, 38B, 38C, 38D and 38E fixedly mounted with respect to the optical bench; a laser beam production module 39, fixedly mounted above the rotating polygon, for producing a laser beam having a circularized beam cross-section, and essentially free of astigmatism along its length of propagation; an analog signal processing board 40, fixedly mounted over the rotatable polygon, and carrying a photo-detector 41 for detecting reflected laser light and producing analog scan data signals, and analog signal processing control circuits 42 for performing various functions, including analog scan data signal processing; a light collecting mirror 43, disposed at a height above the central stationary mirror 38C, for collecting light rays reflected off the rotating polygon and focusing the same onto the photodetector on the analog board; and a beam directing surface 44, realized as a flat mirror mounted on the light collecting mirror 38C, for directing the laser beam from the laser beam production module to the rotating polygon disposed therebeneath. As shown, these subcomponents are mounted relative to the optical bench 34 according to the Specifications set forth in FIGS. 6A through 6B.

Figure 5B:
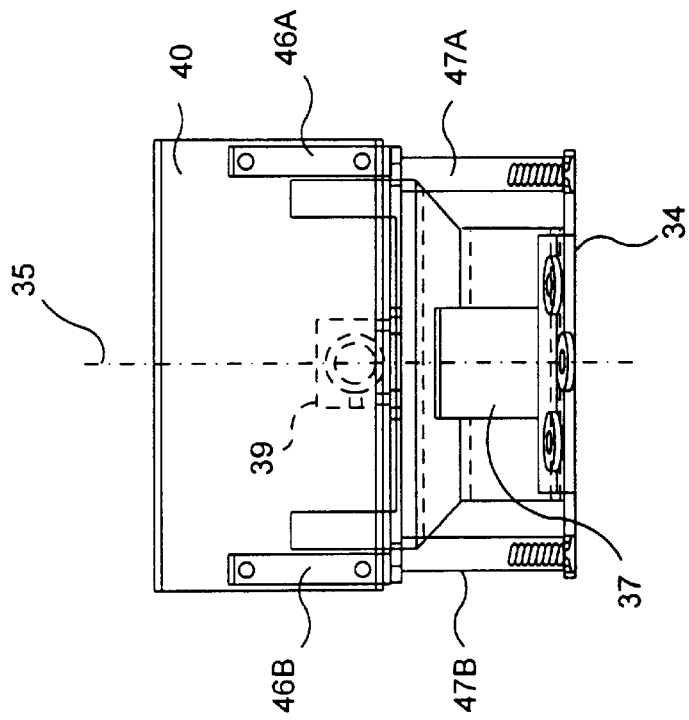
FIG. 5B is a view of the laser scanning platform of the present invention taken along line 5B—5B of FIG. 4.
Figure 5A:
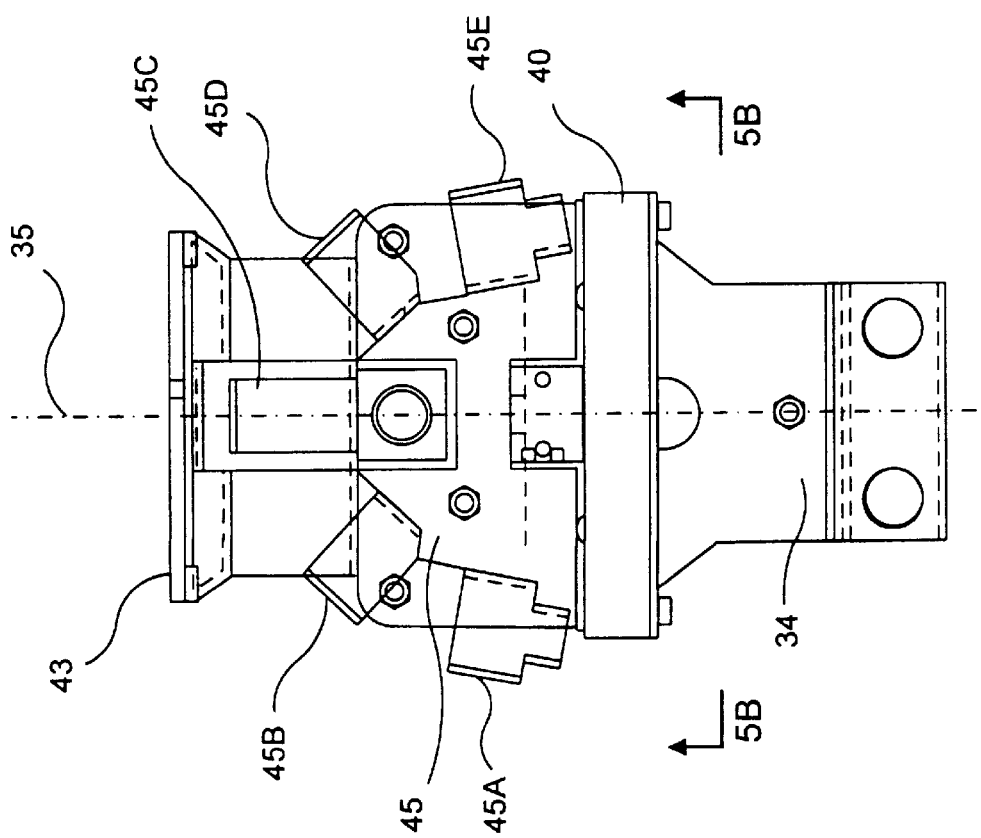
FIG. 5A is a plan view of the optical bench of the laser scanning platform of FIG. 4, shown with the stationary array of mirrors, rotating polygonal mirror and motor removed therefrom for illustrative purposes.

In FIGS. 5A through 5D, the subcomponents of the laser scanning platform are shown in greater detail. In particular, optical bench 34 is shown in FIG. 5A with the scanning motor 37 and, stationary mirror elements 38A through 38E removed for illustration purposes. As shown, stationary mirror brackets 45 is mounted upon the optical bench 34 and has five mirror support elements 45A through 45B, disposed beneath the locations of their respective mirrors 38A, 38B, 38C, 38D and 38E. As shown in FIG. 5B, the analog signal processing board 40 is disposed above the scanning polygon 36 and extends at an acute angle with respect to the plane of the optical bench. The analog signal processing board 40 is supported in this position and orientation by a pair of support bracket 46A and 46B. Support brackets 46A and 46B, in turn, are supported by a pair of support posts 47A and 47B mounted to the middle portion of the optical bench 34, as shown in FIGS. 5A and 5B. As illustrated in FIG. 4, the position of these support posts are slightly forward of the rotational axis of the polygon motor.

As best shown in FIG. 5A, the transverse axis of the light collecting mirror 43 is perpendicular to the central reference plane of the optical bench. The stationary light reflective surface (i.e. mirror) 38C also has a transverse axis extending substantially perpendicularly with respect to the central reference plane 34. Stationary light reflective surfaces 38B and 38D are symmetrically disposed on opposite sides of the central reference plane, respectively, and immediately adjacent stationary light reflective surface 38C. Stationary light reflective surfaces (i.e. mirrors) 38A and 38E are symmetrically disposed on opposite sides of the central reference plane, and immediately adjacent stationary light reflective surfaces 38B and 38D, respectively, and adjacent rotating polygon 36.

Figure 5C:
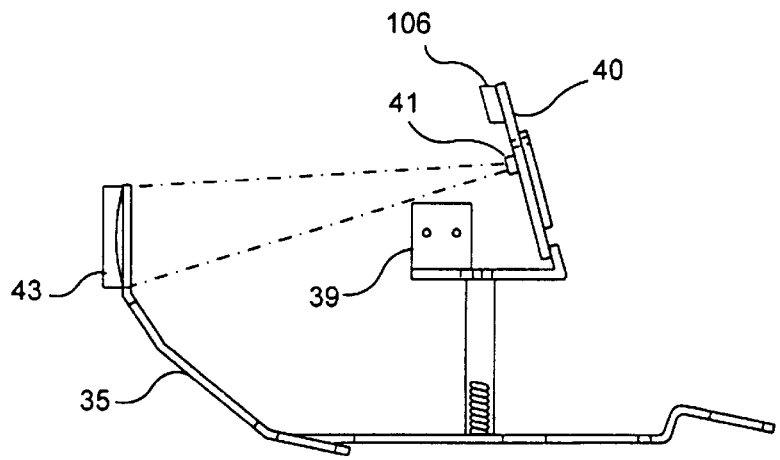
FIG. 5C is an elevated side view of the optical bench of FIG. 5A, shown with the stationary mirror support bracket removed therefrom for illustrative purposes.

As best illustrated in FIG. 5C the angle of declination of the light collecting mirror 43 is selected so that the incident laser beam thereon from the laser beam production module 38 is redirected towards the rotating polygon during laser beam scanning operations. The focal length of the light collecting mirror 43 is, selected so that collected light rays from the mirror are focused upon the photodetector 41, centrally mounted upon the analog signal processing board 40. In the illustrative embodiment, light focusing mirror 43 is realized from ground-polished glass, or molded plastic, coated with a mirror-finish by vapor deposition.

Figure 5D:
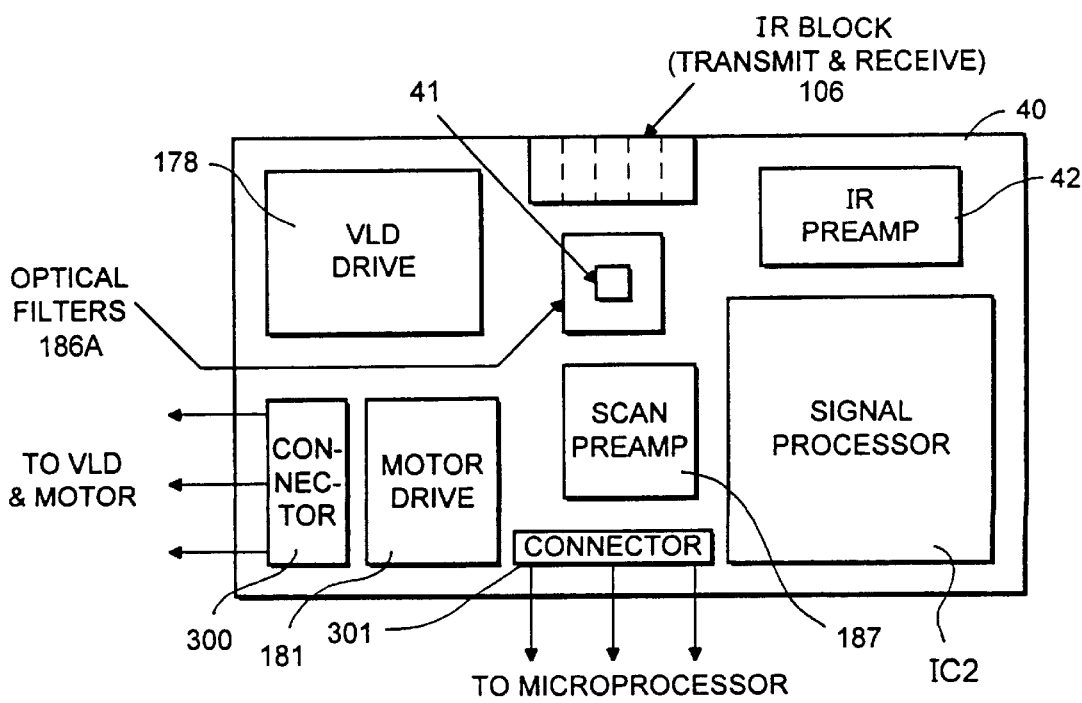
FIG. 5D is schematic diagram illustrating the physical layout of components on the analog signal processing board supported on the optical bench of the laser scanning platform of FIG. 4.

As shown in FIG. 5C, the photodetector 41 and light collecting mirror 43 are aligned along a common optical axis which is disposed within the central longitudinal plane. As shown in FIG. 5D, the photodetector 41 is mounted on the analog signal processing board 40 along with signal processing circuits and signal connector elements, namely: optical filters 186A; visible laser diode drive circuitry 178; motor drive circuitry 181; IR preamp circuitry 187; IR transmit and receive circuitry 106; signal processing circuitry IC2; scan signal preamplification circuitry 187; microprocessor port connector 300; and VLD/motor port connector 301. The function of such components will be described in greater detail hereinafter.

The laser beam production module 39 of the laser scanning platform hereof may be realized in a variety of ways. Preferably, each embodiment thereof comprises a visible laser diode for producing a visible laser beam, and associated optics for circularizing the laser beam and eliminating astigmatism therefrom along its direction of propagation. In the illustrative embodiment, the associated optics comprises an aspheric collimating lens, a beam circularizing prism, and a holographically formed light diffractive grating configured in such a manner that the above-described functions are realized during laser beam production. The manner in which such a laser beam production module can be constructed without the use of aperture stops is taught in copending application Ser. No. 08/573,949, now abandoned incorporated herein by reference.

The particular parameters used to configure the optical components of the laser scanning module are schematically represented in FIGS. 6A1 through 6D. In FIGS. 6A1 and 6A2, a geometrical optics model is provided for the illustrative embodiment of the laser beam scanning platform of the present invention. Within this geometrical optics model, stationary mirror surface 38A through 38E are designated by surface parameters S1 through S5, respectively. Each of these mirror surfaces is located about the central longitudinal plane 35 of the system, which functions as a reference plane. In the illustrative embodiment, the distance between the rotational axis of the polygon and the base of the central mirror surfaces S3 is 34 millimeters in the, illustrative embodiment, whereas the base-to-base distance between mirror surfaces S1 and S5 is about 35 millimeters.

As shown in the geometrical optics model, the angled of inclination of the four mirrored surfaces on the polygon 36A, 36B, 36C, 36D are set forth in the Table of FIG. 6B. The angle of elevation f (i.e. bend) of each of the stationary mirrors 38A, 38B, 38C, 38D and 38E are listed in Table of FIG. 6A1. As shown in FIG. 6B, the angle of inclination of the stationary mirrors is references with respect to the plane of the optical bench. As shown in FIG. 6A1, the angle of twist a for each stationary mirror is referenced relative to the central longitudinal plane 35. The twist angle for the stationary mirrors are set forth in the Table of FIG. 6A1. Notably, as central stationary mirror S3 is disposed transversely relative to the central longitudinal plane, the twist angle for this stationary mirror is 90°. The laterally disposed stationary mirrors S2 and S4 have the same twist angle of 43.75°, whereas stationary mirrors S1 and S5 have the same twist angles of 40.5°.

Figure 7A:
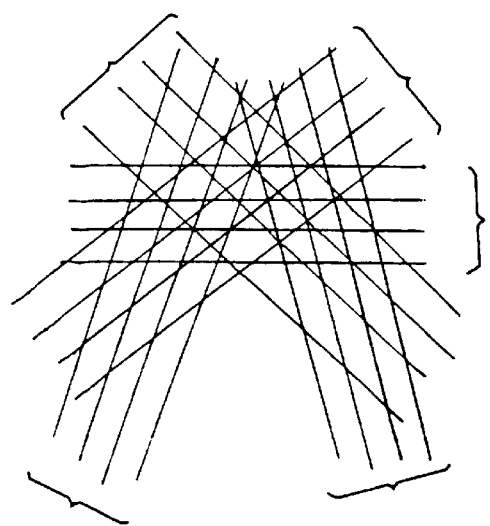
FIGS. 7A and 7B are cross-sectional views of the 3-D laser scanning volume of the illustrative embodiment, taken parallel to the light transmissive window at about 1.0" and 5.0" therefrom.
Figure 7B:
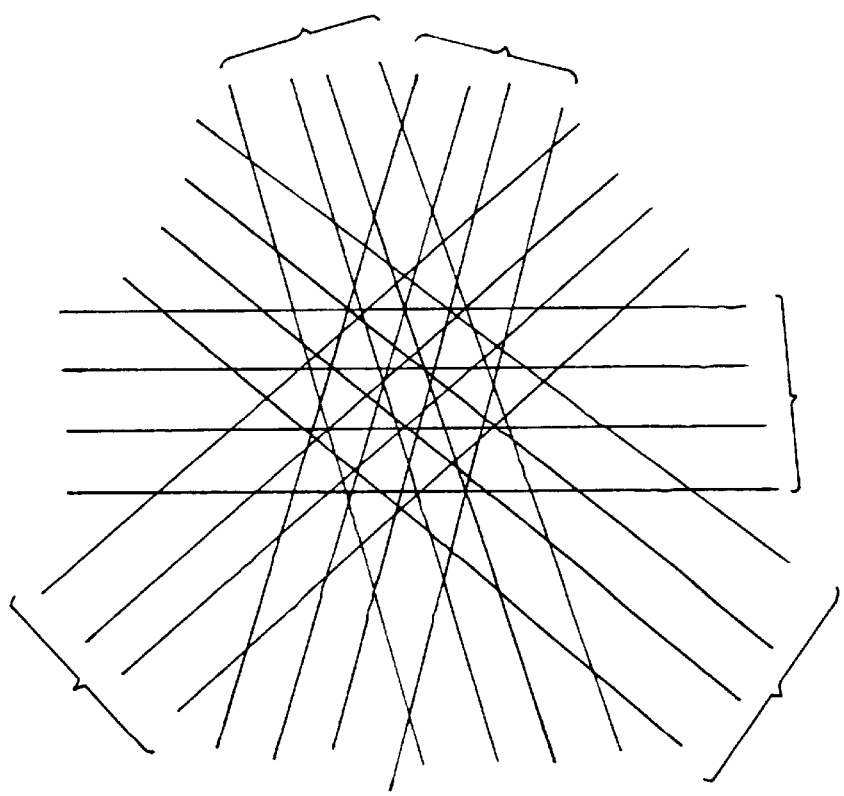

The heightwise and widthwise dimensions of the stationary reflective surfaces, in part, determine the length of the scanlines within the scan field. These dimensions are indicated in FIG. 6C for the illustrative embodiment. Notably, the perimetrical dimensions of these stationary mirrors are irregular in order to form a tightly-nested stationary mirror array arranged about the rotating polygon 36. The exact surface dimensions are indicated in FIG. 6C. The heightwise and widthwise dimensions of the mirrors on the rotating polygon are indicated in FIG. GD. When constructed in accordance with the Specifications disclosed herein, the laser scanning platform of the illustrative embodiment will produce a highly collimated set of scanning planes which extend from the light transmission window and intersect about the projection axis 17 to form a highly collimated scanning pattern within a narrowly-confined 3-D scanning volume thereabout. Two-dimensional cross-section characteristics of the resulting laser scanning pattern at about 1.5 and 6 inches from the transmission window are shown in FIGS. 7A and 7B.

When assembled and configured as described above, the laser scanning platform 10 is mounted with the upper and lower halves of the hand-supportable housing 9A and 9B. Mounting is achieved by way of resiliently securing shock-mounting support posts 29A, 29B and 29C to corresponding mounting holes formed within the optical bench 35 using rubber grommets and screws. As shown in FIG. 7, the assembled laser scanning platform (i.e. engine) is installed within the housing in a manner described above. As shown, PC board 5G is mounted to the underside of the plastic optical bench by way of mechanical fasteners known in the art. The function of PC board 50 is provide substrate upon which the decode/control processor, RF data packet transmission circuitry and power. distribution circuitry of the laser scanning device hereof are realized. In order that the shock-absorbing mounting system can operate properly, it is important that sufficient clearance is provided between the outermost extensions of the scanning platform tand the interior wall surface of upper portion of the housing. In this way, the scanning platform is permitted to undergo gross displacements in the directions of the dominant oscillatory modes of system when the device is dropped onto the floor, knocked into solid objects and the like under normal or otherwise expected operating environments.

Having described the physical construction of the laser scanning engine 10 of the present invention, it is appropriate at this juncture to describe in greater detail the manner in which the laser scanning pattern is produced from the laser scanning platform hereof.

Upon detection of an object within the object detection field 30, a laser beam is produced from the laser beam production module 39 and is directed towards beam directing surface 44 mounted on the light collecting mirror 43. The laser beam reflects from the beam directing surface 44 towards the mirrored facets on the rotating scanning polygon 36. As the polygon spins, the incident laser beam reflects off the rotating mirrors 36A through 36D and sweeps the laser beam about its rotational axis along a plurality of different paths which intersect the stationary array of mirrors 38A through 38E on the optical bench. During each revolution of the scanning polygon, the laser beam reflects off the rotating mirrors and therewhile is repeatedly swept across the array of stationary mirrors thereby producing first, second, third, fourth and fifth groups of plural scan lines, respectively. These plural groups of scanlines shown in FIGS. 7A and 7B are projected out through the light transmission window and intersect about the projection axis 17 extending from the light transmission window, and within the narrowly confined scanning volume 13. In the illustrative embodiment, the intersection of the laser scanning planes extends from adjacent (e.g. about 9.5" from) the light transmission window to at least about 10.0 inches therefrom so as to produce a highly collimated projected scanning pattern within the narrowly confined 3-D scanning volume. Within this 3-D scanning volume, a bar code, symbol can be scanned omnidirectionally, while preventing unintentional scanning of code symbols on objects located outsider thereof.

As illustrated in the cross-sectional diagrams of FIGS. 7A and 7B, there exists a particular relationship among the scanlines of the laser scanning pattern of the illustrative embodiment. In particular, each scan line in each group of scan lines is substantially parallel to each other scan line in that group of scan lines. As a result, when the code symbol is presented to the highly collimated scanning pattern projected within narrowly confined scanning field, the code symbol is automatically scanned therewithin independent of the orientation of the code symbol within the scanning field (i.e. scanning volume). At least a portion of the laser light reflected from the scanned code symbol is directed through the light transmission window, reflected off the stationary light reflective surfaces, reflected off the rotating mirrors, collected by the light focusing mirror, and received by the photodetector 41, whereupon an electrical signal is produced for use in decode signal processing. The details of such signal processing operations, and the preferred means for achieving the same, can be best understood with a detailed description of the scan and control data processing circuitry embodied with the laser scanning device of the present invention.

Figure 8:
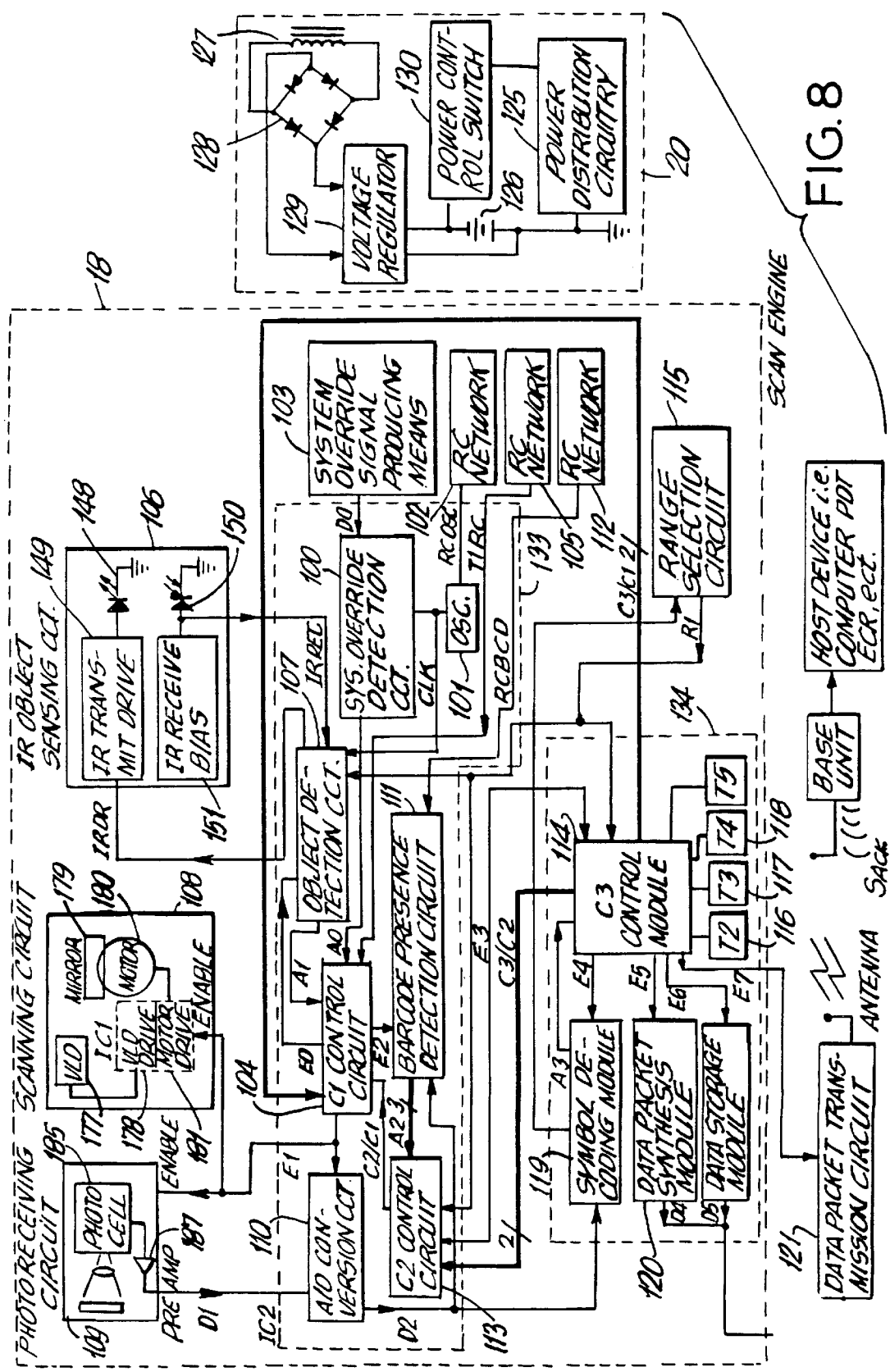
FIG. 8 is a system block functional diagram of the automatic bar code symbol reading system of the present invention, illustrating the principal components integrated with the control (sub)-system thereof.

As shown in FIG. 8, the automatic bar code symbol reading system of the present invention comprises the automatic laser scanning device of the illustrative embodiment in combination with a number of system components. These additional system components include: a primary oscillator circuit 101 for producing a primary clock signal CLK for use by the object detection circuit 107; a first RC timing network 102 for setting the oscillation frequency, of the primary oscillator circuit; first control means 104, realized as a first control circuit $C_1$, for performing localized system control functions; a second RC timing network 105 for setting a timer $T_1$ in control circuit $C_1$; means (e.g., an object sensing circuit 106 and an object detection circuit 107) for producing a first activation control signal $A_1=1$ upon the detection of an object bearing a bar code in at least a portion of the object detection field; a laser beam scanning mechanism 108 for producing and scanning a visible laser beam across the bar code symbol on the detected object; photoreceiving circuit 109 for detecting laser light reflected off the scanned bar code symbol and producing an electrical signal $D_1$ indicative of the detected intensity; a analog-to-digital (A/D) conversion circuit 110 for converting analog scan data signal $D_1$ into a corresponding digital scan data signal $D_2$; a bar code presence detection circuit 111 for processing digital scan data signal $D_2$ in order to automatically detect the digital data pattern of a bar code symbol on the detected object and produce control activation signal $A_2=1$; a third RC timing network 112 for setting a timer $T_{BCD}$ in the bar code symbol detection circuit; second control means 113, realized as a second control circuit $C_2$, for performing local system control operations in response to the detection of the bar code symbol; third control means 114, realized as third control module $C_3$; a range selection, circuit 115 for supplying range selection signals to the object detection circuit; second control circuit $C_2$ and third control module $C_3$; timers $T_2$, $T_3$, and $T_4$ identified by reference numerals 116, 117 and 118, respectively; a symbol decoding module 119 for processing digital scan data signal $D_2$ so as to determine the data represented by the detected bar code symbol, generate symbol character data representative thereof, and produce activation control signal $A_3$ for use by third control module $C_3$; a data packet, synthesis module 120 for synthesizing a group of formatted data packets for transmission to its mated base unit; and a data packet transmission circuit 121 for transmitting the group of data packets synthesized by the data packet synthesis module. As will be described in greater detail hereinafter, second control circuit $C_2$ is capable of "overriding" (i.e., inhibit and/or enable) first control circuit $C_1$, whereas third control module $C_3$ is capable of overriding first and second control circuits $C_1$ and $C_2$, respectively. As shown in FIG. 8, such control override functions are carried out by the generation of control override signals (i.e., $C_2/C_1$, $C_3/C_2$ and $C_3/C_1$) transmitted between respective control structures. Owing to the unique architecture of the control subsystem hereof, the automatic bar code symbol reading device of the present invention is capable of versatile performance and ultra-low power operation. The structure, function and advantages of this control subsystem architecture will become apparent hereinafter.

Figure 8A:
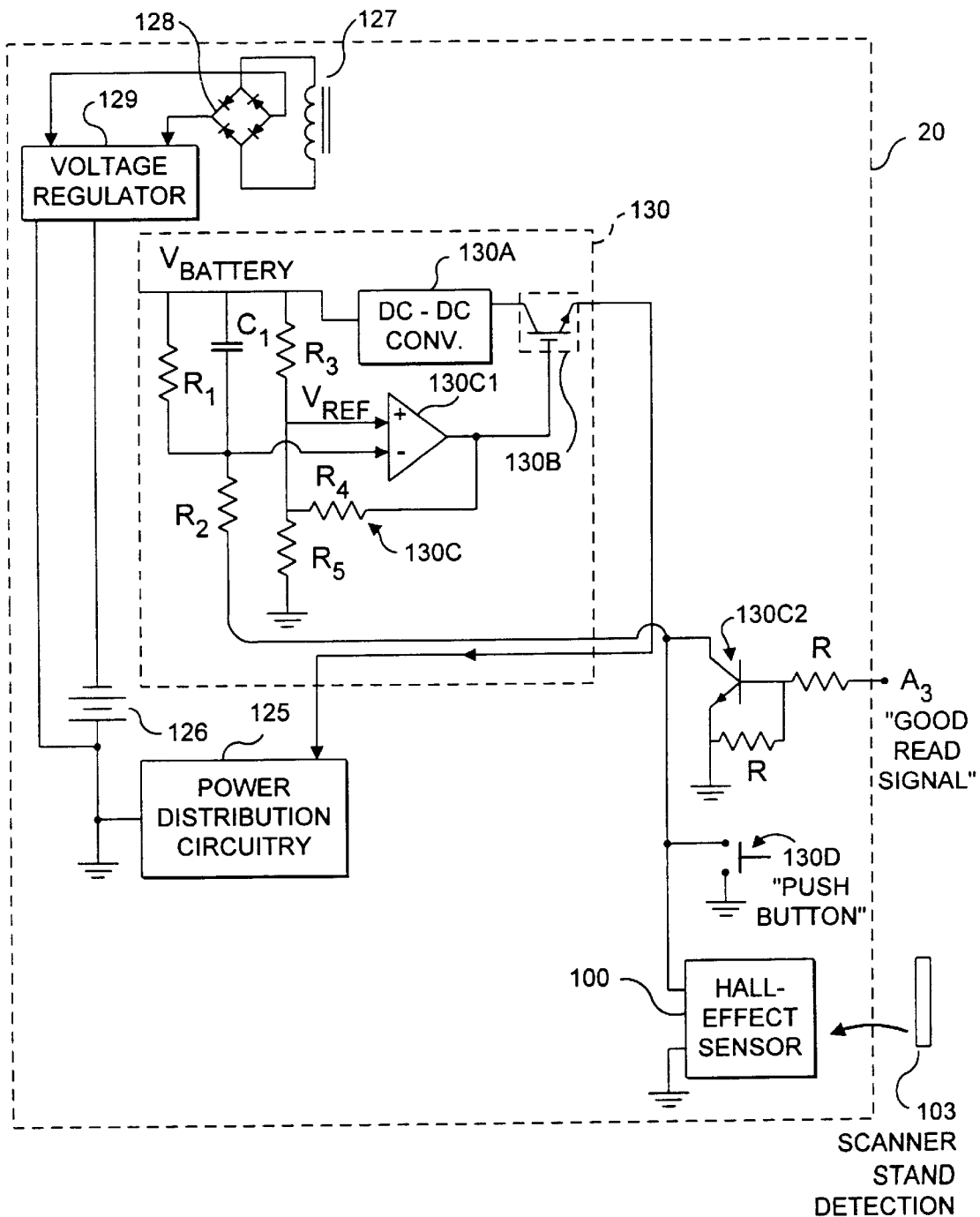
FIG. 8A is a schematic diagram of the automatic power supply unit aboard the automatic bar code symbol reading device of the present invention.

As shown in the schematic diagram of FIG. 8A, battery: power supply unit 20 contained within the housing of the code symbol reading device provides electrical power to the components therewithin in accordance with a programmed mode of intelligent operation. In the illustrative embodiment, battery power supply unit 20 comprises a power supply distribution circuit 125, replaceable or rechargeable batteries 126, and an automatic power control circuit 130. In the illustrative embodiment, where; rechargeable batteries are employed, the power supply circuit 20 further includes a secondary inductive coil 127, bridge rectifier 128 and voltage regulation circuit 129. Preferably, all of these, subcomponents are contained within the hand-supportable housing of the device, and are configured together as shown in FIG. 8A.

As illustrated in FIG. 8A, the function of second inductive coil 128 is to establish an electromagnetic coupling with the primary inductive coil contained in the base unit associated with the bar code reading device whenever the device is supported if in the recharging portion of the base unit. In this configuration, electrical power is inductively transferred from the primary inductive coil in the base unit to secondary inductive coil 127, rectified by bridge rectifier 128, and filtered by voltage regulation circuit 129 to provide a regulated DC power supply for recharging rechargeable batteries 126.

As shown in FIG. 8A, automatic power control circuit 130 is connected in series between rechargeable battery 126 and power distribution circuit 125. The function of automatic power control circuit 130 is to automatic control (i.e. manage) the availability of battery power to electrically-active components within the bar code symbol reading device when the device is operated in its hands-on mode of operation (i.e. removed from the scanner support stand) under a predefined set of operating conditions. Notably while power distribution circuit 125 distributes electrical power throughout the bar code symbol reading device by way of a power distribution bus, automatic power control circuit 130 globally enables consumption of electrical power (i.e. the product of voltage and direct current) by the system components when activated.

As shown in FIG. 8A, the automatic power control circuit 130 comprises a number of subcomponents, namely: a DC-to-DC voltage converter 130A; a power commutation switch 130B; and a resettable timer circuit 130C. The function of the DC-to-DC voltage converter 103A is to convert the voltage from battery power source 126 to +5 Volts, whereas the function of the power commutation switch 130B is to selectively commute electrical power from the DC-to-DC converter 130A to the input port of the power distribution circuit 125. The function of the resettable timer circuit 130C is to control the power commutation circuit so that battery power is provided to the power distribution circuit 125 in a power conserving manner without compromising the performance of the bar code symbol reading system in its various modes of operation.

In the illustrative embodiment, DC-to-DC converter 130A is realized by configuring a low-voltage input, adjustable output step-up DC-DC converter (e.g. such as the MAX777 IC chip by SLIM Integrated Products) with an inductor (e.g. 22.0 microHenries) and two capacitors, to produce a 5.0 Volt output voltage for use in the bar code symbol reading device. As shown, resettable timer circuit 130C is realized by configuring a comparator circuit 130C1 (e.g. as provided for example in the LM2903 IC chip by National Semiconductor) with external resistors R1, R2, R3, R4 and R5 and charging capacitor C1. The function of the resistors R3 and R5 is to provide to one inputs of the comparator a positive reference voltage (i.e. Vref) which is close in magnitude to the battery voltage Vbattery, with resistor R4 being connected to the output of the comparator for hysteresis. The power control switch 130B is realized by N-channel field effect transistor (FET), wherein the source terminal is connected to the output port of the DC-to-DC converter 130A, the drain terminal is connector is connected to the input port of the power distribution circuitry 125, and the gate terminal is connected to the output port of the comparator 130C1.

In the illustrative embodiment, there are three different power switching events which will reset the resettable timer circuit 130C, cause the comparator thereof to produce a high output level and drive the N-channel FET into conduction. The first power switching event comprises manually depressing power reset button 130D mounted on the exterior of the scanner housing. The second power switching event comprises placing the handle portion of the scanner housing within the recess of the scanner support stand hereof, whereby Hall-effect sensor 100 within the handle of the housing detects magnetic flux produced from permanent magnet 103 within the scanner support stand recess, as shown in FIG. 1E. The third power switching event comprises successfully reading a bar code symbol and producing activation signal A3=1.

In order that such power switching events will effectively reset the resettable timer circuit 130C, a number of electrical devices are connected to input port of the resettable timer circuit 130C, effectively realized by resistor R2. In particular, the "good read" activation signal A3=1 produced by symbol decoding module 119 is provided to the base of a NPN transistor 130C2, which has its collector terminal connected to one end of resistor R2 and its emitter terminal connected to electrical ground. As shown, one terminal of manually depressible power reset button 130D (e.g. realized as a spring-biased push-type button switch) is connected to the same end of resistor R2, to which the collector of NPN transistor 130C2 is connected, while the other terminal of power set button 130D is connected to electrical ground. Also, one terminal of stand detector (e.g. Hall-effect sensor 100) is connected to the same end of resistor R2, to which the collector of NPN transistor 130C2 is connected, while the other terminal of the Hall-effect sensor 100 is connected to electrical ground, as shown in FIG. 8A.

Battery supply 126 aboard the scanning device is automatically charged to its normal output voltage (i.e. Vbattery) by way of battery recharging apparatus 127, 128 and 129. A predetermined time duration ΔT (e.g. 1 minute, preferably 5 minutes) after the occurrence of a power switching event, power supply unit 20 attains its steady-state condition. At this state, capacitor C1 charges through resistor R1, to a voltage above Vref. This causes the output voltage of the capacitor 130C1 to drop to a level which disables FET 130B, thereby disabling the supply of battery power to power distribution circuit 125, and ultimately disabling the scanning device. Upon the occurrence of any of the above three "power switching" events described above, capacitor C1 quickly discharges through resistor R2 (i.e. R1>>R1), causing the output voltage of capacitor 130C1 to go to a level which enables FET 130B to supply battery power to the power distribution circuitry 125, and thereby enabling the scanning device for the predetermined time period (e.g. ΔT greater than 1, preferably 5 minutes). This programmed duration of power supply provides a time window ΔT, within which the object detection circuit of the system hereof can automatically detect an object within the object detection field. Such power resetting operation does not, however, initiate or otherwise cause laser scanning or bar code symbol reading operations to commence or cease. Only the introduction of an object into the object detection field (i.e. when the resettable timer circuit 130C has been reset) can initiate or otherwise cause laser scanning or bar code symbol reading operations to commence.

A principal advantage of the power control scheme of the present invention is that it provides automatic power conservation in automatic code symbol reading applications, while minimally impacting upon the diverse modes of automatic operation provided by the system hereof. In particular, provided that the user reads at least one bar code symbol within the predetermined time duration $\Delta T$ programmed into the bar code symbol reading device, there is no need to reset the power control circuit hereof. Also, when the hand-supportable housing of the device is placed (i.e. supported) within the support recess 60 of scanner support portion of the base unit, Hall-effect sensor 103 produces a stand detect signal which continuously causes power control circuit 130 to supply battery power from continuously recharging battery 126, to the power distribution circuit 125, thereby enabling continuous scanner operation in the hands-free mode of operation.

Range selection circuit 115 may include a manual switch externally accessible to the housing, which the user can depress to select long or short-range modes of object detection, bar code presence detection and/or bar code symbol reading. Alternatively, Range Selection Circuit 115 can be activated to a particular range setting by symbol decoding module 119. In this mode of operation, the range setting can be set by decoding a bar code symbol predesignated to activate the long or short range modes of detection, as the case may be.

In the illustrative embodiment of the present invention, primary oscillator circuit 101, object detection circuit 107, first control circuit $C_1$, analog-to-digital conversion circuit 110, bar code symbol detection circuit 111, and second control circuit $C_2$ are all realized on a single Application Specific Integrated Circuit (ASIC) chip 133 using microelectronic circuit fabrication techniques known in the art. In the illustrative embodiment, the ASIC chip and associated circuits for laser scanning and light detection and processing functions are mounted on analog signal processing board 40. Symbol decoding module 119, data packet synthesis module 120, timers $T_2$, $T_3$, $T_4$, and T5 and third control module $C_3$ are realized using a single programmable device, such as a microprocessor having accessible program and buffer memory, and external timing circuitry, collectively depicted by reference numeral 134 in FIG. 8. In the illustrative embodiment, these components and devices are mounted on the PC board 50.

In the illustrative embodiment, when power control switch 130 is in its reset (i.e. POWER ON) state, power from battery power unit 126 is provided to first control circuit $C_1$, priflary, oscillator circuit 101 and IR object sensing circuit 106 and object detection circuit 107 so as to enable their operation, while only biasing voltages are provided to all other system components so that they are each initially disabled from operation. When power control switch 130 is in its POWER OFF state, power from battery power unit 126 is not commuted to power distribution circuit 125, and thus not provided to any components in the system. As will be described in greater detail hereinafter, provision of electrical power to all other system components occurs under the management of the control architecture formed by the interaction of distributed control centers $C_1$, $C_2$ and $C_3$.

As shown in FIG. 8, primary clock oscillator circuit 101 supplies a periodic pulsed signal to both the system override signal detection circuit and the object detection circuit. In the illustrative embodiment, the primary oscillation circuit is designed to operate at a low frequency (e.g., about 1.0 Khz) and a very low duty cycle (e.g, about 1.0%). The "ON" time for the system override signal producing means and the IR object sensing circuit is proportional to the duty cycle of the primary oscillation circuit. This feature allows for minimal operating current when the bar code symbol reading device is in the object detection mode and also when the system override signal producing device is activated (i.e., produces a system override signal).

Figure 8C:
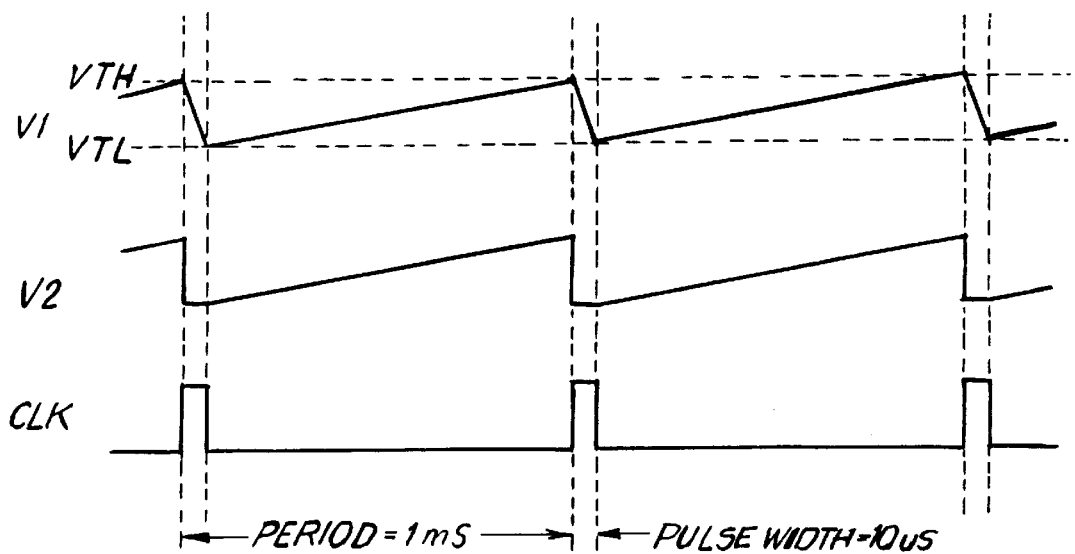
FIG. 8C is a timing diagram for the oscillator circuit of FIG. 8B.

As shown in FIG. 8B, primary oscillation circuit 101 comprises a Schmidtt trigger 142, invertors 143 and 144, and a NMOS Field-Effect Transistor (FET) 145. As shown, the output of trigger 142 is connected to the inputs of both invertors 143 and 144. The output of invertor 143 produces clock signal CLK which is provided to system override signal detection circuit 100 and object detection circuit 107. The primary oscillation circuit is connected to first RC network 102 which comprises resistors $R_1$ and $R_2$, and capacitor $C_1$ configured as shown in FIG. 8B. The function of the RC network 102 is to establish the duty cycle and the oscillation period of the primary oscillator circuit. As shown, two time constants (i.e., loads) are established by the network using capacitor $C_1$ and resistors $R_1$ and $R_2$. The RC combination of $R_1$ and $C_1$ establishes the period of the oscillator. The ratio of the $R_2$ to $R_1$ provides the duty cycle of the oscillator. The value of $R_2$ is approximately 100 times smaller than $R_1$ to establish a 1.0% duty cycle. As shown in the timing diagram of FIG. 8C, the clock signal CLK remains low while the $V_1 1$ signal ramps up. This ramp up time is the time it takes for the capacitor $C_1$ to charge through $R_1$. The clock signal CLK then goes HIGH for the shorter discharge time of the capacitor through $R_2$. By adjusting the duty cycle (i.e., increasing or decreasing the value of resistor $R_2$), the sensitivity of the object detection circuit can be tuned such that it activates consistently at a specified distance from the light transmission a window of the bar code symbol reading device.

In accordance with the present invention, the purpose of object detection circuit 107 is to produce a first control activation signal $A_1=1$ upon determining that an object (e.g., product, document, etc.) is present within the object detection field of the bar code symbol reading device, and thus at least a portion of the scan field thereof. As illustrated in FIG. 8, the object detection circuit is activated (i.e., enabled) by enabling, signal $E_0$ supplied from first control circuit $C_1$, and the object detection circuit provides the first control circuit $C_1$ with first control activation signal $A_1=1$ when an object residing in the scan field is detected. In the illustrative embodiment, an "active" technique of automatic object detection is employed, although it is understood that "passive" techniques may be used with acceptable results. As shown in FIG. 8, the object detection means of the system comprises two major subcomponents, namely object sensing circuit 106 and object detection circuit 107, both of which are locally controlled by control circuit $C_1$. In the illustrative embodiment, object sensing circuit comprises an IR LED 148 driven by an IR transmitter drive circuit 149, and an IR phototransistor (or photodiode) 150 activated by an IR receive biasing circuit 151. As shown in FIGS. 7D and 7F, these components are arranged and mounted on PC board 41 so as to provide an object detection field that spatially encompasses the laser scanning plane, as described above. As shown in FIG. 8, the object detection circuit 107 produces an enable signal IR DR which is provided to the IR transmitter drive circuit 149. The signal produced from IR phototransistor 151, identified as IR REC, is provided as input signal to the object detection circuit 107 for signal processing in a manner which will be described in detail below. In the illustrative embodiment, infrared LED 148 generates a 900 nanometer signal that is pulsed at the rate of the primary oscillation circuit 101 (e.g., 1.0 KHZ) when the object detection circuit is enabled by enable signal $E_0$ produced from the first control circuit $C_1$. Preferably, the duty cycle of the primary oscillation circuit 101 is less than 1.0% in order to keep the average current consumption very low.

As shown in FIG. 3A, in particular, this pulsed optical signal is transmitted from infrared LED 148 to broadly illuminate the scan field. When an object is present within the object detection portion of the scan field, a reflected optical pulse signal is produced and focussed through focusing lens 153 onto photodiode 150. The function of photodiode 150 is to receive (i.e., sense) the reflected optical pulse signal and, in response thereto, produce a current signal IR REC.

Figure 8D:
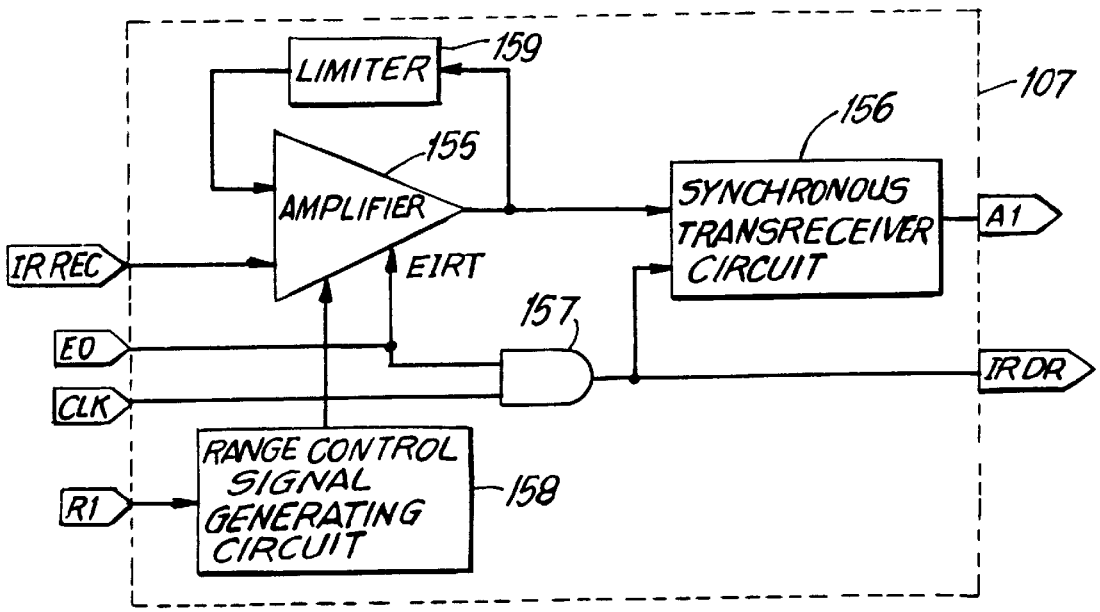
FIG. 8D is a block functional diagram of the object detection circuit (i.e., system activation means) in the ASIC chip in the automatic bar code symbol reading device of the present invention.

As shown in FIG. 8D, produced current signal IR RE (is provided as input to the current-to-voltage amplifier (e.g., transconductance amplifier) 155 in the object detection circuit, and is converted into a voltage signal Vo. Within the object detection circuit 107, the infra-red LED drive signal IR DR is produced as the output of AND gate 157, whose inputs are enabling signal $E_0$ supplied from the first control circuit $C_1$ and the pulsed clock signal CLK supplied from the primary oscillation circuit 101.

As shown in FIG. 8D, enabling signal $E_0$ is also provided to current-to-voltage amplifier circuit 155, and the output voltage signal from AND gate 157 is provided as the second input to the synchronous transmitter/receiver circuit 156. Notably, the output voltage signal from AND gate 157 and the output voltage signal $V_0$ from the current-to-voltage amplifier correspond to the IR pulse signal trains transmitted from and received by object sensing circuit 106. The function of the synchronous transmitter/receiver circuit is to cyclically compare the output voltage signal from AND gate 157 and the output voltage signal $V_0$ from the current-to-voltage amplifier, and if these voltage signals synchronously match each other for a minimum of three (3) consecutive cycles of the primary oscillation circuit 101, then synchronous transmitter/receiver circuit 156 produces as output, a first control activation signal $A_1=1$, indicative that an object is present in the scan field of the bar code symbol reading device. Conversely, whenever first control activation signal $A_1=0$ is produced, then this condition indicates that an object is not present in the scan field.

Alternatively, the automatic bar code reading device of the present invention can be readily adapted to sense ultrasonic energy reflected off an object present within the scan field. In such an alternative embodiment, object sensing circuit 106 is realized as an ultrasonic energy transmitting/receiving mechanism. In the housing of the bar code reading device, ultrasonic energy is generated and transmitted forwardly into the scan field. Then, ultrasonic energy reflected off an object within the object detection field is detected adjacent to the transmission window using an ultrasonic energy detector that produces an analog electrical signal (i.e., UE REC) indicative of the detected intensity of received ultrasonic energy. Preferably, a focusing element is disposed in front of the energy detector in order to effectively maximize the collection of ultrasonic energy reflected off objects in the scan field. In such instances, the focusing element essentially determines the geometrical characteristics of the object detection field of the device. Consequently, the energy focusing (i.e., collecting) characteristics of the focusing element will be selected to provide an object detection field which spatially encompasses at least a portion of the scan field. The electrical signal produced from the ultrasonic-energy based object sensing circuit is provided to object detection circuit 107 for processing in the manner described above.

In the illustrative embodiment, object detection circuit 107 is provided with two different modes of detection, namely, a long-range mode of object detection and a short-range mode of object detection. As shown in FIGS. 8 and 8D, these modes are set by range selection circuit 115 using mode enable signal $R_1$. When induced into the long-range mode of object detection, object detection circuit 107 will generate first control activation signal $A_1=1$ whenever an object has been detected within the operative range of the object detection field, independent of the particular distance at which the object resides from the transmissive window. When induced into the short-range mode of object detection, the object detection circuit will generate first activation control signal $A_1=1$ only when an object is detected at a distance within the short-range of the object detection field.

As schematically indicated in FIGS. 2 and 2A, the long-range specification for object detection is preferably preselected to be the full or entire range of sensitivity provided by current-to-voltage amplifier (e.g., 0 to about 10 inches). Preferably, the short-range specification for object detection is preselected to be the reduced range of sensitivity provided by the IR sensing circuit when mode enable signal $E_{IRT}=1$ is provided to the desensitization port of amplifier 155. In the illustrated embodiment, the short-range of object detection is about 0 to about 3 inches or so to provide CCD-like scanner emulation. As will become apparent hereinafter, the inherently limited depth and width of field associated with the short-range mode of object detection prevents laser scanning mechanism 108 from flooding the scan field with laser scanning light and thus inadvertently detecting undesired bar code symbols. Particular uses to which object detection range selection can be put, will be described in greater detail hereinafter.

As shown in FIG. 8D, the sensitivity (i.e., gain) of current-to-voltage amplifier 155 is controlled by a sensitivity control signal $E_{IRT}$ produced from range control signal generating circuit 158. In the illustrative embodiment, the sensitivity control signal $E_{IRT}$ 160 is produced by a resistance network whose values are selected using an analog switch that is responsive to a range select signal $R_1$ produced by range selection circuit 115. As such, the sensitivity of the current-to-voltage amplifier is simply adjusted by selecting one of two resistance values within the resistance network used to realize range control signal generating circuit 158. The short range mode of object detection is enabled by selecting a resistance value that produces an amplifier gain that is lower than that produced during the long-range mode, of object detection where detectable objects can reside further away from the light transmission window of the bar code symbol reading device.

In general, first control logic block $C_1$ provides the first level of system control. This control circuit activates the object detection circuit 107 by generating enable signal $E_0=1$, it tactivates laser beam scanning circuit 108, photo-receiving circuit 109 and A/D conversion circuit 110 by generating enable signal $E_1=1$, and it activates bar code symbol detection circuit 111 by generating enable signal $E_2=1$. In addition, the first control circuit $C_1$ provides control lines and signals in order to control these functions, and provides a system override function for the low power standby mode of the bar code symbol reading device. In the illustrative embodiment, the specific operation of first control circuit $C_1$ is dependent on the state of several sets of input signals (i.e., activation control signal $A_0$ and $A_1$, and override signals $C_2/C_1$, $C_3/C_1-1$ and $C_3/C_1-2$) and an internally generated digital timer signal B. A preferred logic implementation of the first control circuit $C_1$ is set forth in FIGS. 8E and 8F. The functional dependencies among the digital signals in this circuit are represented by the Boolean logic expressions set forth in the Table of FIG. 8G, and therefore are sufficient to uniquely characterize the operation of first control circuit $C_1$.

Figure 8E:
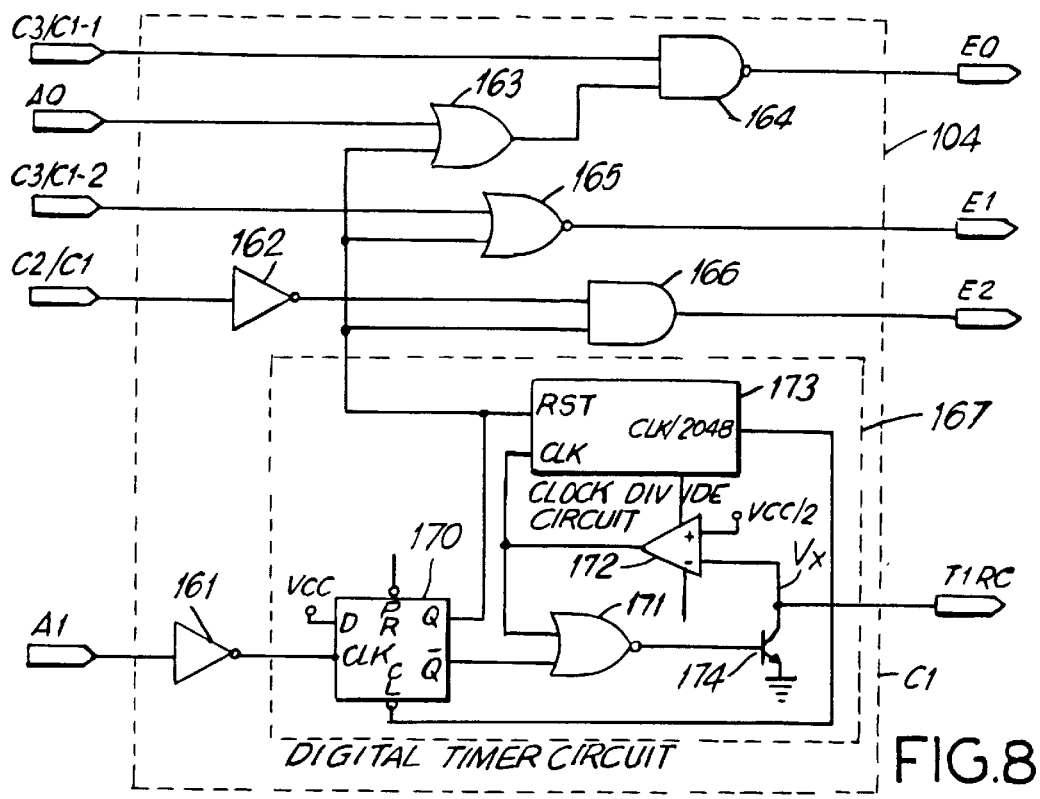
FIG. 8E is a functional logic diagram of the first control circuit ($C_1$) of the control system of the present invention.

As shown in FIG. 8E, first control circuit comprises a pair of logic invertors 161 and 162, a NAND gate 164, a NOR gate 165, an AND gate 166, and a digital timer circuit 167 which produces as output, a digital output signal B. As shown, digital timer circuit 167 comprises a flip-flop circuit 170, a NOR gate 171, a clock divide circuit 173, a comparator (i.e., differential) amplifier 172, and a NPN transistor 174. As illustrated, activation control signal $A_1$ is provided to the CLK input of flip-flop 170 by waly of invertor 161. The QNOT output of the flip-flop is provided as one input to NOR gate 171, whereas the other input thereof is connected to the CLK input of clock divide circuit 173 and the output: of comparator amplifier 172. The output of the NOR gate is connected to the base of transistor 174, while the emitter thereof is connected to electrical ground and the collector is connected to the negative input of comparator amplifier 172 as well as the second timing network 105, in a manner similar to the interconnection of first timing network 102 to primary oscillation circuit 101. Also, the divided clock output (i.e., CLK/2048) produced from clock divide circuit 173 is provided to the CL input of flip-flop 170. As shown, the Q output of flip-flop 170 is connected to the reset (RST) input of the clock divide circuit 173 as well as to one input of NAND gate 164, one input of NOR gate 165, and one input of AND gate 166. Notably, the Q output of the flip-flop is the digital output signal B indicated in each of the Boolean expressions set forth in the Table of FIG. 8G.

As shown in FIG. 8E, the override signal $C_2/C_1$ from second control circuit $C_2$ is provided as the input to invertor 162, whereas the output thereof is provided as the second input to AND gate 166. The override signal $C_3/C_1-1$ from third control module $C_3$ is provided as the second input to NAND gate 164, whereas the output thereof produces enable signal $E_0$ for activating the object detection circuit 107. The override signal $C_3/C_1=2$ is provided to the second input to NOR gate 165, whereas the output thereof produces enable signal $E_1$ for activating laser scanning and photoreceiving circuits 108 and 109 and A/D conversion circuit 110. The output of AND gate 166 produces enable signal $E_2$ for activating bar code symbol detection circuit 111.

Figure 8F:
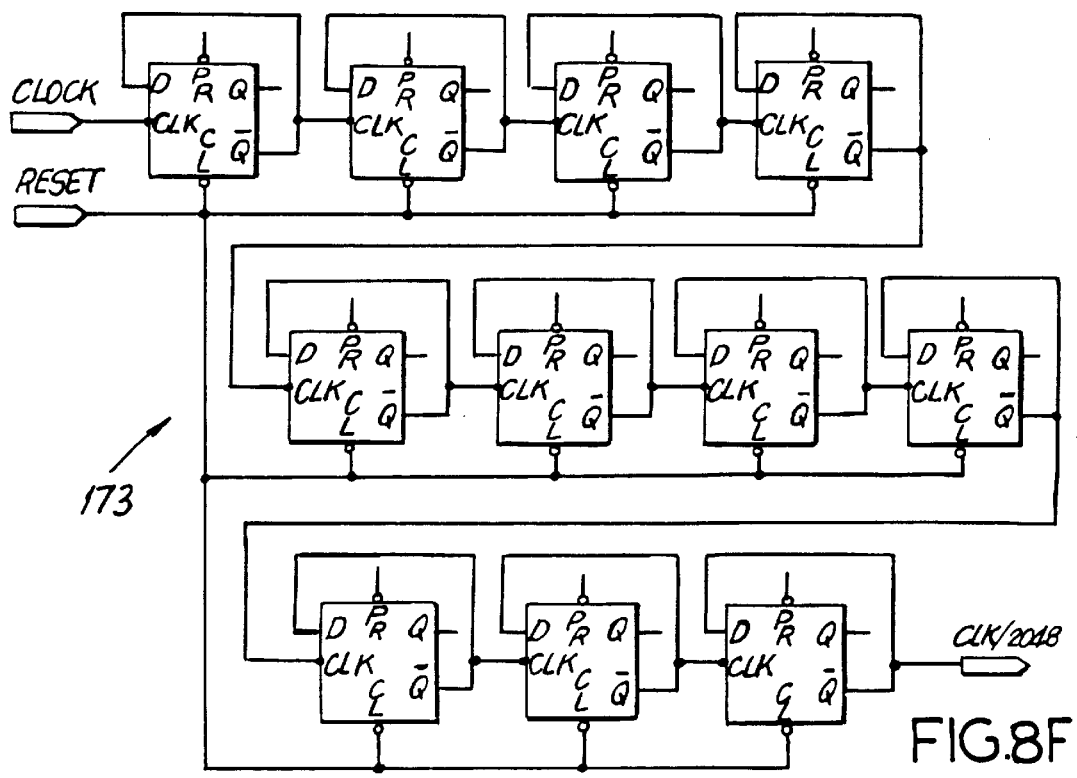
FIG. 8F is a functional logic diagram of the clock divide circuit in the first control circuit $C_1$ of FIG. 8E.

Referring to FIG. 8E, the operation of digital timer circuit will be described. The output voltage of comparator amplifier 172 keeps transistor 174 in its non-conducting state (i.e., OFF), via NOR gate 171, thus allowing the external RC network 105 to charge to capacity. When comparator input voltage Vx exceeds reference voltage VCC/2, the comparator output voltage biases (i.e., switches ON) transistor 174 so as to begin discharging the RC timing network 105, until input voltage Vx falls below reference voltage VCC/2 upon which the process repeats, thus generating a digital clock oscillation at the comparator output. The timing cycle of digital output signal B is initiated by a transition on the activation control signal A, which toggles flip-flop 170. This toggling action sets the digital output signal B to its logical HIGH state, resetting clock divide circuit 173 and starting the digital clocks oscillator described above by toggling the Q output of flip-flop 170. As shown in FIG. 8F, clock divide circuit 173 is constructed by cascading eleven flip-flop circuits together in a conventional manner. Each stage of the clock divider circuit divides the input clock signal frequency by the factor 2. Thus the clock divider circuit provides an overall division factor of 2048. When the clock output CLK/2048 toggles, the flip-flop circuit is cleared thus setting the digital signal B to logical LOW until the next pulse of the activation control signal $A_1$.

Figures 8G, 8H:
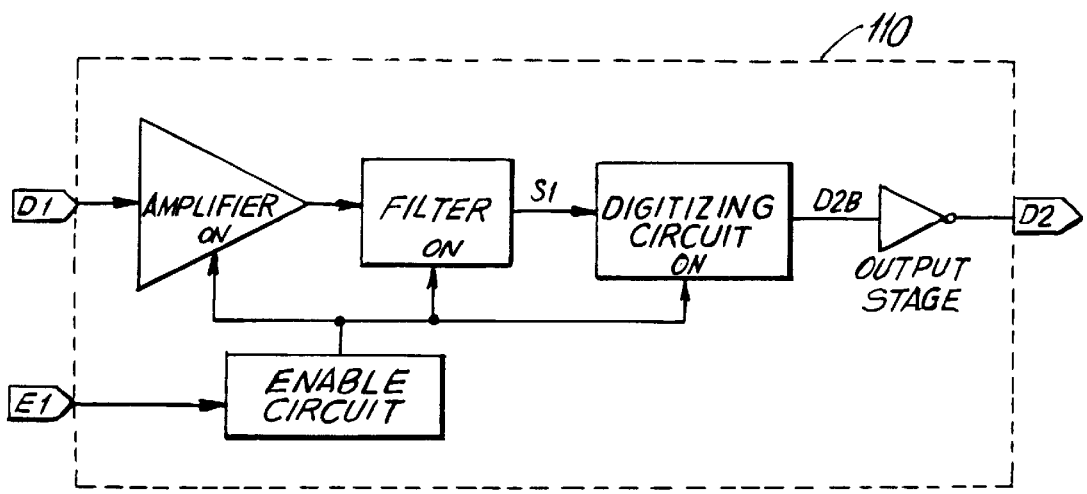
FIG. 8G is table setting forth Boolean logic expressions for the enabling signals produced by the first control circuit $C_1$.
FIG. 8H is a functional block diagram of the analog to digital (A/D) signal conversion circuit in the ASIC chip in the bar code symbol reading device of the present invention.

As reflected in the Boolean expressions of FIG. 8G, the state of each of the enable signals $E_0$, $E_1$ and $E_2$ produced by the first control circuit $C_1$ is dependent on whether the bar code symbol reading system is in its override state of operation. To better, understand the operation of control circuit $C_1$, it is helpful to consider a few control strategies preformed thereby.

In the override state of operation of the system, enable signal $E_0$ can be unconditionally set to $E_0=0$ by the third control circuit $C_3$ setting override signal $C_3/C_1=0$. Under such conditions, the object detection circuit is enabled. Also, when the laser scanning and photoreceiving circuits are activated (i.e., B=1) and override signal $C_3/C_1-1=1$, then enable signal $E_0=1$ and therefore the object detection circuit is automatically deactivated. The advantage of this control strategy is that it is generally not desirable to have both the laser scanning circuit 108 and photoreceiving circuit 109 and the object sensing circuit 105 active at the same time, as the wavelength of the infrared LED 148 typically falls within the optical input spectrum of the photoreceiving circuit 109. In addition, less power is consumed when the object detection circuit 107 is inactive (i.e., disabled).

As illustrated in FIG. 8, laser scanning circuit 108 comprises a solid-state visible laser diode (VLD) 177 driver, by a conventional driver circuit 178. In the illustrative embodiment, the wavelength of visible laser light produced from the laser diode is preferably about 670 nanometers. In order to repeatedly scan the produced laser beam over the scanning volume, the rotating polygon is rapidly accelerated to operating speed by motor 37 driven by a conventional driver circuit 181, as shown. Stationary mirror 44 directs the laser beam from the laser diode to the rotating polygon. To selectively activate both laser light source 38 and motor 37, a laser diode and scanning motor enable signal $E_1$ provided as input to driver circuits 178 and 181. When enable it signal $E_1$ is a logical "high" level (i.e., $E_1=1$) a laser beam is generated and projected through the light transmissive window, when the projected laser beam is repeatedly scanned through the scanning volume, and an optical scan data signal is thereby produced off the object (and bar code) residing within the scanning volume. When a laser diode and scanning motor enable signal $E_1$ is a logical "low" (i.e., $E_1=0$), there is no laser beam produced, projected, or scanned across the scanning volume.

When a bar code symbol is present on the detected object at the time of scanning, the visible laser beam is automatically scanned across the bar code symbol within the 3-D scanning volume, and incident laser light on the bar code symbol will be scattered and reflected. This scattering/reflection process produces a laser light return signal of variable intensity which represents a spatial variation of light reflectivity characteristic of the pattern of bars and spaces comprising the bar code symbol. Photoreceiving circuit 109 detects at least a portion of the reflected laser light of variable intensity and produces an analog scan data signal Dindicative of the detected light intensity.

In the illustrative embodiment, photoreceiving circuit 109 generally comprises a number of components, namely: laser light collection optics (i.e., stationary mirror array 38 and focusing mirror 43) for focusing reflected laser light for subsequent detection; photoreceiver 41 (e.g., a silicon photosensor) mounted onto PC board 40, as shown in FIG. 5D, for detecting laser light focused by the light collection optics; and frequency selective filter 186A, mounted in front of photoreceiver 41, for transmitting thereto only optical radiation having wavelengths up to a small band above 670 nanometers.

In order to prevent optical radiation slightly below 670 nanometers from passing through light transmission aperture 12A and entering the housing, the light transmissive window 68 realized as a plastic filter lens is installed over the light transmission aperture of the housing. This plastic filter lens has optical characteristics which transmit only optical radiation from slightly below 670 nanometers. In this way, the combination of plastic filter lens 12 at the transmission aperture and frequency selective filter 186A before photoreceiver 41 cooperate to form a narrow band-pass optical filter having a center frequency $f_c$=670 nanometers. By permitting only optical radiation associated with the visible laser beam to enter the housing, this optical arrangement provides improved signal-to-noise ratio for detected scan data signals $D_1$. This novel filtering optical arrangement is disclosed in greater detail in copending application Ser. No. 08/439,224, supra.

In response to reflected laser light focused onto photo receiver 41, photoreceiver 41 produces an analog electrical signal which is proportional to the intensity of the detected laser light. This analog signal is subsequently amplified by preamplifier 187 to produce analog scan data signal $D_1$. In short, laser scanning circuit 108 and photoreceiving circuit 109 cooperate to generate analog scan data signals $D_1$ from the scan field, over time intervals specified by first control circuit $C_1$ during normal modes of operation, and by third control module $C_3$ during "control override" modes of operation.

As illustrated in FIG. 8, analog scan data signal $D_1$ is provided as input to A/D conversion circuit 110, shown in FIG. 8H. In a manner well known in the art, A/D conversion circuit 110 processes analog scan data signal $D_1$ to provide a digital scan data signal $D_2$ which has a waveform that resembles a pulse width modulated signal, where logical "1" signal levels represent spaces of the scanned bar code and logical "0" signal levels represent bars of the scanned bar code. A/D conversion circuit 110 can be realized using any conventional A/D conversion techniques well known in the art. Digitized scan data signal $D_2$ is then provided as input to bar code presence detection circuit 111 and symbol decoding module 119 for use in performing particular functions required during the bar code symbol reading process of the present invention.

The primary purpose of bar code presence detection circuit 111 is to determine whether a bar code is present in or absent from the scan field, over time intervals specified by first control circuit $C_1$ during normal modes of operation and by third control module $C_3$ during control override modes of operation. In the illustrative embodiment, bar code presence detection circuit 111 indirectly detects the presence of a bar code in the narrowly-confined scanning volume 13 by detecting its bar code symbol "envelope". In the illustrative embodiment, a bar code symbol envelope is deemed present in the scanning volume upon detecting a corresponding digital pulse sequence in digital signal $D_2$ that A/D conversion circuit 110 produces when photoreceiving circuit 109 detects laser light reflected off a bar code symbol scanned by the laser beam produced by laser beam scanning circuit 108.

This digital pulse sequence detection process is achieved by counting the number of digital pulse transitions (i.e., falling pulse edges) that occur in digital scan data signal $D_2$ within a predetermined time period $T_1$ clocked by the bar code symbol detection circuit. According to the laws of physics governing the laser scanning operation, the number of digital (pulse-width modulated) pulses detectable at photoreceiver 41 during time period $T_1$ is a function of the distance of the bar code from the light transmission window 12 at the time of scanning. Thus a bar code symbol scanned at 6" from the light transmission window will produce a larger number of digital pulses (i.e., digital count) at photoreceiver 41 during time period $T_1$ than will the same bar code symbol scanned at 3" from the light transmission window.

In the illustrative embodiment, the bar code symbol detection circuit 111 is provided with the capacity to detect the presence of a bar code symbol in either the long or short range portions of the scanning volume, as specified in FIGS. 3 and 3A. This is achieved by counting the digital pulse transitions present in digital scan signal $D_2$ within predetermined time period $T_1$ and producing second control activation signal $A_{2S}$ (i.e., $A_{2S}$=1) when the counted number of pulse transitions equals or exceeds a first prespecified digital pulse transition count corresponding to a bar code symbol scanned in the short range portion of the scan field, and producing second control activation signal $A_{2L}$ (i.e., $A_{2L}$=1) when the counted number of pulse transitions equals or exceeds a second prespecified digital pulse transition count corresponding to a bar code symbol scanned in the long range portion of the scanning volume. As shown in FIG. 8, both of these second control activation signals $A_{2L}$ and $A_{2S}$ are produced and provided as input to second control circuit $C_2$. However, second control circuit $C_2$ selectively provides (e.g., gates) the second control activation signal that corresponds to range-mode of operation selected by the user. When the long range mode of operation has been selected by range selection circuit 115, the device will automatically undergo a transition from bar code presence detection state to bar code symbol reading state upon receiving control activation signal $A_{2L}$=1. Similarly, when the short range mode of operation has been selected by the range selection circuit 115, the device will automatically undergo a transition from bar code presence detection state to bar code symbol reading state upon receiving control activation signal $A_{2S}$=1.

Figure 8I:
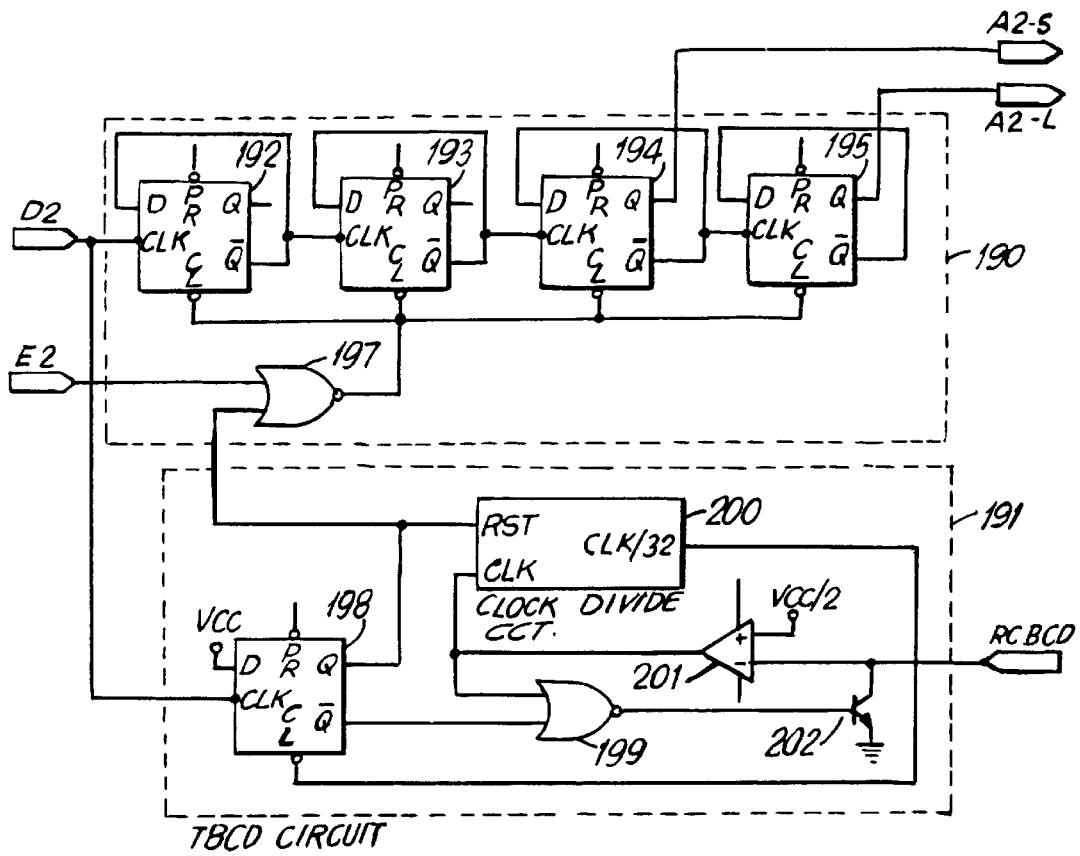
FIG. 8I is a functional logic diagram of the bar code symbol (presence) detection circuit in the ASIC chip in the bar code symbol reading device of the present invention.
Figure 8J:
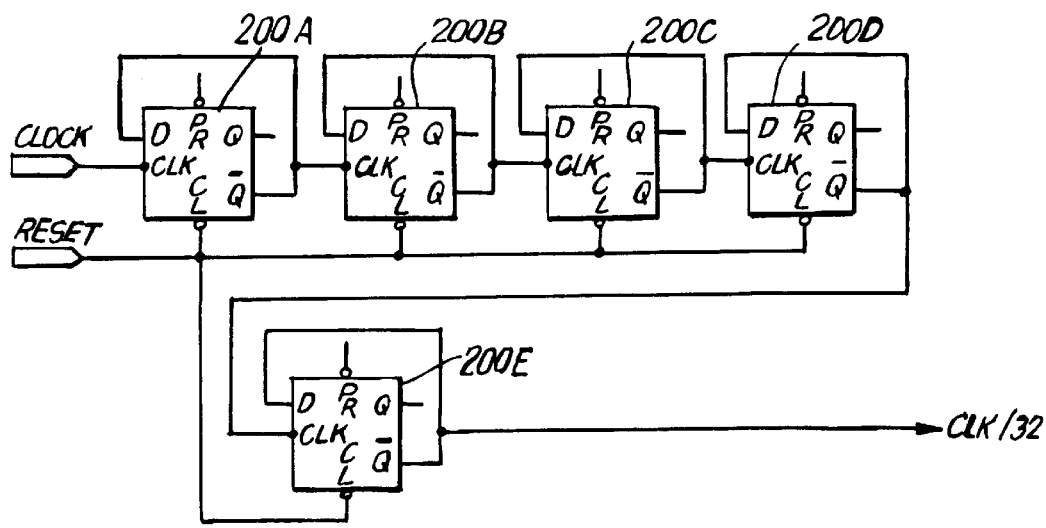
FIG. 8J is a functional logic diagram of the clock divide circuit in the bar code symbol detection circuit of FIG. 8I.
Figures 8K, 8M:
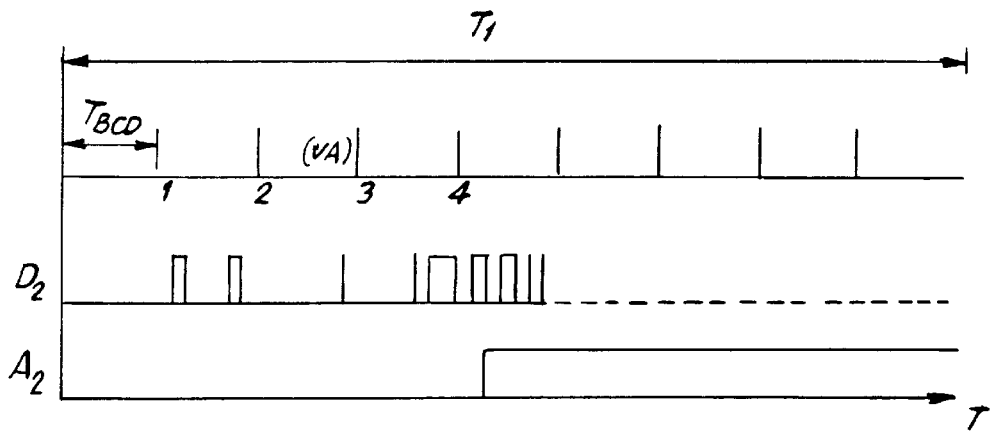
FIG. 8K is a schematic representation of the time window and subintervals maintained by the bar code symbol detection circuit during the bar code symbol detection process.
FIG. 8M is Boolean logic table defining the functional relationships among the input and output signals into and out from the second control circuit $C_2$ of FIG. 8N.

In the illustrative embodiment, bar code symbol presence detection circuit 111 comprises a digital pulse transition counter 190 for counting digital pulse transitions during time period $T_1$, and a digital clock circuit (i.e., $T_{BCD}$ circuit) 191 for measuring (i.e., counting) time period $T_{BCD}$ and producing a count reset signal CNT RESET at the end of each such time period, as shown in FIG. 8K. As shown in FIG. 8K, the function of digital clock circuit 191 is to provide a time period $T_{BCD}$ (i.e., time window subdivision) within which the bar code symbol detection circuit attempts, repeatedly during time period $T_1$, to detect a bar code symbol in the scan field. In the preferred embodiment, $T_{BCD}$ is about 0.1 seconds, whereas $T_1$ is about 1.0 second. As shown in FIG. 8I, in order to establish such "bar code search" time it subintervals within time period $T_1$, the digital clock circuit 191 generates the first count reset pulse signal CNT RESET upon the detection of the first pulse transition in digital scan data signal $D_2$. The effect of this reset signal is to clear or reset the digital pulse transition (falling edge) counter. Then at the end of each time subinterval $T_{BCD}$, digital clock signal 191 generates another count reset pulse CNT RESET to reset the digital pulse transition counter. If during time window $T_1$, a sufficient number of pulse transitions in signal $D_2$ are counted over a subinterval $T_{BCD}$, then either control activation signal $A_{2L}$ or $A_{2S}$, will be set to "1". In response to the detection of this condition, second control circuit $C_2$ automatically enables control activation $C_3$ in order to initiate a transition from the bar code symbol detection state of operation to the bar code symbol reading state of operation.

As shown in FIG. 8I, digital pulse transition counter 191 is formed by wiring together a series of four flip-flop circuits 192 to 195, such that each flip flop divides the clock signal frequency of the previous stage by a factor of 2. As indicated in the drawing of FIG. 8I, the Q output of flip flops 192 to 194 represent the binary digits 2, 4, 8, and 16 respectively, of a binary number (i.e., counting) system. As shown, enable signal $E_2$ from first control circuit $C_1$ is provided as input to NOR gate 197, while the second input thereto is the counter reset signal CNT RESET provided from the digital counter circuit 191. In order to reset or clear the pulse transition counter circuit 190 upon the generation of each CNT RESET pulse, the output of the NOR gate 197 is connected to the clear line (CL) of each flip flop 192 to 195, as shown.

As illustrated in FIG. 8, digital clock circuit 191 comprises a flip-flop circuit 198, a NOR gate 199, a clock divide circuit 200, a comparator 201, and a NPN transistor 202. As illustrated, digital scan data signal $D_2$ is directly provided to the CLK input of flip-flop 198. The QNOT output of the flip-flop is provides as one input to NOR gate 199, whereas the Q output thereof is connected to the CLK input of clock divide circuit 200 and the second input of NOR gate 197. The other input of NOR gate 199 is connected to the input line CLK of clock divide circuit 200 and to the output of comparator 201, as shown. The output of the NOR gate is connected to the base of transistor 202, while the emitter thereof is connected to electrical ground and the collector is connected to the negative input of comparator 201 as well as to the third timing network 112, in a manner similar to the interconnection of the first timing network 102 to primary oscillation circuit 101. As shown in FIG. 8J, clock divide circuit 200 is realized as series of five flip-flops 200A to 200E wired together so as to divide digital clock input signal CLOCK by 32, and be resettable by pulsing reset line RESET in a conventional manner.

When an object is detected in the scan field, first control circuit $C_1$ produces enable signal $E_2$=1 so as to enable digital pulse transition counter 190 for a time duration of $T_1$. As shown, the digital scan data signal $D_2$ (representing the bars and spaces of the scanned bar code) drives the clock line of first flip flop 192, as well as the clock line of flip flop 198 in the $T_{BCD}$ timer circuit. The first pulse transition in digital scan data signal $D_2$ starts digital timer circuit 191. The production of each count reset pulse CNT RESET from digital timer circuit 191 automatically clears the digital pulse transition counter circuit 190, resetting it once again to count the number of pulse transitions present in the incoming digital scan data signal $D_2$ over a new time subinterval $T_{BCD}$. The Q output corresponding to eight pulse transitions counted during time period TBCD, provides control activation signal $A_2S$ for use during the short range mode of operation. The Q output corresponding to sixteen pulse transitions counted during time period $T_{BCD}$, provides control activation signal $A_{2L}$ for use during the long range mode of operation. When the presence of a bar code in the scan field is detected, second activation control signal $A_{2L}$ or $A_{2S}$ is generated, third control circuit $C_3$ is activated and second control circuit $C_2$ is overridden by third control circuit $C_3$ through the transmission of control override signals (i.e., $C_3/C_2$ inhibit and $C_3/C_1$ enable signals) Prom the third control circuit $C_3$.

Figure 8L:
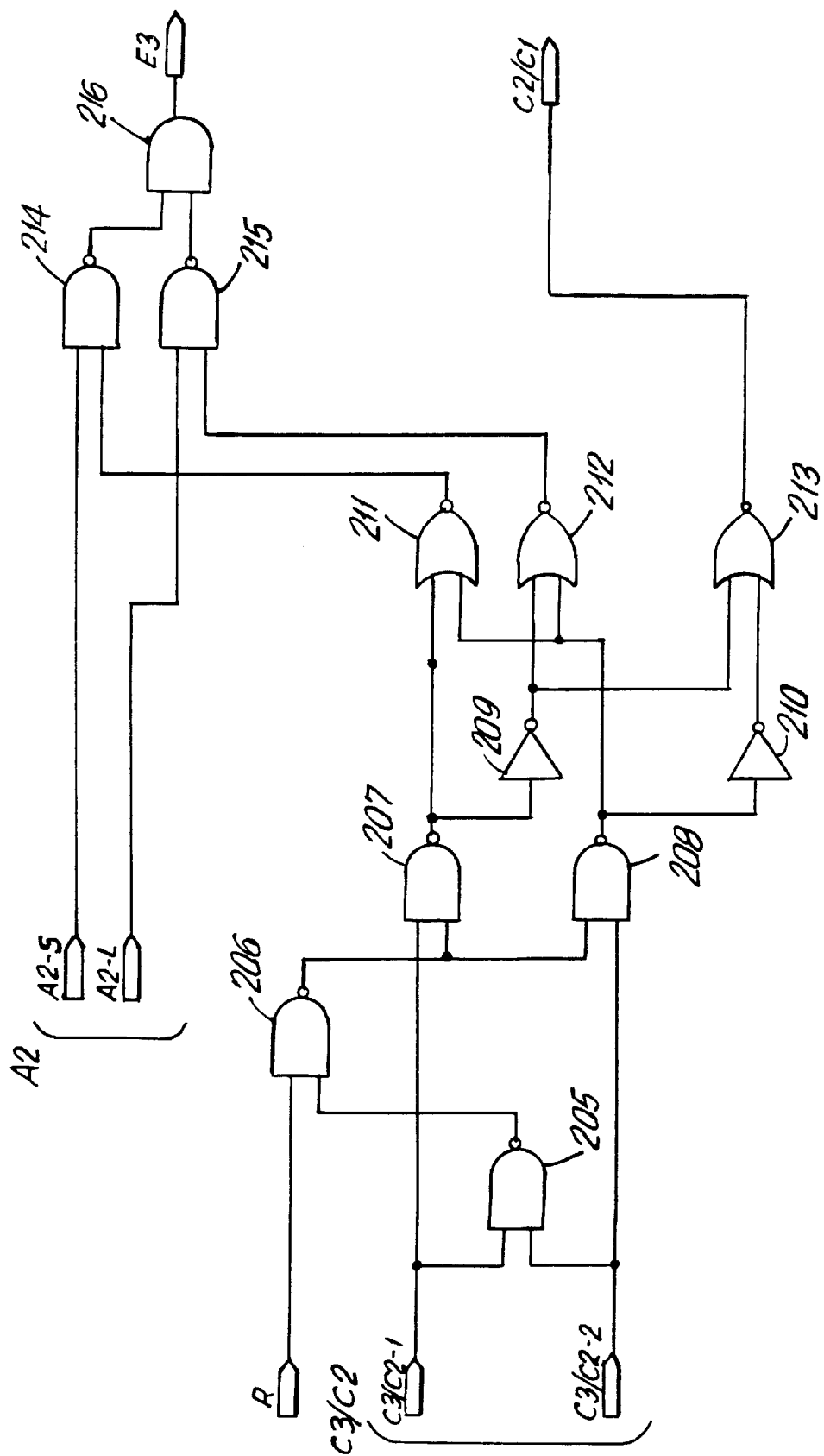
FIG. 8L is a functional logic diagram of the second control circuit ($C_2$) in the ASIC chip in the automatic bar code symbol reading device of the present invention.

As illustrated in FIG. 8L, second control circuit $C_2$ is realized using logic circuitry consisting of NAND gates 205 to 208, invertors 209 and 210, NOR gates 211 to 213, NAND gates 214 and 215, AND gate 216, configured together as shown. As shown, second control activation signals $A_{2S}$. and $A_{2L}$ are provided to the first inputs of NAND gates 214 and 215, respectively, whereas the outputs of NOR gates 211 and 212 are provided to the second inputs of NAND gates 214 and215 respectively. The outputs of NAND gates 214 and 215 are provided to the inputs of AND gate 216 and the output thereof provides enable signal $E_3$ for enabling third control module $C_3$.

As shown in FIG. 8L, the third control module $C_3$ provides override signals $C_3/C_2$–1 and $C_3/C_2$–2 to the first and second inputs of NAND gate 205 and to the first input of NAND gate 207 and the first input of NAND gate 208, respectively. The range selection signal R produced from range selection circuit 115 is provided as input to NAND gate 206. As shown, output of NAND gate 205 is provided as the second input to NAND gate 206. The output of NAND gate 206 is provided as the second input to NAND gate 207 and the, second input to NAND gate 208. As shown in FIG. 8L, the output of NAND gate 207 is provided as an input to NOR gate 211 and invertor 209, whereas the output of NAND gate 208 is provided as inputs to NOR gates 211 and 212 and invertor 210. The output of invertor 209 is provided as the other input to NOR gate 212 and one input to NOR gate 213. The output of invertor 210 is provided as another input to NOR gate 213, whereas the output thereof provides control override signal $C_2/C_1$. So configured, the combinational logic of the second control circuit $C_2$ maps its input signals to its output signals in accordance with the logic table of FIG. 8M.

Upon entering the bar code symbol reading state, third control module $C_3$ provides override control signal $C_3/C_1$ to first control circuit $C_1$ and second control circuit $C_2$. In response to control signal $C_3/C_1$, the first control circuit $C_1$ produces enable signal $E_1$=1which enables scanning circuit, 109 photo-receiving E circuit 109 and A/D conversion circuit 110. In response to control signal $C_3/C_2$, the second control circuit $C_2$ produces enable signal $E_2$=0, which disables bar code symbol detector circuit 111. Thereafter, third control module $C_3$ produces enable signal $E_4$ to enable symbol decoding module 119. In response to the production of such signals, the symbol decoding module decode processes, scan line by scan line, the stream of digitized scan data contained in signal $D_2$ in an attempt to decode the detected bar code symbol within the second predetermined time period $T_2$ established and monitored by the third control module $C_3$. If the symbol decoding module 119 successfully decodes the detected bar code symbol within time period $T_2$, then symbol character data $D_3$ (representative of the decoded bar code symbol and typically in ASCII code format) is produced. Thereupon symbol decoding module 119 produces and provides the third control activation signal $A_3$ to the third control module $C_3$ in order to induce a transition from the bar code symbol reading state to the data packet transmission state. In response thereto, a two distinct events occur. First the third control module $C_3$ produces and provides enable signal $E_5$ to data packet synthesis module 120. Secondly, symbol decoding module 119 stores symbol character data $D_3$ in a memory buffer associated with data packet synthesis module 120.

Figure 13A:
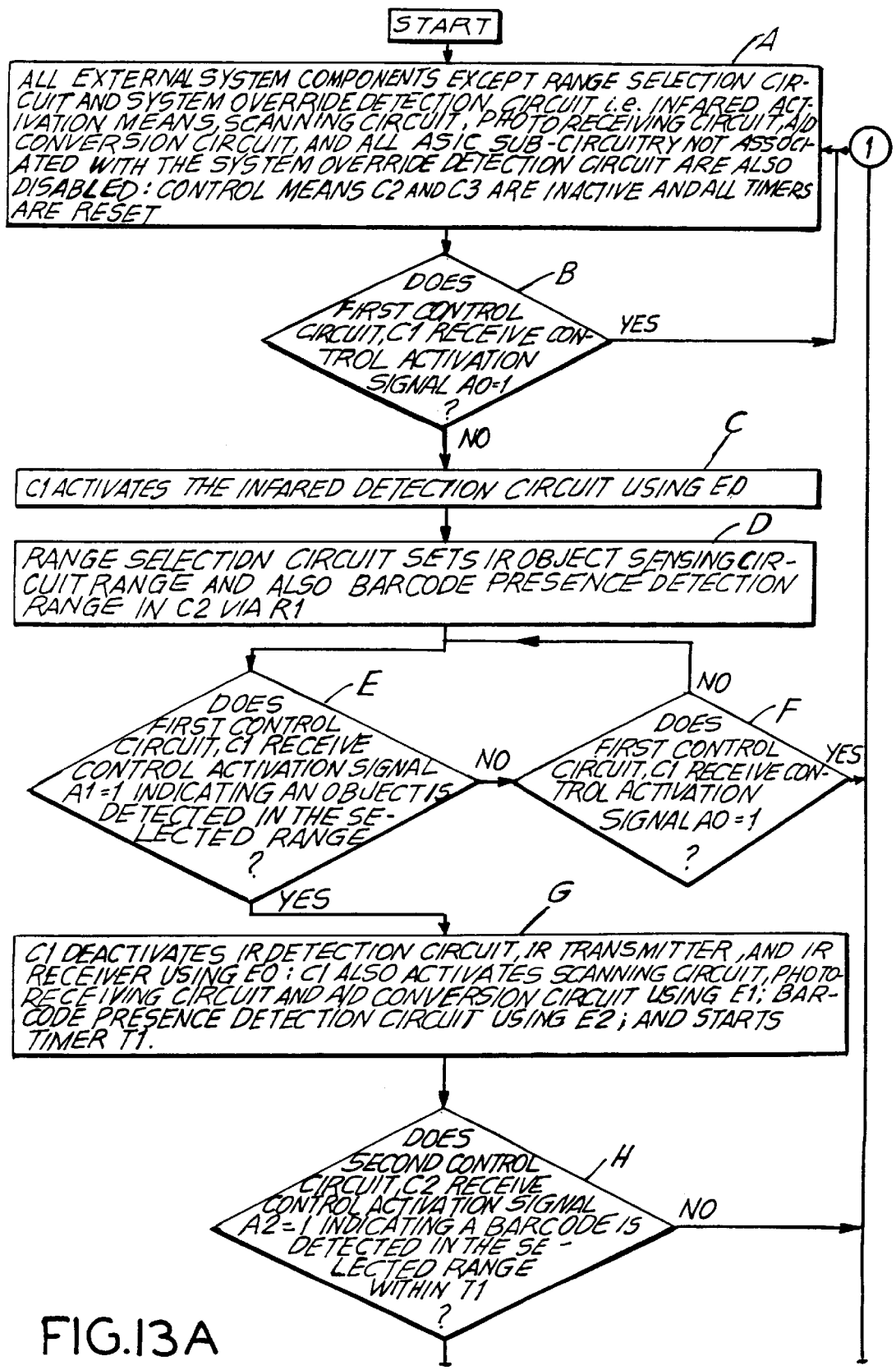
FIGS. 13A, 13AA, 13B, 13C, taken together, show a high level flow chart of the control process performed by the control subsystem of the bar code symbol reading device, illustrating various modes of object detection, bar code presence detection and bar code symbol reading.
Figure 13A:
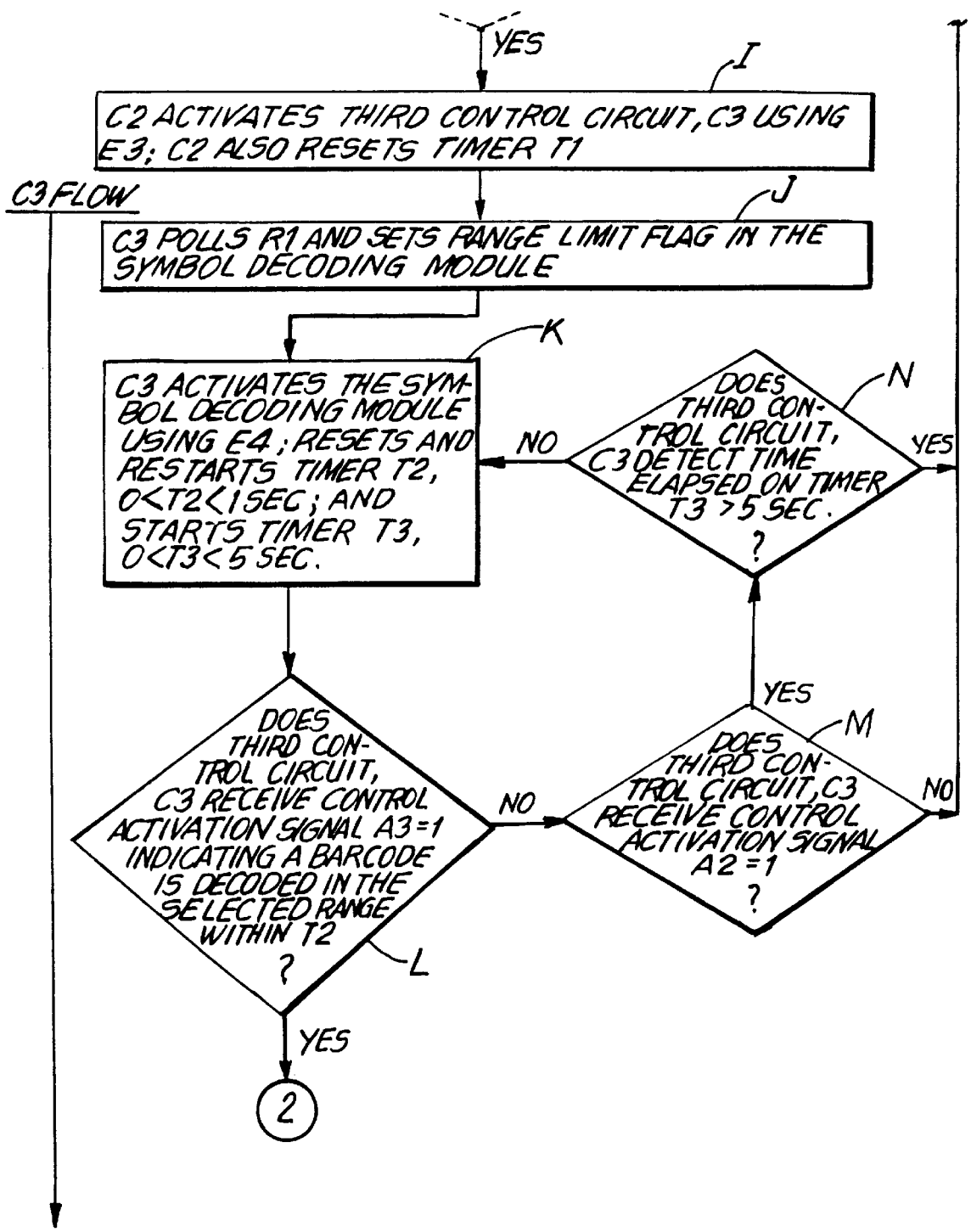

In the illustrative embodiment, symbol decoding module 119, data packet synthesis module 120, and timers $T_2$, $T_3$, $T_4$ and $T_5$ are each realized using programmed microprocessor and accessible memory 134. Similarly, third control module $C_3$ and the control functions which it performs at Blocks to GG in FIGS. 13A and 13C, are realized as a programming implementation using techniques well known in the art.

The function of data packet synthesis module 120 is to use the produced symbol character data to synthesize a group of data packets for subsequent transmission to its assigned base unit by way of data packet transmission circuit 121.

Figure 8N:
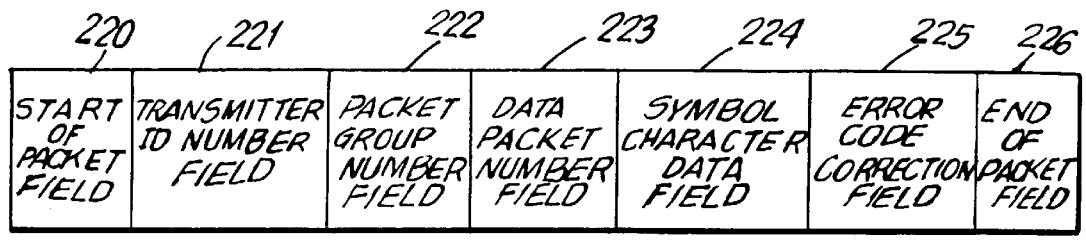
FIG. 8N is a schematic representation of the format of each data packet transmitted from the data packet transmission circuit of FIG. 9.

In the illustrative embodiment, each synthesized data packet is formatted as shown in FIG. 8N. In particular, each data packet in each data packet group comprises a number of data fields, namely: Start of Packet Field 220 for containing a digital code indicating the beginning of the transmitted data packet; Transmitter Identification Number Field 221 for containing a digital code representative of the Transmitting Bar Code Symbol Reader; Data Packet Group Number Field 222 for containing a digital code (i.e., a first module number) assigned to each particular data packet group being transmitted; Data Packet Transmission No. Field 223 for containing a digital code (i.e., a second module number) assigned to each data packet in each data packet group being transmitted; Symbol Character Data Field 224 for containing digital code representative of the symbol character data being transmitted to the base unit; Error Correction Code Field 225 for containing a digital error correction code for use by the receiving base unit to determine if error in data packet transmission has occurred; and End of Packet Field for 226 for containing a digital code indicating the end of the transmitted data packet.

Figure 9:
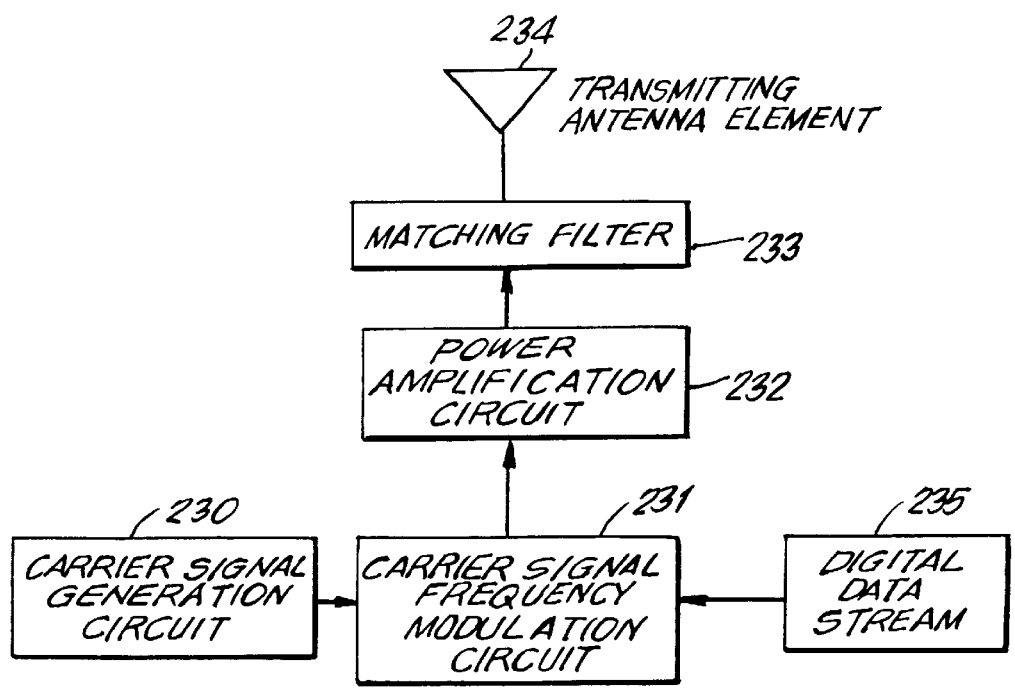
FIG. 9 is a functional block diagram of the data packet transmission circuit of the bar code symbol reading device of the present invention.

After the data packet synthesis module synthesizes a group of data packets as described above, the third control module $C_3$ provides enable signal $E_7$ to data packet transmission circuit 121. As illustrated in FIG. 9, the data packet transmission circuit comprises a carrier signal generation circuit 230, a carrier signal frequency modulation circuit 231, a power amplifier 232, a matching filter 233, and a quarterwave (¼) transmitting antenna element 234. The function of the carrier signal generation circuit 2303 is to generate a carrier signal having a frequency in the RF region of the electromagnetic spectrum. In the illustrative embodiment, the carrier frequency is about 912 Mhz, although it is understood that this frequency may vary from one embodiment of the present invention, to another embodiment thereof. As the carrier signal is being transmitted from transmitting antenna 234, frequency modulation circuitry 231 modulates the instantaneous frequency of the carrier signal using the digital data sequence (i.e., digital data stream) 235 constituting the group of data packets synthesized by the data packet synthesis module 120. The function of the power amplifier is to amplify the power of the transmitted modulated carrier signal so that it may be received by a base unit of the present invention located within a predetermined data transmission range (e.g., from about 0 to about 30 feet).

In general, each base unit of the present invention performs a number of functions. First, the base unit receives the modulated carrier signal transmitted from a hand-supportable bar code symbol reading device within the data reception range of the base unit. Secondly, the base unit demodulates the received carrier signal to recover the data packet modulated thereunto during signal transmission. Thirdly, the base unit analyzes each of the recovered data packets to determine whether the received carrier signal was transmitted from a hand-supportable bar code symbol reading device preassigned to the receiving base unit. Fourthly, the base unit recovers the symbol character data from at least one data packet in a transmitted group of data packets, and ascertaining the reliability of the recovered symbol character data. Fifthly, the base unit generates an acoustical acknowledgement signal SACK that can be audibly perceived by the operator of the transmitting bar code symbol reading device while located in the data reception range of the base unit. Finally, the base unit transmits the received symbol character data to a host computer system or like device. Each of these functions will be described in greater detail during the detailed description of the Main System Control Routine set forth in FIGS. 13A to 13C.

In order to better understand the functions performed by the bar code symbol reading device and base unit of the present invention, it will be helpful to first describe the principles underlying the data communication method of the present invention, and thereafter discuss the role that the base unit plays in carrying out this communication method.

In general, one or more bar code symbol reading devices can be mated (i.e. registered or assigned) to operate with a single base unit 3. In a first illustrative embodiment of the present invention, each bar code symbol reading device is a (resultant) system of bar code symbol reading subsystems installed in physical proximity with each other. Typically, each system is a point of sale (POS) station comprising (i) a host computer system interfaced[0ax7]ith a base unit of the present invention and (ii) an automatic hand-supportable bar code symbol reading device preassigned to one of the base units. In such an illustrative arrangement, each bar code symbol reading device is mated (i.e. registered or associated) with a single base unit by storing a unique, preassigned "Transmitter Identification Code" in a memory device within the assigned base unit during a set-up procedure.

In the illustrative embodiment, the carrier frequency of the data packet transmitter in each bar code symbol reading device is substantially the same for all bar code symbol reading devices in the resultant system. Also, the data packet transmission range of each bar code symbol reading device will be substantially greater than the distance between each bar code symbol reading device and a neighboring base unit to which the bar code symbol reading unit is not assigned. Consequently, under such operating conditions, at any instance in time, any base station in the resultant system may simultaneously receive two or more packet modulated carrier signals which have been transmitted from two or more bar code symbol reading devices being used in the resultant system. These bar code symbol reading devices may include the bar code symbol reading device preassigned to the particular base unit as well as neighboring bar code symbol reading devices. Thus due to the principles of data packet transmission of present invention, there exists the possibility that any particular base unit may simultaneously receive two or more different data packets at any instant in time, thereby creating a "packet interference" situation.

Figure 10:
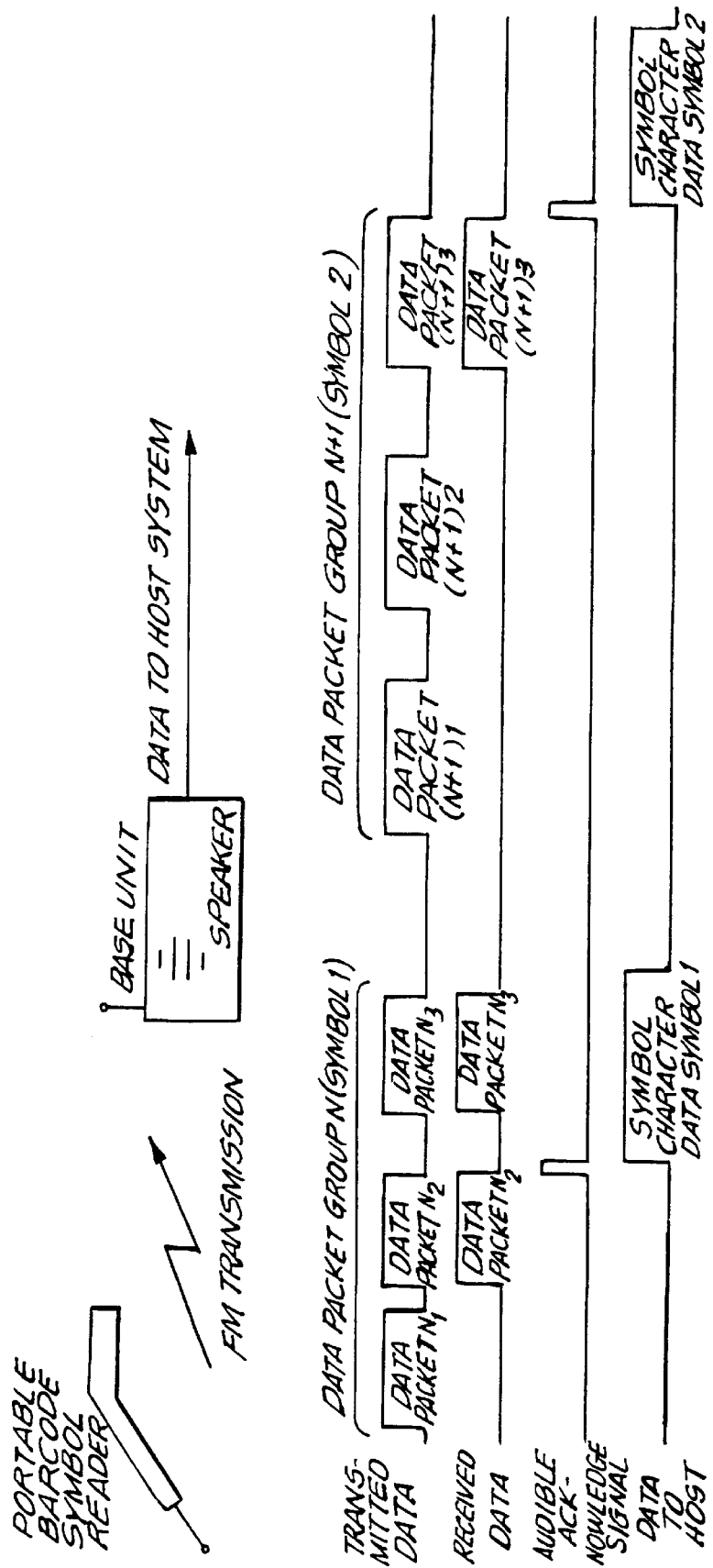
FIG. 10 is a schematic representation illustrating several groups of data packets transmitted from the bar code symbol reading device hereof in accordance with the principles of data packet transmission and reception scheme of the present invention.

In order to ensure that each base unit in the resultant system is capable of receiving at least one data packet from a data packet group transmitted by its preassigned bar code symbol reading device (i.e., without risk of interference from neighboring bar code symbol reading device transmitters), the unique "data packet group" transmission scheme shown in FIG. 10 is employed. As shown, upon the successful reading of a first bar code symbol and the production of its symbol character data $D_3$, data packet synthesis module 120 aboard the bar code symbol reading device automatically produces a first (i.e., N=1) group of (three) data packets, each having the packet format shown in FIG. 9. Thereafter, the data packet transmission circuit 121 uses the digital data bit stream, representative of the synthesized data packet group, to modulate a carrier signal transmitted from the hand-supportable bar code symbol reading device.

In the illustrative example shown FIG. 10, only the second and third data packets of the group sent over the modulated carrier signal are shown as being received by the preassigned base unit. As shown in this drawing, the base unit transmits the recovered symbol character data $D_3$ to its host computer system, upon receiving the second data packet in the transmitted group of data packets. Thereafter, the base unit produces an acoustical acknowledgement signal $S_{ACK}$ of sufficient intensity that it can be easily heard by the operator of the bar code symbol reading device that transmitted the received data packet. The function of the acoustical acknowledgment signal is to provide the operator with an audible acknowledgement that the symbol character data $D_3$ (associated with the recently read bar code symbol) has been received by the base unit and transmitted to its host computer system for processing and or subsequent storage. Notably, while the third data packet $N_3$ is also received by the base unit, the available acknowledgement signal $S_{ACK}$ and symbol character data transmission is not produced as packet $N_3$ contains redundant information already received by the second packet $N_2$ of the same group.

In the preferred embodiment, the pitch of the transmitted acoustical acknowledgement signal $S_{ACK}$ is uniquely specified and assigned to a particular bar code symbol reading unit. This way the operator of each bar code symbol reading (sub) system can easily recognize (i.e., discern) the audible acoustical acknowledgement signal produced from the base unit preassigned to his or her bar code symbol reading device. At the same time, this pitch assignment scheme allows each operator to ignore audible acoustical acknowledgment signals produced from neighboring base units not mated with his or her portable bar code symbol reading device. If after reading a bar code symbol, the operator does not see the visual "good read" indication light on its device "flash " or "blink" and immediately thereafter hear its preassigned acoustical acknowledgement signal emanate from its base unit, then the operator is implicitly informed that the symbol character data of the read bar code symbol was not successfully received by the base unit. In response to such an event, the operator simply rereads the bar code symbol and awaits to hear the acoustical acknowledgment signal emanating from the base unit.

Notably, it may even be desirable in some operating environments to produce acoustical acknowledgement signals in the form of a unique series of notes preassigned to a bar code symbol reading device and its "mated" base unit. The pitch or note sequence assigned to each mated base unit and bar code symbol reading device can be stored in a memory (e.g., EPROM) realized in the base unit, and can be programmed at the time of system set-up and modified as required. Preferably, each pitch and each note sequence is selected so that it can be readily distinguished and recognized by the operator to which it is uniquely directed.

Also shown in FIG. 10 is the case where the bar code symbol reading device reads a second bar code symbol and then transmits a second (N=2) group of data packets. However, due to interference only the third data packet in the second transmitted group of data packets is received at the respective base unit. Despite such group transmission errors (e.g., due to channel corruption or non-radio transmissive obstructions), the base unit as shown is nevertheless able to recover the transmitted symbol character data. Upon receiving the third data packet, recovering the packaged symbol character data and transmitting the same to the host computer system, the bar code symbol reading device generates an acoustical acknowledgement signal having a pitch or note sequence that the operator can hear and recognize as an indication that the data packet reception was successful.

Figure 11:
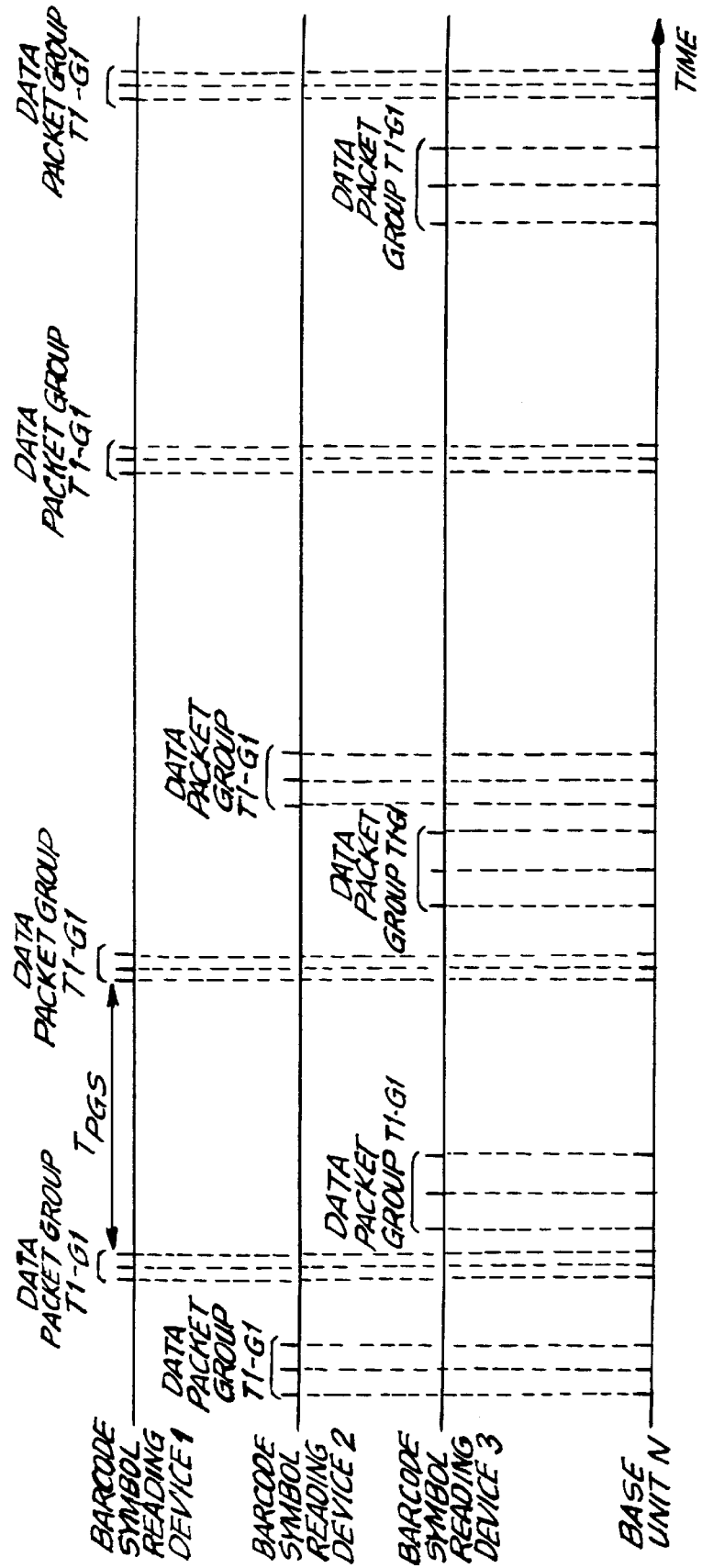
FIG. 11 is a schematic representation of an exemplary set off groups of data packet pseudo-randomly transmitted from neighboring bar code symbol reading devices, and received at one base unit in physical proximity therewith.
Figure 12:
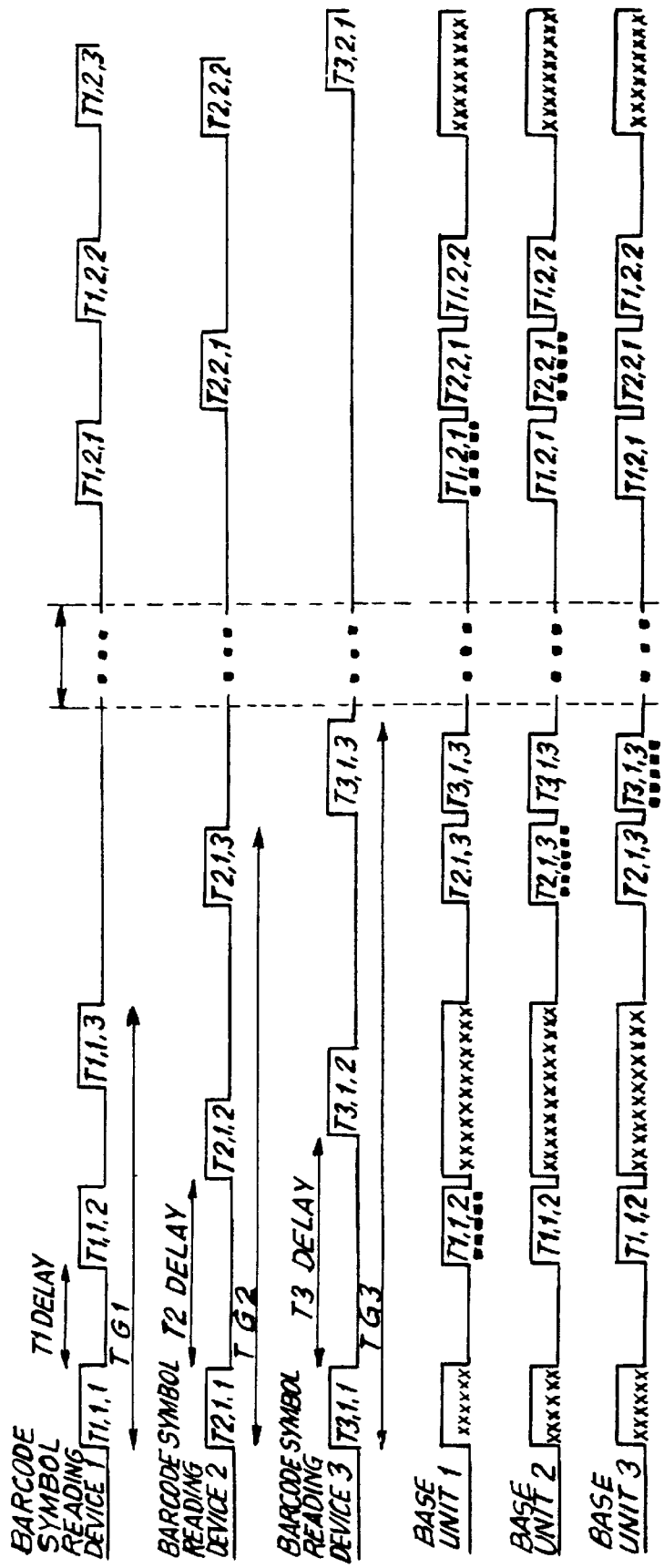
FIG. 12 is a schematic representation of an exemplary set of data packets simultaneously transmitted from three neighboring bar code symbol reading devices of the present invention, and received at the associated base units assigned thereto.

In FIGS. 11 and 12, the data packet transmission and reception scheme of the present invention is shown for the case of three station system. In the best case scenario shown in FIG. 11, the group of data packets transmitted from each bar code symbol reading device is transmitted at a time when there are no neighboring bar code symbol reading devices transmitting data packets. This case will occur most frequently, as the total transmission times for each group of data packets is selected to be substantially smaller than the random time durations lapsing naturally between adjacent data packet transmissions from neighboring bar code symbol reading devices. This fact is illustrated in FIG. 11, in which (i) a group of data packets from bar code reading device No. 1 are transmitted between adjacent groups of data packet transmitted from bar code symbol reading devices Nos. 2, 3 and 4 without the occurrence of data packet interference (i.e., collision). In most instances, the time delay between consecutive groups of data packets transmitted from any particular bar code symbol reading device, will be sufficient to permit a neighboring bar code symbol reading device to transmit at least one data packet to its base unit without the occurrence of data packet interference.

In accordance with the data transmission scheme of the present invention, data packet interference is minimized by the random presence of interference-free time slots, during which a transmitted data packet can be received at its respective base unit without neighboring packet interference. However, the present invention employs additional measures to further reduce the likelihood of data packet interference. Such measures are best appreciated when considering a high-density data packet transmission environment, in which a number of closely situated neighboring bar code symbol readers are each attempting to transmit a group of data packets to its preassigned base unit. In general, such operating conditions would present a worst case scenario for, the data packet transmission scheme of the present invention.

In the worst case scenario shown in FIG. 12, each of the four neighboring bar code symbol reading devices is assumed to consecutively read two bar code symbols and simultaneously begin the transmission of the first data packet in the first group of data packets corresponding to the first read bar code symbol. As mentioned above, each data packet is formatted essentially the same way, has substantially the same packet width, and is transmitted on a carrier signal having a frequency which is substantially the same as all other carrier signals transmitted throughout the system. In accordance with the principles of the present invention, the data packet transmission circuit 121 in each bar code symbol reading device is preprogrammed to transmit adjacent data packets with a different "time delay", as shown in FIG. 12. This condition is achieved throughout the resulting system by assigning a different Packet Time Delay to each having a different Transmitter Identification Number, and then programming the bar code symbol reading device with the preassigned Packet Time Delay parameter. As illustrated in FIG. 12, the value of the Packet Time Delay parameter programmed in each bar code symbol reading device is selected so that, when the neighboring bar code symbol reading devices simultaneously transmit groups of data packets, each base unit in the resulting system is capable of receiving at least one data packet (in a group thereof) that has been transmitted from its preassigned bar code symbol reading device. In general, the data packet delay scheme of the present invention involves selecting and programming the Packet Time Delay parameter in each bar code symbol reading device so that each base unit is periodically provided a vacant time slot, during which one transmitted data packet in each group thereof can be received free of "data packet interference", as shown in FIG. 12. The advantage of providing a packet time delay among the data packets of each transmitted group thereof is that rereading and retransmission of bar code symbols is effectively minimized under the data packet transmission scheme of the present invention.

Having described the detailed structure and internal functions of automatic bar code symbol reading device of the present invention, the operation of the control system thereof will now be described while referring to the system block diagram shown in FIG. 8 and control Blocks A to GG in FIGS. 13A to 13C.

Beginning at the START block of Main System Control Routine and proceeding to Block A of FIG. 13A, the bar code symbol reading system is "initialized". This initialization step involves, activating system override circuit 100, first control circuit $C_1$ and oscillator circuit 101. It also involves deactivating (i.e., disabling): (i) all external system components except the range selection circuit 115 and system override signal producing means 103 (i.e., infrared sensing circuit 105, laser scanning circuit 108, and photo-receiving circuit 109); (ii) all subcircuits aboard ASIC chip 133 not associated with the system override circuit 100, such as object detection circuit 107, A/D conversion circuitry 110, second control circuit $C_2$ and bar code presence detection circuit 111; and (iii) third control module 114, sypbol decoding module 119 and data packet synthesis module 120. In addition, all timers $T_1$, $T_2$, $T_3$, $T_4$, and $T_5$ are reset to t=0.

Proceeding to Block B in FIG. 13A, the first control circuit $C_1$ checks to determine whether it has received control activation signal $A_0=1$ from system override detection circuit 100. If this signal is received, then the first control circuit $C_1$ returns to Block A. If control activation signal $A_0=1$ is not received, then at Block C the first control circuit $C_1$ activates (i.e., enables) the object detection circuit by producing $E_0$. At Block D, the object detection circuit receives either the long range mode selection signal or the short range mode selection signal produced by the range selection circuit 115 and sets the appropriate sensitivity level of the circuit. At Block E, the first control circuit $C_1$ determines whether it has received control activation signal $A_1=1$, indicating that an object has been detected within the selected range of the scan field. If this control activation signal is not received, then at Block F the first control circuit $C_1$ determines whether its has received control activation signal $A_0=1$. If the first control circuit $C_1$ has received control activation signal $A_0=1$, then the control system returns to Block A in FIG. 13A, as shown. If the first control circuit $C_1$ has not received control activation signal $A_0=1$, then the control system returns to Block E, as shown.

If at Block E the first control circuit $C_1$ has received first control activation signal $A_1=1$, then at Block G the first control circuit $C_1$ (i) deactivates (i.e., disables) the object sensing circuit and the object detection circuit using disabling signal $E_0=0$, (ii) activates (i.e., enables) laser scanning circuit 108, photoreceiving circuit 109 and A/D signal conversion circuit 110 using enable signal $E_1=1$, (iii) activates bar code detection circuit 111 and second control circuit $C_2$ using enable signal $E_2=1$, and (iv) starts timer $T_1$ maintained in the first control circuit $C_1$. This permits the bar code symbol reading device to collect and analyze scan data signals for the purpose of determining whether or not a bar code is within the scan field. If at Block H the second control circuit $C_2$ does not receive control activation signal $A_{2S}=1$ or $A_{2L}=1$ from the bar code detection circuit within time period $T_1$, indicating that a bar code symbol is detected in the selected range of the scan field, then the control system returns to Block A thereby returning system control to the first control unit $C_1$, as shown in FIG. 13A. If at Block H the bar code symbol detection circuit 111 provides the second control circuit $C_2$ with control activation signal $A_{2S}=1$ or $A_{2L}=1$, as the case may be, then second control circuit $C_2$ activates (i.e., enables) third control module $C_3$ (i.e., microprocessor 134) using enable signal $E_3=1$.

At Block J, the third control module $C_3$ polls (i.e., reads) the parameter R set by range selection circuit 115 and sets a range limit flag in the symbol decoding module 119. At Block K third control module $C_3$ activates the symbol decoding module 119 using enable signal $E_4$, resets and restarts timer $T_2$ permitting it to run for a second predetermined time period (e.g., $0<T_2<1$ second), and resets and restarts timer $T_3$ permitting it to run for a third predetermined time period (e.g., $0<T_3<5$ seconds). At Block L the third control module checks to determine whether control activation signal $A_3=1$ is received from the symbol decoding module 119 within $T_2=1$ second, indicative that a bar code symbol has been successfully read (i.e., scanned and decoded) within the allotted time period. If control activation signal $A_3=1$ is not received within the time period $T_2=1$ second, then at Block M third control module $C_3$ checks to determine whether control activating signal $A_2=1$ is received. If a bar code symbol is not detected, then the control system returns to Block A, causing a state transition from bar code reading to object detection. However, if at Block M the third control module $C_3$ receives control activation signal $A_2=1$, indicative that a bar code once again is within the scan field, then at Block N the third control module $C_3$ checks to determine whether time period $T_3$ has elapsed. If it has, then the control system returns to Block A. If, however, time period $0 \leq T_3 \leq 5$ seconds has not elapsed, then at Block K the third control module $C_3$ resets and restarts timer $T_2$ to run once again for a time period $0 \leq T_2 \leq 1$ second, while $T_3$ continues to run. In essence, this provides the device at least another opportunity to read a bar code present within the scan field when the control system is at control Block L. During typical bar code reading applications, the control system may progress through the control loop defined by Blocks K-L-M-N-K several times before a bar code symbol in the scan field is read within the time period allotted by timer $T_3$.

Figure 13B:
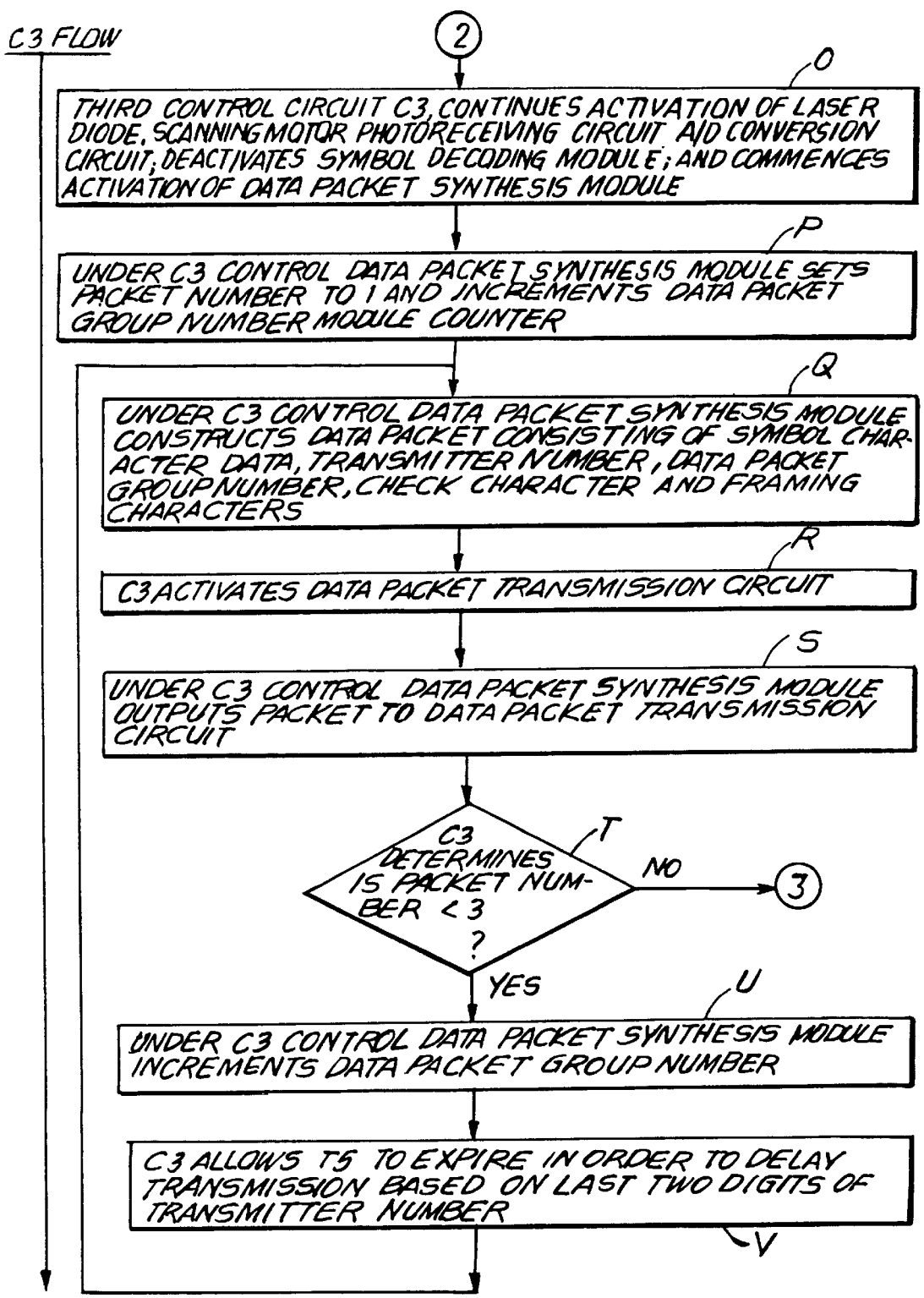
Figure 13C:
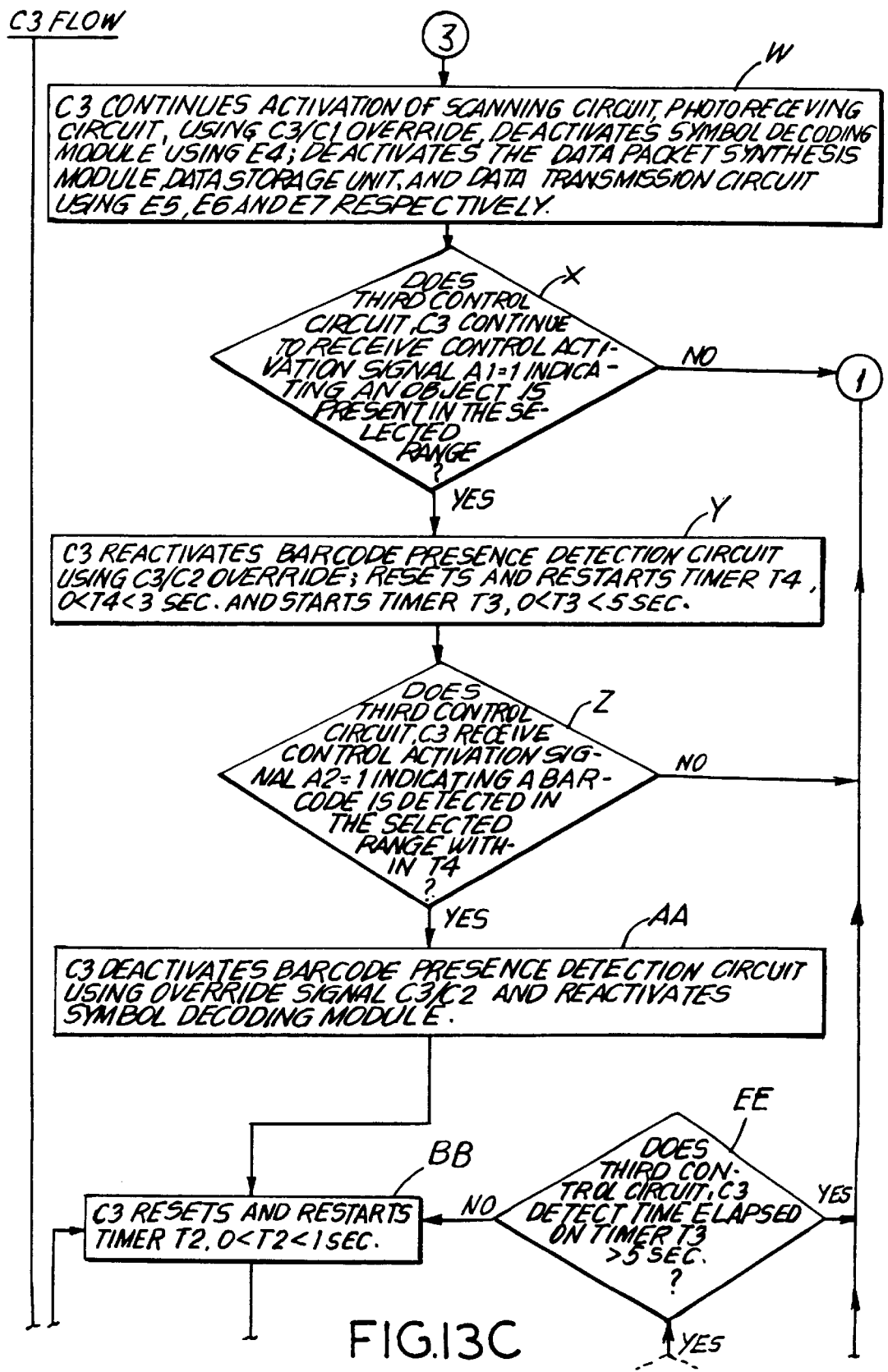
Figure 13C:
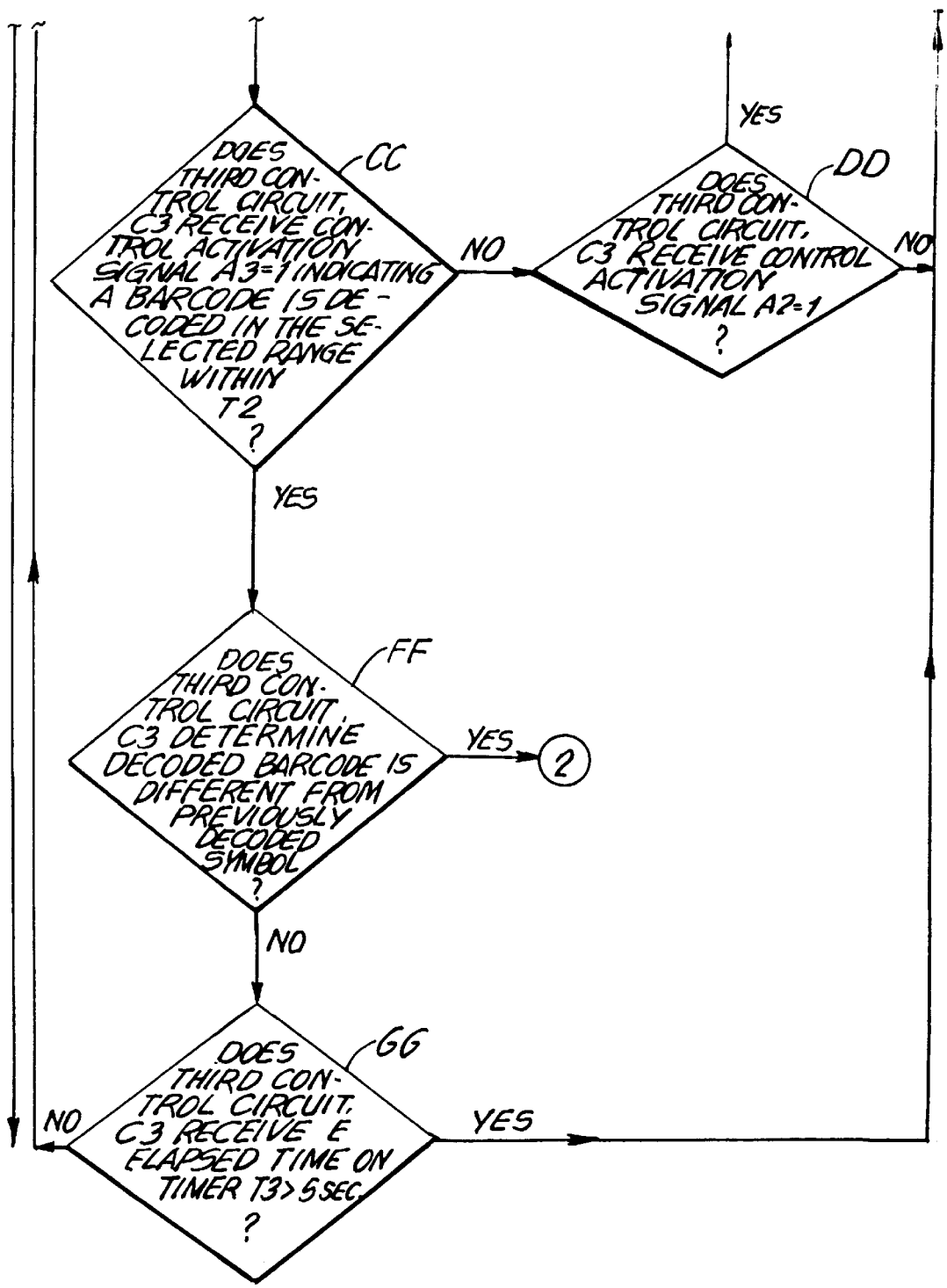

Upon receiving control activation signal $A_3=1$ from symbol decoding module 119, indicative that a bar code symbol has been successfully read, the control system proceeds to Block O in FIG. 13B. At this stage of the system control process, the third, control module $C_3$ continues activation of laser scanning circuit 108, photoreceiving circuit 109, and A/D conversion circuit 110, while deactivating symbol decoding module 119 and commencing activation of data packet synthesis module 120. While the laser beam is continuously scanned across the scan field, the operations at Blocks P to V described below, are carried out in a high speed manner under the orchestration of control module $C_3$.

As indicated at Block P, data packet synthesis module 120 first sets the Packet Number to "1", and increments the Packet Group Number from the previous number. Preferably, the data packet synthesis module keeps track of (i.e., manages) the "Packet Number" using a first modulo-N counter realized by programmable microprocessor 134, while it manages the "Packet Group Number" using a second modulo-M counter also realized by programmed microprocessor 134. In the illustrative embodiment, the first modulo counter has a cyclical count range of N=2 (i.e., 0,1,2,0,1,2, . . . ), whereas the second modulo counter has a cyclical jcount range of M=10 (i.e., 0,1,2,3,4,5,6,7,8,9,0,1,2, . . . ). At Block Q, the data packet synthesis module synthesizes or constructs a data packet having a packet format as shown in FIG. 9, i.e., consisting of symbol character data, a Transmitter Identification Number, a Packet Number, a Packet Group Number, check character, and Packet Start and End (i.e., framing) Characters. After the data packet has been formed and the digital data sequence constituting the same is buffered, the third control module $C_3$ activates at Block R the data packet transmission circuit. Thereafter at Block S, the data packet synthesis module outputs the buffered digital data sequence (of the first synthesized data packet of the group) to the data packet transmission circuit, which uses the digital data sequence to modulate the frequency of the carrier signal as it is being transmitted from the bar code symbol reading device, to its mated base unit, as described hereinabove, and then automatically deactivates itself to conserve power.

At Block T, the third control module $C_3$ determines whether the Packet Number counted by the first module counter is less than "3". If the Packet Number of the recently transmitted data packet is less than "3", indicative that at most only two data packets in a specific group have been transmitted, then at Block U the data packet synthesis module 120 increments the Packet Number by +1. At Block V, the third control module then waits for a time delay $T_5$ to lapse prior to the control system returning to Block Q, as shown in FIG. 13B. Notably, the occurrence of time delay $T_5$ causes a delay in transmission of the next data packet in the data packet group. As illustrated in FIG. 12, the duration of time delay $T_5$ is a function of the (last two digits of the) Transmitter Numbers of the current data packet group, and thus is a function of the bar code symbol reading device transmitting symbol character data to its mated base unit. For the case of three data packet groups, time delay T5 will occur between the transmission of the first and second data packets in a packet group and between the transmission of the second and third data packets in the same packet group.

Returning to Block Q, the data packet synthesis module synthesizes or constructs the second data packet in the same data packet group. After the second data packet has been formed and the digital data sequence constituting the same is buffered, the third control module $C_3$ reactivates at Block R the data packet transmission circuit. Thereafter at Block S, the data packet synthesis module outputs the-buffered digital data sequence (of the second synthesized data packet) to the data packet transmission circuit, which uses the digital data sequence to modulate the frequency of the carrier signal as it is being transmitted from the bar code symbol reading device, to its mated base unit, and thereafter automatically deactivates itself. When at Block T third control module $C_3$ determines that the Packet Number is equal to "3", the control system advances to Block W in FIG. 13C.

At Block W in FIG. 13C, the third control module $C_3$ continues activation of laser scanning circuit 108 photoreceiving circuit 109, and A/D conversion circuit 110 using control override signals $C_3/C_1$, and deactivates symbol decoding module 119, data packet synthesis module 120 and the data packet transmission circuit 121 using disable signals $E_4=0$, $E_5=0$ and $E_6=0$, respectively. Then at Block X the third control module $C_3$ determines whether control activation signal $A_1=1$, indicating that an object is present in the selected range of the scan field. If this control activation signal is not provided to the third control module $C_3$ then the control system returns to Block A, as shown. If control activation signal $A_1=1$ is received, then at Block Y the third control module $C_3$ reactivates the bar code symbol detection circuit using override signal $C_3/C_2$, and resets and restarts timer $T_3$ to start running over its predetermined time period, i.e., $0<T_3<5$ seconds, and resets and restart timer $T_4$ for a predetermined time period $0<T_4<3$ seconds.

At Block Z in FIG. 13C, the third control module $C_3$ then determines whether control activation signal $A_2=1$ is produced from the bar code symbol detection circuit 111 within time period $T_4$, indicating that a bar code symbol is present in the selected range of the scan field during this time period. If this signal is not produced within time period $T_4$, then at Block AA the third control module $C_3$ deactivates the bar code symbol detection circuit using override signal $C_3/C_2$, and reactivates the bar code symbol decoding module 119 using enable signal $E_4=1$. At Block BB, the third control module $C_3$ resets and restarts timer $T_2$ to run over its predetermined time period, i.e., $0<T_2<1$ second. At Block CC the third control module $C_3$ determines whether control activation signal $A_3=1$ is produced by the symbol decoding module within time period $T_2$, indicating that the detected bar code symbol has been successfully decoded within this time period. If this control activation signal is not produced within time period $T_2$, then at Block DD the third control module $C_3$ determines whether control activation signal $A_2=1$ is being produced from the bar code symbol detection circuit, indicating that either the same or another bar code symbol resides within the selected range of the scan field. If control activation signal $A_2=1$ is not being produced, then the control system returns to Block A, as shown. However, if this control signal is being produced, then at Block EE the third control module $C_3$ determines whether or not timer $T_3$ has lapsed, indicating that time window to read a bar code symbol without redetecting the object on which it is disposed, is closed. When this condition exists, the control system returns to Block BB FIG. 13A. However, it time remains on timer $T_3$, then at Block A in the third control module $C_3$ resets and restarts timer $T_2$ and returns to Block CC. As mentioned above, the control system may flow through the control loop defined by Blocks BB-CC-DD-EE-BB a number of times prior to reading a bar code within time period $T_3$.

When the symbol decoding module produces control activation signal $A_3=1$ within time period $T_2$, the third control module $C_3$ determines at Block FF whether the decoded bar code symbol is different from the previously decoded bar code symbol. If the decoded bar code symbol is different than the previously decoded bar code symbol, then the control system returns to Block O in FIG. 13B. If the currently decoded bar code symbol is not different than the previously decoded bar code symbol, then the third control module $C_3$ determines whether timer $T_3$ has lapsed. If the timer $T_3$ has not lapsed, then the control system returns to Block BB and reenters the control flow defined at Blocks BB through GG, attempting once again to detect and read a bar code symbol on the detected object. However, if at Block GG timer $T_3$ has lapsed, then the control system returns to Block A in FIG. 13A.

Having described the operation of the illustrative embodiment of the automatic hand-supportable bar code reading device of the present invention, it will be helpful to describe at this juncture the various conditions which cause state transitions to occur during its operation. In this regard, reference is made to FIG. 14 which provides a state transition diagram for the it illustrative embodiment.

Figure 14:
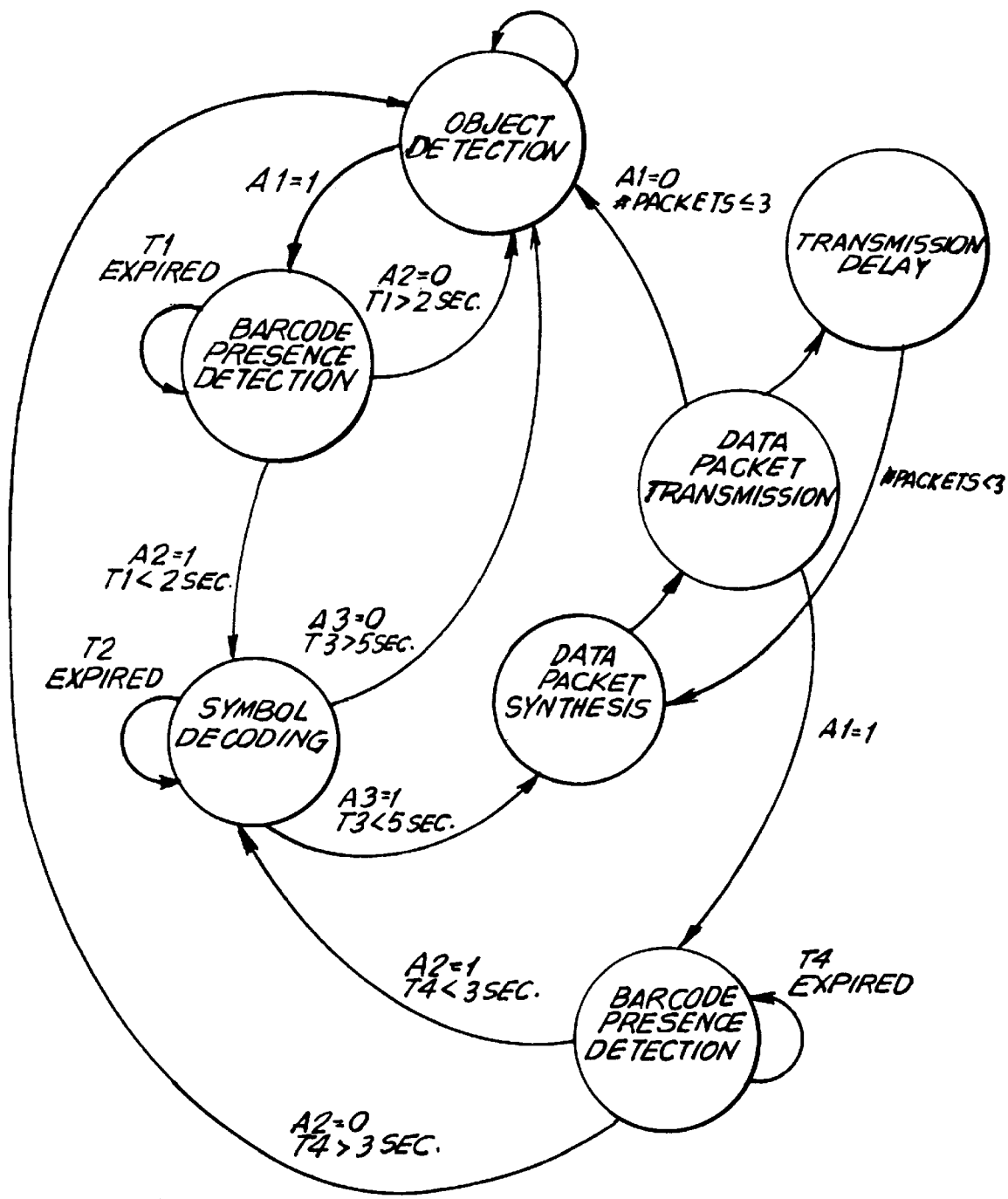
FIG. 14 is a state transition diagram illustrating the various states that the automatic hand-supportable bar code symbol reading device of the illustrative embodiment may undergo during the course of its programmed operation.

As illustrated in FIG. 14, the automatic hand-supportable bar code reading device of the present invention has four basic states of operation namely: object detection, bar code symbol presence detection, bar code symbol reading, and symbol character data transmission/storage. The nature of each of these states has been described above in great detail.

Transitions between the various states are indicated by directional arrows. Besides each set of directional arrows are transition conditions expressed in terms of control activation 11 signals (e.g., $A_1$, $A_{2S}$ or $A_{2L}$ and $A_3$, and where appropriate, state time intervals (e.g., $T_1$, $T_2$, $T_3$, $T_4$, and $T_5$) Conveniently, the state diagram of FIG. 14 expresses most simply the four basic operations occurring during the control flow within the system control program of FIGS. 13A to 13C. Significantly, the control activation signals $A_1$, $A_{2S}$ $A_{2L}$ and $A_3$ in FIG. 14 indicate which events within the object detection and/or scan fields can operate to effect a state transition within the allotted time frame(s), where prescribed.

Referring now to FIGS. 15 to 15C, the base unit of the illustrative embodiment of the present invention will be described in greater detail.

In order to perform the data packet reception, processing, retransmission, and acknowledgement functions of base unit 3 described above, a circuit board 270 is mounted within the interior volume of support stand portion 14. In the illustrated embodiment, PC board 270 is populated with electronic circuitry and devices for realizing each of the functions represented by the block shown in the system diagram of FIG. 16. As shown in FIG. 15A, flexible communication and power supply cables 7 and 8 are routed through aperture 271 formed in the lower portion of side wall of the support frame, and connect to the electronic circuitry on PC board 270.

Figure 16:
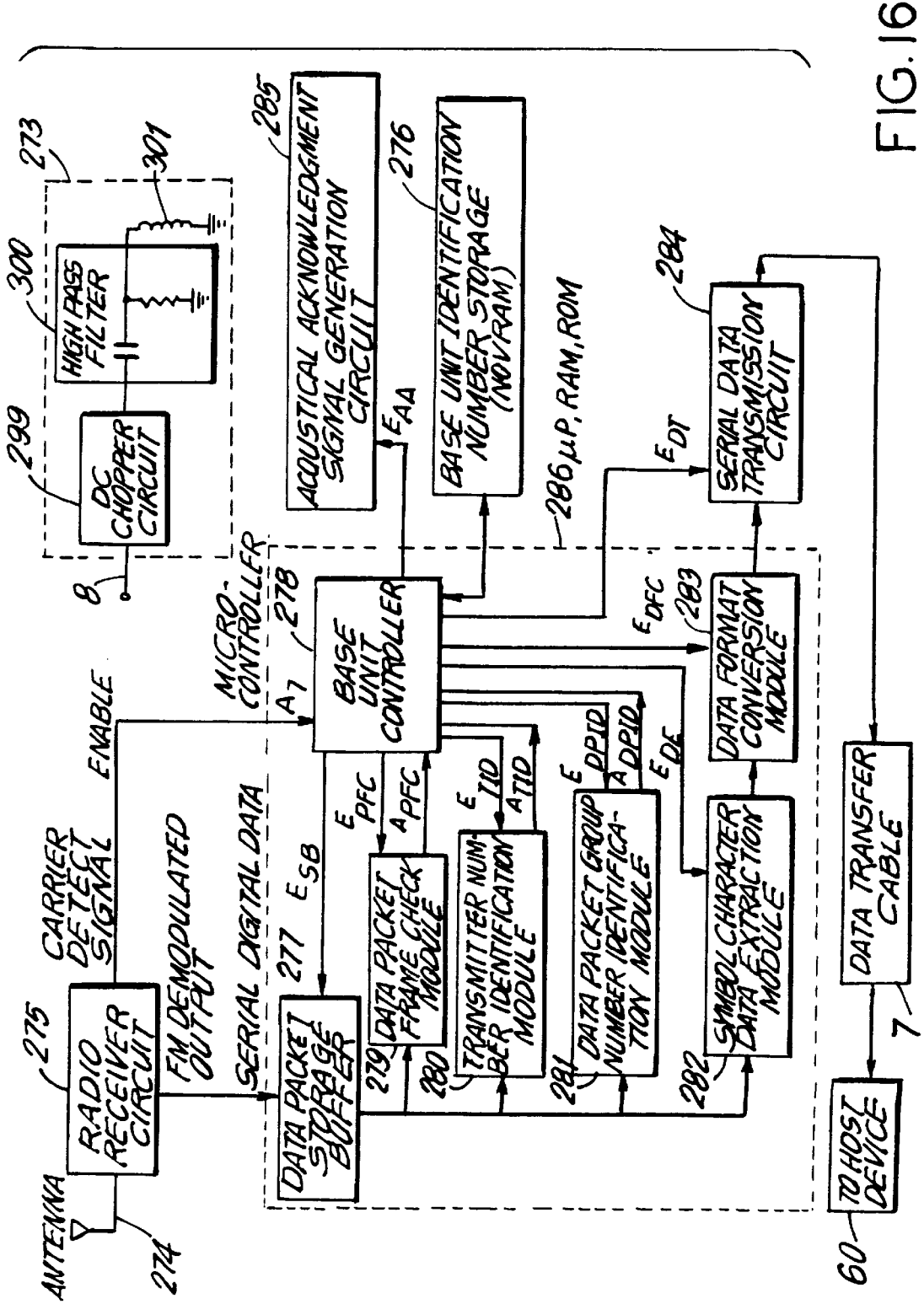
FIG. 16 is a functional block diagram of the data packet receiving and processing circuitry and the acknowledgment signal generating circuitry of the present invention realized on the printed circuit board in the base unit shown in FIGS. 15A to 15C.

In FIG. 16, the system architecture of base unit 3 is schematically represented. As shown, base unit 3 comprises a number hardware and software components, namely: a power supply circuit 273; a receiving antenna element 274; an RF carrier signal receiver circuit 275 base unit identification number storage unit 276; a data packet storage buffer 277; a base unit system controller 278; a data packet frame check module 279; a transmitter number identification module 280; a data packet number identification module 281; a symbol character data extractions module 282; a data format conversion module 283; a serial data transmission circuit 284; and an acoustical acknowledgement signal generation circuit 285. In the illustrative embodiment, a programmed microprocessor and associated memory (i.e., ROM and RAM), indicated by reference numeral 286, are used to realize the base unit system controller 278 and each of the above-described data processing modules 277 to 283. The details of such a programming implementation are known by those with ordinary skill in the art to which the present invention pertains.

As shown in FIG. 16, receiving antenna element 274 is electrically coupled to an input signal port of radio receiver circuit 275 in a conventional manner. In general, the function of radio receiver circuit 275 is to receive and process the data-packet modulated carrier signal transmitted from a remote bar code symbol reader to its mated base unit. The radio receiver circuit of the illustrative embodiment can be realized by configuring several commercially available IC chips together, although it is understood that there are certainly other ways in which to realize the basic functions of this circuit. As shown in FIG. 16A, receiving antenna 274 is connected to a matching filter circuit 287 realized using miniature inductive and capacitive components. The matching filter circuit is tuned to pass a 912 MHz RF carrier signal transmitted from the data packet transmission circuit 121 of the bar code symbol reading device. The output of matching filter circuit 287 is connected to the input of a first IC chip 288 which converts (i.e., translates) the frequency spectrum of the received modulated carrier signal down to an intermediate frequency band, for subsequent signal processing. In the illustrative embodiment, the first IC chip 288 is realized using the MAF2001 IC chip from Motorola, Inc., and provides a low noise amplifier 289, an double balanced mixer 290. A local oscillator 292 is needed to provide a local oscillator signal of about 922.7 MHZ for use in frequency down-conversion in the double balanced mixer 290. Typically, a matching filter 291 is commonly required between local oscillator 292 and mixer 290. As shown in FIG. 16A, the output of the first IC chip is provided to a band-pass filter 293 tuned to about 10.7 MHZ, the intermediate frequency band of each base unit. The intermediate signal is then provided as input to a second IC chip 294. In the illustrative embodiment, the second IC chip 294 is realized using the MC13156 IC chip commercially available from Motorola, and provides inter alia an amplification circuit, a quadrature demodulation circuit 295, a binary thresholding circuit 296, and carrier signal detection circuit 297. The function of the second IC chip is four-fold. The first function of the second IC chip is to filter and amplify the intermediate signal to produce in-phase and quadrature phase signal components for use in digital data recovery. The second function of the second IC chip is to recover an analog data signal at the base band portion of the spectrum, by providing the in-phase and quadrature-phase signal components to the quadrature demodulation circuit 295. Suitable quadrature demodulation circuitry for use in practicing the present invention is disclosed in U.S. Pat. No. 4,979,230 to Marz, which is incorporated herein by reference in its entirety. As illustrated in FIG. 16A, the third function of the second IC chip is to convert the analog data signal produced from quadrature demodulation circuit 295 into a digital data signal using a binary-level thresholding circuit 296. The fourth function of the second IC chip is to analyze the incoming signal from the output of band-pass filter 293 in order to detect the incoming carrier signal and produce a carrier detect signal $A_7$ to the base unit system controller 278. In order to produce a CMOS compatible signal, the recovered digital data signal produced from second IC chip 294 is amplified by a current amplification circuit 298 that is operative whenever a carrier signal is detected (i.e., $A_7=1$). As shown in FIG. 16, the output of current amplification, circuit 298 is a serial data stream that is clocked into data packet storage buffer 277 under the control of base unit system controller 278. In general, the data packet storage buffer 277 can be realized using a commercially available Universal Asynchronous Receiver/Transmitter (UART) device. The primary function of data packet buffer memory 277 is to buffer bytes of digital data in the produced digital data stream.

In the illustrative embodiment, it necessary to provide a means within the base unit housing, to recharge the batteries contained within the hand-supportable housing of the portable bar code symbol reading device. Typically, DC electrical power will be available from the host computer system 6, to which, the base unit is operably connected by way of flexible cables 7 and 8. An electrical arrangement for achieving this function is set forth in FIG. 16. As shown, power supply circuit 273 aboard the base unit of the present invention comprises a conventional current chopper circuit 299, a high-pass electrical filter 300 in parallel therewith, and a primary inductive coil 301 in parallel with the high-pass electrical filter. Low voltage DC electrical power provided from the host computer system by way of power cable 8 is provided to direct current (DC) chopper circuit 299, which is realized on PC board 270 using high-speed current switching circuits. The function of current chopper circuit 299 is to convert the input DC voltage to the circuit into a high-frequency triangular-type (time-varying) waveform, consisting of varilous harmonic signal components. The function of the high-pass electrical filter is to filter out the lower frequency signal components and only pass the higher frequency signal components to the inductive coil 301. As such, the high frequency electrical currents permitted to flow through inductive coil 301 induce a high voltage thereacross and produce time-varying magnetic flux (i.e., lines of force). In accordance with well known principles of electrical energy transfer, the produced magnetic flux transfers electrical power from the base unit to the rechargeable battery aboard the bar code symbol reading device, whenever the primary and secondary inductive coils aboard the base unit and the mated device are electromagnetically coupled by the magnetic flux. In order to maximize energy transfer between the base unit and its mated device during battery recharging operations, high permeability materials and well known principles of magnetic circuit design can be used, to increase the amount of magnetic flux coupling the primary and secondary inductive coils of the battery recharging circuit.

Referring to FIG. 16, the function of each of the data processing modules of base unit 3 will now be described in detail.

Upon reception of an incoming carrier signal and the recovery of the digital data stream therefrom, base unit system controller 278 orchestrates the processing of the recovered digital data stream. As shown in FIG. 16, the operation of data processing modules 279, 280, 281, 282 and 283 are enabled by the production of enable signals $E_{PFC}$, $E_{TID}$, $E_{DPID}$, $E_{DE}$, and $E_{DFC}$, respectively, from the base unit system controller.

The primary function of data packet frame check module 279 is to analyze all of the data bytes in the received data packet, including the Start and End of Packet Fields, and determine whether a complete frame (i.e., packet) of digital data bytes has been recovered from the incoming modulated carrier signal. If so, then data packet frame check module 279 produces activation control signal $A_{PFC}=1$, which is provided to the base unit system controller, as shown in FIG. 16.

The primary function of the transmitter number identification module 280 is to analyze the data bytes in the Transmitter ID Field of the received data packet and determine the Transmitter ID Number preassigned to the bar code reading device that transmitted the data packet received by the base unit. If the Transmitter ID Number of the received data packet matches the preassigned Base Unit Identification No. stored in non-volatile memory (i.e., EPROM) 302 aboard the base unit, then the transmitter number identification module generates control activation signal $A_{TID}=1$, which is provided to the base unit system controller.

The primary function of the packet number identification module 281 is to analyze the data bytes in the Packet Number Field of the received data packet and determine the Packet Number of the data packet received by the base unit. This module then advises the base unit system controller that, a different packet number was received, representing a new group (e.g., now seen) by producing an encoded signal $A_{DPID}$ during the system control process.

The primary function of the symbol character data extraction module 282 is to analyze the data bytes in the Symbol Character Data Field of the received data packet, determine the code represented by the symbol character data, and provided this symbol character data to the data format conversion module 283 under the control of the base unit system controller during the system control process.

The primary function of the data format conversion module 283 is to convert the format of the recovered symbol character data, into a data format that can be used by the Lost computer symbol 6 that is to ultimately receive and use the symbol character data. In the bar code symbol reading system of first illustrative embodiment, the data format conversion is from ASCII format to RS232 format, although it is understood that other inversions may occur in alternative embodiment of the present if invention. Typically, the data format conversion process is carried out using a data format conversion table which contains the appropriate data structure conversions.

The primary function of the serial data transmission circuit 284 is to accept the format-converted symbol character data from the data format conversion module 283, and transmit the same :1 as a serial data stream over data communication cable 7, to the data input port of the host computer system 6 (e.g., cash register, data collection device, inventory computer). Preferably, an RS-232 data communication protocol is used to facilitate the data transfer process. Thus the construction of serial data transmission circuit 284 is conventional and the details thereof are well within the knowledge of those with ordinary skill in the art.

The primary function of acoustical acknowledgement signal generation circuit 285 is to produce an acoustical acknowledgement signal SA in response to the successful recovery of symbol character data from a transmitted data packet. The purpose of the acoustical acknowledgement signal is to notify the user that the transmitted data packet has been successfully received by its mated base unit. In the illustrative embodiment, the intensity of the acoustical acknowledgement signal is such that the remotely situated user of the portable bar code symbol reader can easily hear the acoustical acknowledgement signal in an expected work environment having an average noise floor of at least about 50 decibels. Preferably, the pitch of the acoustical acknowledgement signal is within the range of about 1 to about 10 kilohertz, in order to exploit the sensitivity characteristics of the human auditory apparatus of the user. In the exemplary embodiment, the pitch is about 2.5 kilohertz. Under such conditions, the intensity of such an acoustical acknowledgement signal at its point of generation will typically need to have an output signal power of about 70 decibels in order to be heard by the user in a working environment having an average noise floor of about 50 decibels and an average noise ceiling of about 100 decibels. Acoustical acknowledgement signals of such character can be produced from acoustical acknowledgement signal generation circuit 285, shown in FIG. 16.

As shown in FIG. 16B, acoustical acknowledgement signal generation circuit 285 comprises a number of subcomponents, namely: a decoder circuit 305; a voltage controlled oscillator (VCO) driver circuit 306; a VCO circuit 307; an output amplifier circuit 308; and a piezo-electric type electro-acoustic transducer 303 having an output signal bandwidth in the audible range. The operation (i.e., duration) of the acoustical acknowledgment signal generation circuit 285 is controlled by base unit system controller 278 using enable signal $E_{AA}$. In the illustrative embodiment, enable signal $E_{AA}$ is a digital word encoded to represent one of a number of possible audible pitches or tones that are to be generated upon each successful reception of a transmitted data packet at a mated base station. The function of decoder circuit 305 is to decode the enable signal EAA produced by the base unit system controller and produce a set of voltage signals $\{V_1 1, V2, \ldots, Vn\}$ which correspond to a specified pitch sequence to be produced by eleclro-acoustic transducer 309. The function of VCO driver circuit 306 is to sequentially drive VCO circuit 307 with the produced set of voltages $\{V_1 1, V2, \ldots, Vn\}$ so that VCO circuit produces over a short time period (e.g., 0.5–1.5 seconds), a set of electrical signals having frequencies that correspond to the specified pitch sequence to be produced from the electro-acoustic transducer 309. The function of amplifier circuit 308 is to amplify these electrical, signals, whereas the function of electro-acoustical transducer 309 is to convert the amplified electrical signal set into the specified pitch sequence for the user to clearly hear in the expected operating environment. As shown in FIGS. 1 and 15A, the base housing is preferably provided with an aperture or sound port 304 so as to permit the energy of the acoustical signal from transducer 309 to freely emanate to the ambient environment of the user. In particular application, it may be desired or necessary to produce acoustical acknowledgement signal of yet greater intensity levels that those specified above. In such instances, electro-acoustical transducer 309 may be used to excite one or more tuned resonant chamber (s) mounted within or formed as part of the base unit housing.

Figure 17:
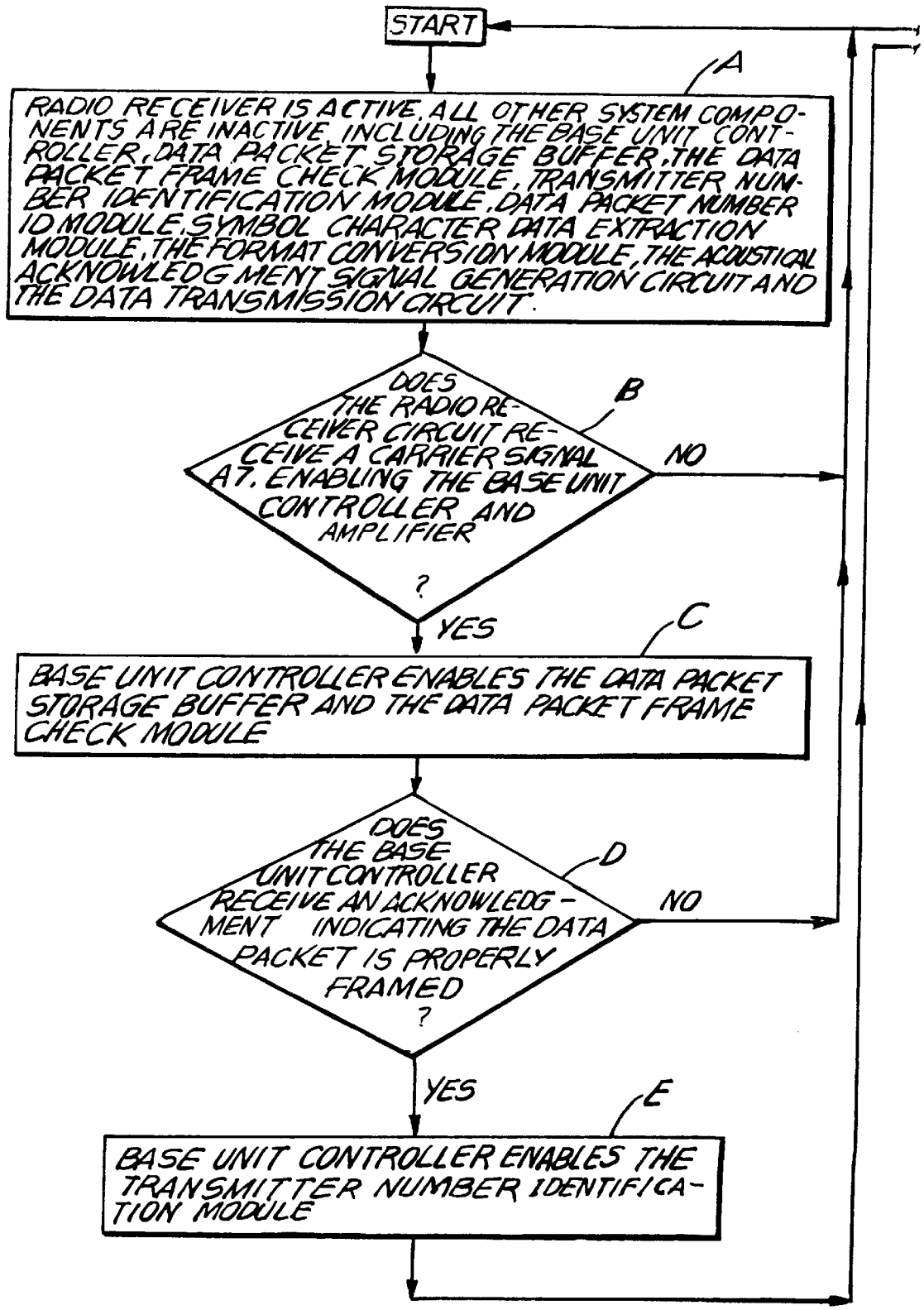
FIG. 17 and 17A is a flow chart illustrating the steps undertaken during the control process carried out in the base unit of FIG. 15A.
Figure 17A:
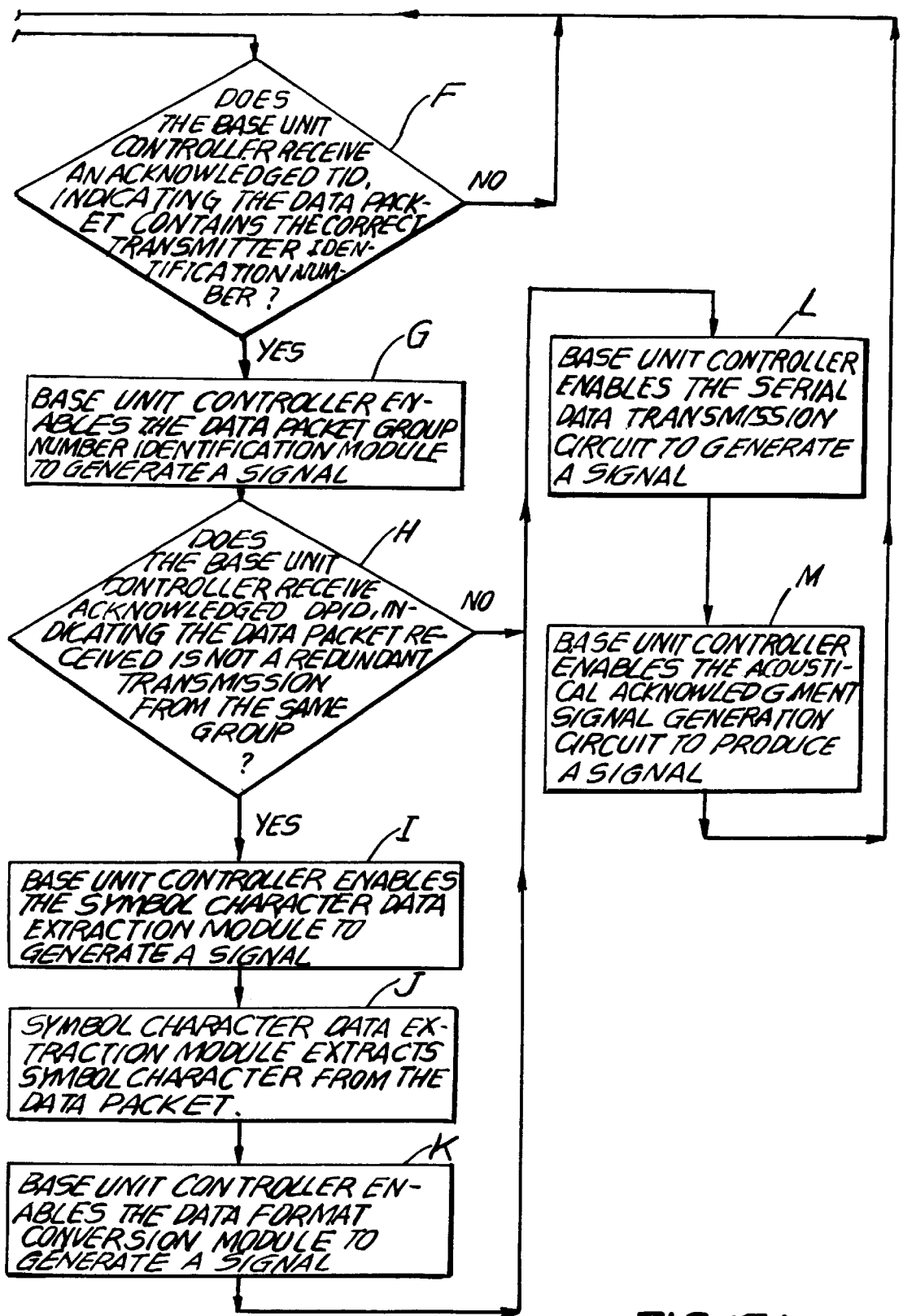

Having described the structure and general functional components of base unit 3, it is appropriate at this juncture to now describe the overall operation thereof with reference to the control process shown in FIG. 17.

As illustrated at Block A in FIG. 17, radio receiving circuit 275 is the only system component that is normally active at this stage of the base unit system control process. All other system components are inactive (i.e., disabled), including base unit system controller 278; data packet storage buffer 277, data packet frame check module 279, transmitter number identification module 280, data packet number Identification module 281, symbol character data extraction module 282, data format conversion module 283, serial data transmission circuit 284, and acoustical acknowledgement signal generation circuit 285. With the radio receiving circuit activated, the base unit is capable of receiving any modulated carrier signal transmitted from any of the bar code symbol reading devices within the data transmission range of the base unit.

At Block B in FIG. 17, radio receiving circuit 275 deter-mines whether it has received a transmitted carrier signal on its receiving antenna element 274. If it has, then the radio, receiving circuit generates a system controller activation signal $A_7$, which activates base unit system controller 278 and signal amplifier 276 shown in FIG. 16 and 16A, respectively. Then at Block C, the base unit system controller activates (i.e., enables) data packet storage buffer 277 and data packet frame check module 279 by producing activation control signals ESB=1 and $E_{PFC}$=1, respectively. At Block D, the base unit system controller determines whether it has received an acknowledgement (i.,e., control activation signal $A_{PFC}$=1) from the data packet frame check module, indicating that the received data packet is properly framed. If the received data packet is not properly framed, then the base unit returns to Block A in order to redetect an incoming carrier signal. However, if the received data packet is properly framed, then at Block E the base unit system controller enables the transmitter number identification module by generating enable signal $E_{TID}$=1.

At Block F, the base unit system controller determines whether it has received an acknowledgment (i.e., control activation signal $A_{TID}$=1) from the transmitter number identification module that the received data packet contains the correct transmitter identification number (i.e., the same number assigned to the base unit and stored in storage unit 276). If the Transmitter Identification Number contained within the received data packet does not match the base unit identification number stored in storage unit 276, then the base unit system controller returns to Block A whereupon it resumes carrier signal detection. If, however, the transmitter packet number contained within the received data packet matches the base unit identification number, then at Block G the base unit system controller enables the data packet number identification module 289 by generating enable signal $E_{DPID}$=1.

At Block H, the base unit system controller determines whether it has received an acknowledgment (i.e., control activation signal $A_{PDID}$=1) from the data packet identification module indicating that the received data packet is not a redundant data packet (i.e., from the same transmitted data packet group). If the received data packet is a redundant data packet, then the base unit system controller returns to Block A, whereupon carrier signal detection; is resumed. If, however, the received data packet is not redundant, then at Block the base unit system controller enables the symbol character data extraction module by generating enable signal $E_{DE}$=1. In response to the generation of this enable signal, the symbol data extraction module reads at Block J the symbol character data contained in the received data packet, checks the data for statistical reliability, and the writes the extracted symbol character data bytes into a storage buffer (not explicitly shown).

As indicated at Block K in FIG. 17, the base unit system controller then enables the data format conversion module by generating enable signal $E_{DFC}$=1. In response to this enable signal, the data format conversion module converts the data format of the recovered symbol character data and then buffers the format-converted symbol character data bytes in a data buffer (not explicitly shown). At Block L the base unit system controller enables the serial data transmission circuit 284 by generating enable signal $E_{DT}$=1. In response to this enable signal, the serial data transmission circuit transmits the format-converted symbol character data bytes over communication cable 7 using serial data transmission techniques well known in the art, as discussed above. When the serial data transmission process is successfully completed, the base unit system controller enables at Block M the acoustical acknowledgement signal generation circuit 285 by producing enable signal $E_{AA}$=1. In response to the production of this enable signal, acoustical acknowledgment signal generation circuit 285 generates a high intensity acoustical signal having characteristics of the type described above, thereby informing the user that a transmitted data packet has been received and that the symbol character data packaged therein has been successfully recovered and transmitted to the host computer system. Thereafter, the base unit system controller returns to the Block A, as shown.

It is appropriate at this juncture to illustrate the automatic hands-on and hands-free modes of operation of the system while utilized in different mounting installations.

Figure 18A:
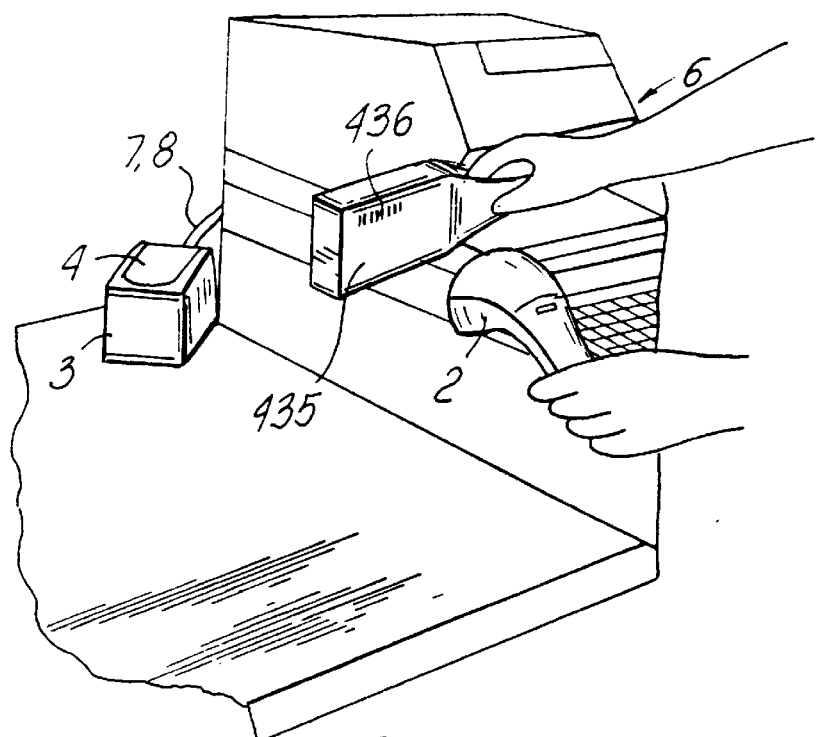
FIG. 18A is perspective view of a point-of-sale (POS) station according to the present invention, showing the automatic hand-supportable bar code symbol reading device hereof being used in its automatic "hands-free" long-range mode of operation.
Figure 18B:
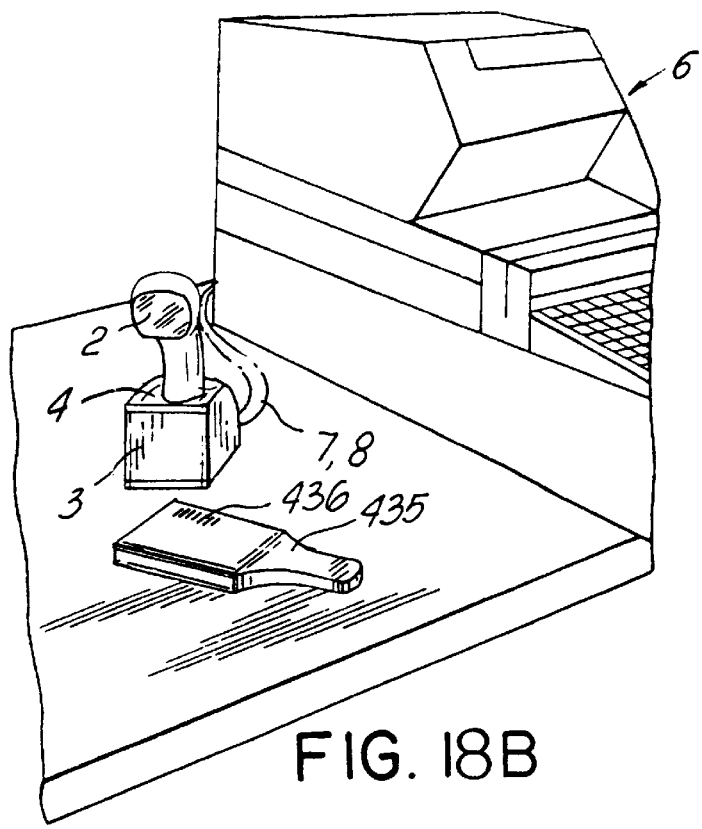
FIG. 18B is a perspective view of the POS station of FIG. 18A, showing the symbol reading device hereof being used in its automatic "hands-on" short-range mode of operation.

A point-of-sale station is shown in FIGS. 18A and 18B, as comprising an electronic cash register 6 operably connected to the automatic bar code reading system of the first illustrative embodiment by way of flexible communication cable 7. Low voltage DC power is provided to base unit 3 by way of flexible power supply cable 8. In this particular mounting installation, base unit 3 is supported on a horizontal countertop surface. If necessary or desired in such mounting installations, the base plate of base unit 3 may be weighted by affixing one or more dense mass elements to the upper surface of the base plate.

With automatic bar code reading device 2 supported within scanner support stand portion of the base unit, the system is automatically induced into its automatic long-range hands-free mode of operation. The positioning of both object detection and scan fields in this mounting installation allows bar code symbols on objects to be easily read. In order to induce the system into its short-range hands-on mode of operation, the user simply encircles the handle portion of the hand-supportable device with his or her fingers, and then lifts the device out of the scanner support stand. Upon lifting the device out of its stand, the range selection circuit 115 (e.g., including a Halt-effectmagnetic flux sensor (mounted in the handle of the housing) detects the absence of magnetic flux produced from a permanent magnet mounted in the support stand, and automatically generates the short-range control activation signal (i.e., $R_1=0$). The details of this range mode-selection mechanism can be found in copending application Ser. No. 07/761,123, now U.S. Pat. No. 5,340,971 supra.

With the automatic bar code reading device held in the user's hand, and a bar coded object 435 in the other hand, the object is moved into the short-range portion of the object detection field as shown in FIG. 18B, where the object is automatically detected, and bar code symbol 436 automatically scanned while the visible laser beam is repeatedly scanned within the scanning volume. After the bar code symbol has beer successfully read (i.e., detected and decoded) and a transmitted data packet containing symbol character data has been received and processed at base unit 3 in a manner described hereinabove, a highly audible acoustical acknowledgement signal Sack of a predetermined pitch is produced from the base unit. Thereafter, the bar code reading device is placed back within the scanner support stand, where it is once again induced into its long-range hands-free mode of operation.

Having described the preferred embodiments of the present invention, several modifications come to mind.

In the system control process of the illustrative embodiment, shown in FIG. 8, the polygon 36 is actively driven to its desired angular velocity only when the system is in its bar code symbol detection and read modes. In the illustrative embodiment, the moment of inertia of the polygon 36 is ultra-low so that it can instantly attain its desired angular velocity (from rest) in a very short time from when an object is detected within the 3-D scanning volume.

In an alternative embodiment of the present invention, the control system of the laser scanner hereof can be modified so that the scanning polygon 36 is actively driven to idle at angular velocity $W_{OD}$ when the system is in its object detection mode, and actively driven to its desired angular velocity $W_{BCD}$ (i.e., where $W_{BCD}$ $W_{OD}$) when the system is in the bar code detection mode. Using this control process, the scanning polygon is permitted to quickly attain its desired operating velocity $W_{BCD}$ when an object is detected in the scanning volume, for subsequent scan data collection operations. This control technique offers the advantage of using a polygon of a high moment of inertia, with the option of periodically imparting torque to the polygon motor shaft during the object detection state to maintain the idling velocity $W_{ODS}$ in an electrically conservative manner. The motor control circuit hereof can be readily modified to realize such a pulsed-torque functionality in the system of the present invention.

In an alternative embodiment, where power consumption is not of critical concern, the scanning polygon can be continuously driven to the desired operating velocity at each state of system operation.

The automatic bar code reading system of the present invention is capable of performing a wide variety of complex decision-making operations in real-time, endowing the system with a level of intelligence hitherto unattained in the bar code symbol reading art. Within the spirit of the present invention, additional decision-making operations may be provided to further enhance the capabilities of the system.

While the various embodiments of the projection laser scanner hereof have been described in connection with linear (1-D) code symbol scanning applications, it should be clear, however, that the projection laser scanner of the present invention is suitable for scanning 2-D code symbols as well as alphanumeric characters (e.g. textual information) in optical character recognition (OCR) applications.

While the particular illustrative embodiments shown and described above will be useful in many applications in code symbol reading, further modifications to the present invention herein disclosed will occur to persons with ordinary skill in the art. All such modifications are deemed to be within the scope and spirit of the present invention defined by the appended Claims to Invention.

What is claimed is:

1. A laser scanner comprising:
   (a) a hand-supportable housing having a light transmission window through which laser light can exit said hand-supportable housing, travel towards an object bearing a code symbol and reflect therefrom, and at least a portion of said reflected laser light travel back through said light transmission window and enter said hand-supportable housing;
   (b) an optical bench mounted in said hand-supportable housing and having a longitudinal extent which extends along a central reference axis;
   (c) a laser beam producing mechanism disposed within said hand-supportable housing for producing a laser beam;
   (d) a laser beam sweeping mechanism mounted within said hand-supportable housing with respect to said optical bench for rotation about a rotational axis intersecting said central reference axis, where the intersection of said rotational axis and said central reference axis defines a central reference plane which extends along the longitudinal extent of said optical bench, said laser beam sweeping mechanism having a plurality of rotating light reflective surfaces each being disposed at a different acute angle with respect to said rotational axis, for sequentially sweeping the laser beam about said rotational axis along a plurality of different paths;
   (e) a stationary array comprised of a plurality of stationary light reflective surfaces mounted within said hand-supportable housing with respect to said optical bench and disposed substantially under said light transmission window;
      wherein at least two of the plurality of said stationary light reflective surfaces are symmetrically disposed on opposite sides of said central reference plane, and closely adjacent said laser beam sweeping mechanism;

(f) a light collection subsystem disposed within said hand-supportable housing, and including
  (1) a light collection element, mounted along said central reference plane and adjacent at least two of said stationary light reflective surfaces, for allowing the laser beam produced from said laser beam producing mechanism to pass along a portion of said central reference plane, to said laser beam sweeping means, for sweeping about said rotational axis thereof along said plurality of different paths, and
  (2) a light receiver for receiving light from said light collection element at a point substantially within said central reference plane, and detecting the intensity of said received light and producing an electrical signal indicative of said detected intensity;

(g) a signal processor disposed within said hand-supportable housing, for processing said electrical signal and producing scan data representative of a scanned code symbol;

(h) a control mechanism within said hand-supportable housing for controlling the operation of said hand-supportable projection laser scanner so that, during scanner operation, the laser beam produced from said laser beam producing mechanism passes along a portion of said central reference plane, to at least one of the rotating light reflective surfaces of said laser beam sweeping mechanism, and as the laser beam sequentially reflects off a plurality of the rotating light reflective surfaces, the laser beam is repeatedly swept across a plurality of the stationary light reflective surfaces thereby producing a plurality of groups of plural scan lines, respectively, which are projected out through said light transmission window and intersect about a projection axis within a collimated scanning volume having an approximately columnar extent and extending from adjacent said light transmission window to at least about six inches therefrom so as to produce a highly collimated projected scanning pattern; and (i) said hand-supportable housing being supportable relative to an object bearing a code symbol so that when a code symbol is presented within said collimated scanning volume,
  (i) the code symbol is scanned omnidirectionally by said highly collimated scanning pattern,
  (ii) at least a portion of the laser light reflected from said scanned code symbol is directed through said light transmission window, reflected off at least one of said stationary light reflective surfaces, and then reflected off at least one of said rotating light reflective surfaces of said laser beam sweeping means, and
  (iii) thereafter said reflected laser light is collected by said light collection element, and received by said light receiver for detection, whereupon said electrical signal is produced for processing by said signal processor;

wherein said hand-supportable housing allows the user to easily control the direction of said projection axis by way of the handle portion of said hand-supportable housing, and thus align said collimated scanning volume with the bar code symbol on the object to be scanned and identified.

2. The laser scanner of claim 1, wherein said signal processor further comprises a data processor for decoding said scan data and producing data representative of said scanned code symbol.

3. The laser scanner of claim 1, wherein said different acute angles are selected so that the scan lines in each said group of scan lines are substantially equidistant from each other throughout at least a range of distances from said light transmission window.

4. The laser scanner of claim 1, wherein said laser beam producing mechanism comprises a laser diode mounted with respect to said optical bench.

5. The laser scanner of claim 1, wherein said first, second, third, and fourth stationary light reflective surfaces comprise first, second, third, and fourth mirrors, respectively.

6. The laser scanner of claim 1, wherein said hand-supportable housing has a head portion and handle portion extending from said head portion, and said light transmission window is disposed within said head portion.

7. The laser scanner of claim 1, wherein said highly collimated scanning pattern is oriented along the longitudinal extent of said hand-supportable housing so as to facilitate scanning of code symbols presented to said collimated scanning volume.

8. The laser scanner of claim 1, which further comprises a scanner support stand positionable upon a counter surface, and including a supporting mechanism for supporting said hand-supportable housing in any one of a plurality of positions above said counter surface so that said highly collimated scanning pattern is projected about said projection axis above said counter surface in any one of a plurality of orientations corresponding to said plurality of positions.

9. The laser scanner of claim 1, wherein said optical bench comprises a shock-mounted support structure upon which said stationary light reflective surfaces are mounted.

10. The laser scanner of claim 1, wherein said light receiver comprises a photodetector.

11. The laser scanner of claim 10, wherein said photodetector is located on a circuit board, at a height above said laser beam sweeping mechanism, substantially within said central reference plane.

12. The laser scanner of claim 1, wherein said code symbol is a bar code symbol.

13. The laser scanner of claim 1, wherein said light collecting element is a light collecting mirror having a focal distance, substantially at which said light receiver is located.

14. The laser scanner of claim 1, wherein
  each scan line in a first group of scan lines is substantially parallel to each other scan line in said first group of scan lines, and
  each scan line in a second group of scan lines is substantially parallel to each other scan line in said second group of scan lines.

15. An automatic projection laser scanning system comprising:
  a hand-supportable housing having a light transmission aperture through which visible light can exit and enter into said hand-supportable housing;
  an object detector in said hand-supportable housing, for detecting an object located in a scanning volume extending externally from said hand supportable housing, and automatically generating an activation signal in response to the detection of said object located therein;
  an activatable scan data reading mechanism in said hand-supportable housing, for reading scan data from a detected object located in said scanning volume, said scan data reading mechanism including:

a laser beam generator for generating a visible laser beam and directing said visible laser beam through said light transmission aperture and into said scanning volume, a laser beam scanner for repeatedly scanning said visible laser beam so as to produce a highly collimated scanning pattern of approximately columnar extent within said scanning volume, for scanning a code symbol on said detected object presented therein, a laser light detector for detecting the intensity of laser light reflected off said bar code symbol and passing through said light transmission aperture as said visible laser beam is repeatedly scanned within said scanning volume, and a receiver for automatically producing scan data indicative of said detected intensity;

an activatable scan data processor for processing produced scan data so as to detect and decode said bar code symbol on said detected object, and automatically producing symbol character data representative of said decoded bar code symbol; and a control mechanism for controlling the operation of said automatic bar code symbol reading system;

wherein said hand-supportable housing allows the user to control the direction of said projection axis by way of the handle portion of said hand-supportable housing, and thus align said approximately columnar scanning volume with the bar code symbol on the object to be scanned and identified.

16. The automatic projection laser scanning system of claim 15, wherein said laser beam generator comprises a laser diode.

17. The automatic projection laser scanning system of claim 15, wherein said bar code symbol has first and second envelope borders, and wherein said scan data processor comprises a detector adapted to detect the first and second envelope borders of said bar code symbol, and a mechanism for decoding said detected bar code symbol.

18. The automatic projection laser scanning system of claim 15, wherein said object detector comprises a receiver for receiving energy reflected from an object within an object detection field defined external to said housing and having an essentially volumetric extent, and wherein said highly collimated scanning pattern is characterized by at least one scanning plane having an essentially planar extent, and wherein said object detection field spatially encompasses at least a portion of said highly collimated scanning pattern.

19. The automatic projection laser scanning system of claim 15, wherein said laser beam generator is operated in a pulsed laser mode so as to generate a pulsed visible laser beam, which is directed through said light transmission aperture and repeatedly scanned across said highly collimated scanning pattern and said bar code symbol on said detected object.

20. The automatic projection laser scanning system of claim 19, wherein said object detector includes a transmitter for transmitting a pulse signal through a first optical element and into said scanning volume, a signal receiver for receiving said transmitted pulse signal reflected off said object in said scanning volume, and a signal comparator for comparing said received pulse signal with said transmitted pulse signal and automatically generating an activation signal indicative of the presence of said object in said scanning volume.

21. The automatic projection laser scanning system of claim 15, wherein said hand-supportable housing comprises a head portion and a handle portion, and wherein said object detector and said activatable scan data processor are located in said head portion.

22. The automatic projection laser scanning system of claim 20, wherein said transmitter comprises an infra-red light source in said hand-supportable housing for producing an infra-red light pulse which is transmitted through said first optical element into said scanning volume, and wherein said receiver comprises an infra-red light detector and a second optical element for focusing reflected infra-red light pulses onto said infra-red light detector.

23. A laser scanner comprising:

(a) a hand-supportable housing having a light transmission window through which laser light can exit said hand-supportable housing, travel towards an object bearing a code symbol and reflect therefrom, and at least a portion of said reflected laser light travel back through said light transmission window and enter said hand-supportable housing; at least some of the exited laser light and at least some of the reflected laser light traveling approximately in a longitudinal direction extending along a central reference axis;

(b) a laser beam producing mechanism disposed within said hand-supportable housing for producing a laser beam;

(c) a laser beam sweeping mechanism mounted within said hand-supportable housing for rotation about a rotational axis intersecting said central reference axis, where the intersection of said rotational axis and said central reference axis defines a central reference plane;

said laser beam sweeping mechanism having a plurality of rotating light reflective surfaces each being disposed at a different acute angle with respect to said rotational axis, for sequentially sweeping the laser beam about said rotational axis along a plurality of different paths;

(d) a stationary array comprised of a plurality of stationary light reflective surfaces mounted within said hand-supportable housing;

wherein at least two of the plurality of said stationary light reflective surfaces are symmetrically disposed on opposite sides of said central reference plane, and adjacent to said laser beam sweeping mechanism;

(e) a light collection mechanism disposed within said hand-supportable housing, and including (1) a light collection element, mounted along said central reference plane and adjacent at least two of said stationary light reflective surfaces, for allowing the laser beam produced from said laser beam producing mechanism to pass along a portion of said central reference plane, to said laser beam sweeping mechanism, for sweeping about said rotational axis thereof along said plurality of different paths, and (2) a light receiver for receiving light from said light collection element at a point substantially within said central reference plane, and detecting the intensity of said received light and producing an electrical signal indicative of said detected intensity;

(f) a signal processor situated within said hand-supportable housing, for processing said electrical signal and producing scan data representative of a scanned code symbol; and (g) a control mechanism within said hand-supportable housing for controlling the operation of said hand-supportable projection laser scanner so that, during scanner operation, the laser beam produced from said laser beam producing mechanism passes along a portion of said central reference plane, to at least one of the rotating light reflective surfaces of said laser beam sweeping mechanism, and as the laser beam sequentially reflects off a plurality of the rotating light reflective surfaces, the laser beam is repeatedly swept across a plurality of the stationary light reflective surfaces thereby producing a plurality of groups of plural scan lines, respectively, which are projected out through said light transmission window and intersect about a projection axis within a collimated scanning volume having an approximately columnar extent and extending from adjacent said light transmission window to at least about six inches therefrom so as to produce a highly collimated projected scanning pattern.

24. The laser scanner of claim 23 further comprising a mechanism adapted for intuitive aiming of the hand-supportable housing such that:

(i) said hand-supportable housing is supportable relative to an object bearing a code symbol wherein, when a code symbol is presented within said collimated scanning volume:

(i) the code symbol is scanned omnidirectionally by said highly collimated scanning pattern, (ii) at least a portion of the laser light reflected from said scanned code symbol is directed through said light transmission window, reflected off at least one of said stationary light reflective surfaces, and then reflected off at least one of said rotating light reflective surfaces of said laser beam sweeping means, and (iii) thereafter said reflected laser light is collected by said light collection element, and received by said light receiver for detection, whereupon said electrical signal is produced for processing by said signal processor;

and wherein said hand-supportable housing is adapted to permit a user to control the direction of said projection axis by way of the handle portion of said hand-supportable housing, and thus align said collimated scanning volume with the bar code symbol on the object to be scanned and identified.

\* \* \* \* \*